US009763955B2

(12) United States Patent
Hummel et al.

(10) Patent No.: US 9,763,955 B2
(45) Date of Patent: Sep. 19, 2017

(54) METHODS AND COMPOSITIONS FOR DECREASING GASTRIC EMPTYING

(71) Applicant: Purdue Pharma L.P., Stamford, CT (US)

(72) Inventors: Michele Hummel, Marlton, NJ (US); Donald J. Kyle, Yardley, PA (US); Garth Whiteside, Yardley, PA (US); Nathan Lautermilch, Pennington, NJ (US)

(73) Assignee: Purdue Pharma L.P., Stamford, CT (US)

( * ) Notice: Subject to any disclaimer, the term of this patent is extended or adjusted under 35 U.S.C. 154(b) by 0 days.

(21) Appl. No.: 15/048,530

(22) Filed: Feb. 19, 2016

(65) Prior Publication Data
US 2016/0243129 A1 Aug. 25, 2016

Related U.S. Application Data

(60) Provisional application No. 62/118,268, filed on Feb. 19, 2015.

(51) Int. Cl.
A61K 31/55 (2006.01)
A61K 31/40 (2006.01)
A61K 31/501 (2006.01)
A61K 31/505 (2006.01)
A61K 31/519 (2006.01)
A61K 38/31 (2006.01)
A61K 45/06 (2006.01)
A61K 31/702 (2006.01)
A61K 31/785 (2006.01)

(52) U.S. Cl.
CPC .............. A61K 31/55 (2013.01); A61K 31/40 (2013.01); A61K 31/501 (2013.01); A61K 31/505 (2013.01); A61K 31/519 (2013.01); A61K 31/702 (2013.01); A61K 31/785 (2013.01); A61K 38/31 (2013.01); A61K 45/06 (2013.01)

(58) Field of Classification Search
CPC ..................................................... A61K 31/55
USPC ........................................................ 514/256
See application file for complete search history.

(56) References Cited

U.S. PATENT DOCUMENTS

2005/0203190 A1* 9/2005 Burgard ................. A61K 31/00 514/649
2006/0276416 A1 12/2006 Sinclair et al.
2007/0020194 A1 1/2007 Greenway et al.
2009/0023740 A1 1/2009 Fulp et al.
2010/0240652 A1 9/2010 Gibson et al.
2010/0267782 A1 10/2010 Beaudoin et al.
2014/0296313 A1 10/2014 Bagal et al.

FOREIGN PATENT DOCUMENTS

| WO | 01/68612 | 9/2001 |
|---|---|---|
| WO | 01/72714 | 10/2001 |
| WO | 01/74779 | 10/2001 |
| WO | 03/008398 | 1/2003 |
| WO | 03/022285 | 3/2003 |
| WO | 03/076414 | 9/2003 |
| WO | 2004/011439 | 2/2004 |
| WO | 2008/053352 | 5/2008 |
| WO | 2011158108 | 12/2011 |
| WO | 2012/004664 | 1/2012 |
| WO | 2012/007836 | 1/2012 |
| WO | 2012/035421 | 3/2012 |
| WO | 2012/046132 | 4/2012 |
| WO | 2012/085650 | 6/2012 |
| WO | 2013/064884 | 5/2013 |
| WO | 2013/072758 | 5/2013 |
| WO | 2013/030665 | 7/2013 |
| WO | 2013/136170 | 9/2013 |
| WO | 2014/016673 | 1/2014 |
| WO | 2014/135955 | 9/2014 |
| WO | 2014/151393 | 9/2014 |

OTHER PUBLICATIONS

International search report for International Application No. PCT/US2016/018715 dated Jul. 8, 2016, 4 pages.
Leipold et al., "A de novo gain-of-function mutation in SCN11A causes loss of pain perception," Nature Genetics, Nov. 2013, vol. 45, No. 11, pp. 1399-1404.
Dishy, et al., "The effect of sildenafil on gastric emptying in patients with end-stage renal failure and symptoms of jastroparesis," Clinical Pharmacology & Therapeutics, 2004, vol. 76, No. 3 pp. 281-286.
Tappenbeck, et al., "Impact of tetrodotoxin application and lidocaine supplementation on equine jejunal smooth muscle contractility and activity of the enteric nervous system in vitro," The Veterinary Journal, 2014, 4 pgs., Elsevier Ltd.
Sarnelli, et al., "Influence of sildenafil on gastric sensorimotor function in humans," Am J Physiol Gastrointest Liver Physiol, 2004, vol. 287 pp. G988-G992.
Kim, et al., "Involvement of Na+-leak Channel in Substance P-induced Depolarization of Pacemaking Activity in Interstitial Cells of Cajal," Cell Physiol Biochem, 2012, vol. 29, pp. 501-510, Karger AG, Basel.
Beyder, et al., Loss-of-Function of the Voltage-Gated Sodium Channel Nav 1.5 (Channelopathies) in Patients With Irritable bowel Syndrome, Gastroenterology, 2014, vol. 146, pp. 1659-1668.
Kraicheley, et al., "Mehanosensitive ion channels in interstitial cells of Cajal and smooth muscle of the gastrointestinal tract," Neurogastroenterol Motil, 2007, vol. 19, pp. 245-252, Blackwell Publishing Ltd.
Smith, et al., "Morphine Decreases Enteric Neuron Excitability via Inhibition of Sodium Channels," PLOS One, Sep. 2012, vol. 7, Issue 9, pp. 1-15.
Schemann, et al., "Motor control of the stomach," European Review of Medical and Pharmacological Sciences, 2008, vol. 12, Suppl. 1, pp. 41-51.

(Continued)

Primary Examiner — Rei-Tsang Shiao
(74) Attorney, Agent, or Firm — Lowenstein Sandler LLP

(57) ABSTRACT

Disclosed in certain embodiments is a method of decreasing gastric emptying comprising administering to a subject an effective amount of a sodium-channel blocker to decrease gastric emptying.

11 Claims, 29 Drawing Sheets

(56) References Cited

OTHER PUBLICATIONS

Copel, et al., "The Nav 1.9 channel regulates colonic motility in mice," Frontiers in Neuroscience, Apr. 2013, vol. 7, Article 58, pp. 1-8.

Zakrzewska, et al., "Novel design for a phase IIa placebo-controlled, double-blind randomized withdrawal study to evaluate the safety and efficacy of CNV1014802 in patients with trigeminal neuralgia," Trials, 2013, vol. 14, No. 402, pp. 1-11.

Samsom, et al., Prevalence of Delayed Gastric Emptying in Diabetic Patients and Relationship to Dyspeptic Symptoms, Diabetes Care, Nov. 2003, vol. 26, No. 11, pp. 3116-3122.

Haba, et al., Regulation of gastroduodenal emptying of solids by gastropyloroduodenal contractions, American Physiological Society, 1993, pp. G261-G271.

Strege, et al., "Sodium current in human intestinal interstitial cells of Cajal," Am J Physiol Gastrointest Liver Physoil, 2003, vol. 285, pp. G1111-G1121.

Amato, et al., "Tetrodotoxin-dependent effects of menthol on mouse gastric motor function," European Journal of Pharmacoloty, 2013, vol. 718, pp. 131-137, Elsevier B.V.

Poole, et al., "Transient Receptor Potential Ankyrin 1 Is Expressed by Inhibitory Motoneurons of the Mouse Intestinem," Gastroenterology, 2011, vol. 141, pp. 565-575.

Engel, et al., "TRPA1 and Substance P Mediate Colitis in Mice," Gastroenterology, 2011, vol. 141, pp. 1346-1358.

Van Der Zanden, et al., Vagus Nerve Activity Augments Intestinal Macrophage Phagocytosis via Nicotinic Acetylcholine Receptor a4B2, Gastroenterology, 2009, vol. 137, pp. 1029-1039.

Martinez, et al., "Central CRF inhibits gastric emptying of a nutrient solid meal in rats: the role of CRF2 receptors," The American Physiological Society, 1998, pp. G965-G970.

\* cited by examiner

Comp. A

Comp. A carbamazepine carbamazepine

Comp. C

Comp. C

Lansoprazole

Lansoprazole

METHODS AND COMPOSITIONS FOR DECREASING GASTRIC EMPTYING

FIELD OF THE INVENTION

The present invention relates to methods and compositions for decreasing gastric emptying in a subject.

BACKGROUND

Rapid gastric emptying generally occurs when food enters into the small intestine too quickly, before all of the food is fully digested. There are two general forms of rapid gastric emptying: early and late. Early rapid gastric emptying usually occurs about ten to thirty minutes after a meal when a large amount of food enters the small intestine followed by an influx of water. Late rapid gastric emptying generally occurs about two to three hours after a meal when a rapid movement of sugar enters into the intestine, increasing the amount of insulin being produced and lowering blood glucose levels to the point of possible hypoglycemia.

Rapid gastric emptying is often seen in patients with conditions affecting the stomach's ability to store food. People who have undergone surgery for gastric bypass or for the removal of part or most of the stomach are likely to develop rapid gastric emptying since food is more likely to pass too quickly through the stomach into the intestine after these types of surgeries. Patients with conditions that affect the ability of the stomach to store and empty food, such as nerve damage to the gastrointestinal tract, are also prone to rapid gastric emptying.

There are a variety of symptoms that are associated with rapid gastric emptying. These include nausea, vomiting, abdominal pain, cramping, diarrhea, bloating, sweating, weakness, dizziness, flushing, rapid or irregular heartbeat, hypoglycemia, among other effects. Of patients with rapid gastric emptying, approximately 75% have early rapid gastric emptying while about 25% have late rapid gastric emptying, and some patients may experience both.

Patients with rapid gastric emptying often have little recourse in treating the condition. Treatment regimens generally include changing dietary habits, decreasing fluid intake, and reclining. While there are medications and surgeries available, there remains a need to provide patients suffering from rapid gastric emptying with a more viable treatment solution with fewer side effects.

All documents cited herein are hereby incorporated by reference for all purposes.

OBJECTS AND SUMMARY OF THE INVENTION

It is an object of certain embodiments of the present invention to provide a method of decreasing gastric emptying in a subject.

It is an object of certain embodiments of the present invention to provide a method of treating rapid gastric emptying in a patient in need thereof.

It is an object of certain embodiments of the present invention to provide a method of treating early rapid gastric emptying in a patient in need thereof.

It is an object of certain embodiments of the present invention to provide a method of treating late rapid gastric emptying in a patient in need thereof.

It is an object of certain embodiments of the present invention to provide a method of treating metabolic syndrome (e.g., obesity) in a patient in need thereof.

It is an object of certain embodiments of the present invention to provide a method of treating gastric disorders in patients who have undergone gastric surgery (e.g., gastric bypass surgery).

It is an object of certain embodiments of the present invention to provide a method of treating weight gain, inducing weight loss, or controlling weight management in a patient in need thereof.

It is an object of certain embodiments of the present invention to provide a method of treating increased food intake by decreasing hunger in a patient in need thereof.

It is an object of certain embodiments of the present invention to provide a method of increasing or prolonging satiety in a patient in need thereof.

It is an object of certain embodiments of the present invention to provide a method of treating diabetes mellitus (e.g., Type 1 or Type 2) in a patient in need thereof.

It is an object of certain embodiments of the present invention to provide a method for treating an indication selected from the group consisting of rapid gastric emptying, early rapid gastric emptying, late rapid gastric emptying, weight gain, increased food intake, metabolic syndrome, obesity, diabetes mellitus (type 1 and type 2), sclerodoma, migraine episodes, post-prandial rise in blood glucose, nerve damage, Zollinger-Ellison syndrome, societal burdens linked with gastric-emptying, cyclic vomiting syndrome, short bowl syndrome, impaired gastric accommodation, pouch emptying in Roux-en-Y Gastric Bypass (RYGB), and functional dyspepsia It is an object of certain embodiments of the present invention to provide a method for increasing gastric accommodation by treating impaired gastric accommodation.

It is an object of certain embodiments of the present invention to provide a method for coping with societal burden as linked to gastric falls by controlling drops in blood pressure associated with gastric emptying.

It is an object of certain embodiments of the present invention to provide a pharmaceutical composition for the methods of treatment disclosed herein, and methods of manufacture thereof.

One or more of the above objects and others are met by the present invention, which in certain embodiments is directed to a method of decreasing gastric emptying comprising: administering to a subject an effective amount of a sodium channel blocker to decrease or slow the rate of gastric emptying. In certain embodiments, the sodium channel blockers belong to a class of compounds, such as 4-N substituted pyramidine.

In certain embodiments, the present invention is directed to a method of decreasing gastric emptying comprising administering to a patient in need thereof a sodium-channel blocker of Formula I:

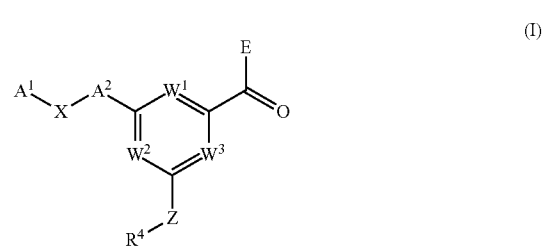

or a pharmaceutically acceptable salt, solvate, or prodrug thereof, wherein the variables are as disclosed herein.

In certain embodiments, the present invention is directed to a method of decreasing gastric emptying comprising administering to a patient in need thereof a sodium-channel blocker of Formula II.

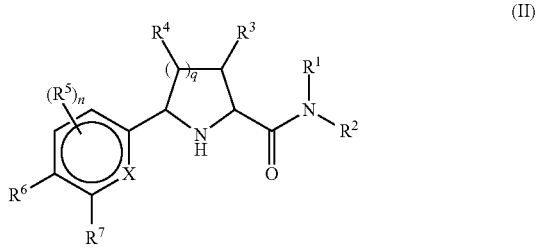

(II)

or a pharmaceutically acceptable salt, solvate, or prodrug thereof, wherein the variables are as disclosed herein.

In certain embodiments, the present invention is directed to a method of decreasing gastric emptying comprising administering to a patient in need thereof a sodium-channel blocker of Formula III:

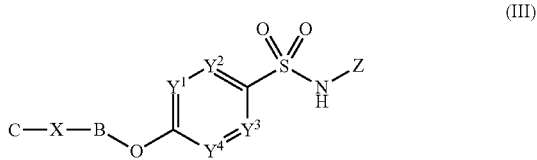

(III)

or a pharmaceutically acceptable salt, solvate, or prodrug thereof, wherein the variables are as disclosed herein.

In certain embodiments, the present invention is directed to a method of decreasing gastric emptying comprising administering to a patient in need thereof a sodium-channel blocker of Formula IV:

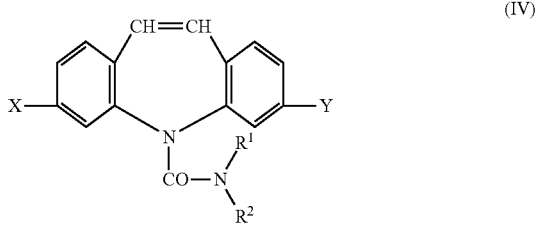

(IV)

or a pharmaceutically acceptable salt, solvate, or prodrug thereof, wherein the variables are as disclosed herein.

For the purpose of the present disclosure, the term "alkyl" as used by itself or as part of another group refers to a straight- or branched-chain aliphatic hydrocarbon containing one to twelve carbon atoms (i.e., $C_{1-12}$ alkyl) or the number of carbon atoms designated (i.e., a $C_1$ alkyl such as methyl, a $C_2$ alkyl such as ethyl, a $C_3$ alkyl such as propyl or isopropyl, etc.). In one embodiment, the alkyl group is chosen from a straight chain $C_{1-10}$ alkyl group. In another embodiment, the alkyl group is chosen from a branched chain $C_{1-10}$ alkyl group. In another embodiment, the alkyl group is chosen from a straight chain $C_{1-6}$ alkyl group. In another embodiment, the alkyl group is chosen from a branched chain $C_{1-6}$ alkyl group. In another embodiment, the alkyl group is chosen from a straight chain $C_{1-4}$ alkyl group. In another embodiment, the alkyl group is chosen from a branched chain $C_{1-4}$ alkyl group. In another embodiment, the alkyl group is chosen from a straight or branched chain $C_{2-4}$ alkyl group. Non-limiting exemplary $C_{1-10}$ alkyl groups include methyl, ethyl, propyl, isopropyl, butyl, sec-butyl, tert-butyl, iso-butyl, 3-pentyl, hexyl, heptyl, octyl, nonyl, decyl, and the like. Non-limiting exemplary $C_{1-4}$ alkyl groups include methyl, ethyl, propyl, isopropyl, butyl, sec-butyl, tert-butyl, and iso-butyl.

For the purpose of the present disclosure, the term "optionally substituted alkyl" as used by itself or as part of another group means that the alkyl as defined above is either unsubstituted or substituted with one, two, or three substituents independently chosen from nitro, haloalkoxy, aryloxy, aralkyloxy, alkylthio, sulfonamido, alkylcarbonyl, arylcarbonyl, alkylsulfonyl, arylsulfonyl, ureido, guanidino, carboxy, carboxyalkyl, cycloalkyl, and the like. In one embodiment, the optionally substituted alkyl is substituted with two substituents. In another embodiment, the optionally substituted alkyl is substituted with one substituent. Non-limiting exemplary optionally substituted alkyl groups include —$CH_2CH_2NO_2$, —$CH_2CH_2CO_2H$, —$CH_2CH_2SO_2CH_3$, —$CH_2CH_2COPh$, —$CH_2C_6H_{11}$, and the like.

For the purpose of the present disclosure, the term "cycloalkyl" as used by itself or as part of another group refers to saturated and partially unsaturated (containing one or two double bonds) cyclic aliphatic hydrocarbons containing one to three rings having from three to twelve carbon atoms (i.e., $C_{3-12}$ cycloalkyl) or the number of carbons designated. In one embodiment, the cycloalkyl group has two rings. In one embodiment, the cycloalkyl group has one ring. In another embodiment, the cycloalkyl group is chosen from a $C_{3-8}$ cycloalkyl group. In another embodiment, the cycloalkyl group is chosen from a $C_{3-6}$ cycloalkyl group. Non-limiting exemplary cycloalkyl groups include cyclopropyl, cyclobutyl, cyclopentyl, cyclohexyl, cycloheptyl, cyclooctyl, norbornyl, decalin, adamantyl, cyclohexenyl, and the like.

For the purpose of the present disclosure, the term "optionally substituted cycloalkyl" as used by itself or as part of another group means that the cycloalkyl as defined above is either unsubstituted or substituted with one, two, or three substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, and (heteroaryl)alkyl. In one embodiment, the optionally substituted cycloalkyl is substituted with two substituents. In another embodiment, the optionally substituted cycloalkyl is substituted with one substituent. Non-limiting exemplary optionally substituted cycloalkyl groups include:

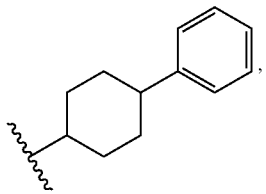

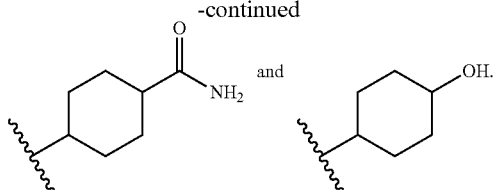
and
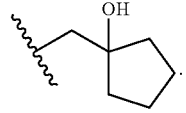

For the purpose of the present disclosure, the term "haloalkyl" as used by itself or as part of another group refers to an alkyl group substituted by one or more fluorine, chlorine, bromine and/or iodine atoms. In one embodiment, the alkyl group is substituted by one, two, or three fluorine and/or chlorine atoms. In another embodiment, the haloalkyl group is chosen from a $C_{1-4}$ haloalkyl group. Non-limiting exemplary haloalkyl groups include fluoromethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl groups.

For the purpose of the present disclosure, the term "hydroxyalkyl" as used by itself or as part of another group refers to an alkyl group substituted with one or more, e.g., one, two, or three, hydroxy groups. In one embodiment, the hydroxyalkyl group is a monohydroxyalkyl group, i.e., substituted with one hydroxy group. In another embodiment, the hydroxyalkyl group is a dihydroxyalkyl group, i.e., substituted with two hydroxy groups. In another embodiment, the hydroxyalkyl group is chosen from a $C_{1-4}$ hydroxyalkyl group. Non-limiting exemplary hydroxyalkyl groups include hydroxymethyl, hydroxyethyl, hydroxypropyl and hydroxybutyl groups, such as 1-hydroxyethyl, 2-hydroxyethyl, 1,2-dihydroxyethyl, 2-hydroxypropyl, 3-hydroxypropyl, 3-hydroxybutyl, 4-hydroxybutyl, 2-hydroxy-1-methylpropyl, and 1,3-dihydroxyprop-2-yl.

For the purpose of the present disclosure, the term "(cycloalkyl)alkyl" as used by itself or as part of another group refers to an alkyl group substituted with at least one optionally substituted cycloalkyl group. Non-limiting exemplary (cycloalkyl)alkyl groups include:

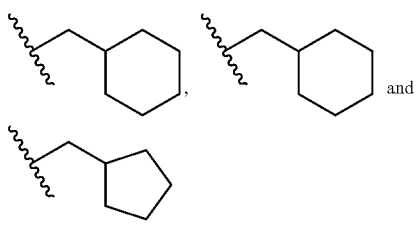

For the purpose of the present disclosure, the term "hydroxy(cycloalkyl)alkyl" as used by itself or as part of another group refers to (cycloalkyl)alkyl group substituted with at least one hydroxy group. The hydroxy group(s) can be at any available position. Non-limiting exemplary hydroxy(cycloalkyl)alkyl groups include:

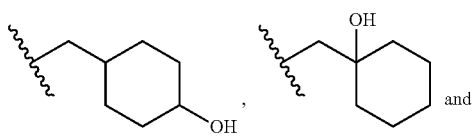

For the purpose of the present disclosure, the term "alkoxy" as used by itself or as part of another group refers to an optionally substituted alkyl, optionally substituted cycloalkyl, optionally substituted alkenyl, optionally substituted cycloalkenyl. In one embodiment, the alkoxy group is chosen from a $C_{1-4}$ alkoxy group. In another embodiment, the alkoxy group is chosen from a $C_{1-4}$ alkyl attached to a terminal oxygen atom, e.g., methoxy, ethoxy, and tert-butoxy.

For the purpose of the present disclosure, the term "alkylthio" as used by itself or as part of another group refers to a sulfur atom substituted by an optionally substituted alkyl group. In one embodiment, the alkylthio group is chosen from a $C_{1-4}$ alkylthio group. Non-limiting exemplary alkylthio groups include —$SCH_3$, and —$SCH_2CH_3$.

For the purpose of the present disclosure, the term "alkoxyalkyl" as used by itself or as part of another group refers to an alkyl group substituted with an alkoxy group. Non-limiting exemplary alkoxyalkyl groups include methoxymethyl, methoxyethyl, methoxypropyl, methoxybutyl, ethoxymethyl, ethoxyethyl, ethoxypropyl, ethoxybutyl, propoxymethyl, iso-propoxymethyl, propoxyethyl, propoxypropyl, butoxymethyl, tert-butoxymethyl, isobutoxymethyl, sec-butoxymethyl, and pentyloxymethyl.

For the purpose of the present disclosure, the term "heteroalkyl" as used by itself or part of another group refers to a stable straight or branched chain hydrocarbon radical containing 1 to 10 carbon atoms and at least two heteroatoms, which can be the same or different, selected from O, N, or S, wherein: 1) the nitrogen atom(s) and sulfur atom(s) can optionally be oxidized; and/or 2) the nitrogen atom(s) can optionally be quaternized. The heteroatoms can be placed at any interior position of the heteroalkyl group or at a position at which the heteroalkyl group is attached to the remainder of the molecule. In one embodiment, the heteroalkyl group contains two oxygen atoms. Non-limiting exemplary heteroalkyl groups include —$CH_2OCH_2CH_2OCH_3$, —$OCH_2CH_2OCH_2CH_2OCH_3$, —$CH_{-2}NHCH_2CH_2OCH_2$, —$OCH_2CH_2NH_2$, and —$NHCH_2CH_2N(H)CH_3$.

For the purpose of the present disclosure, the term "haloalkoxy" as used by itself or as part of another group refers to a haloalkyl attached to a terminal oxygen atom. Non-limiting exemplary haloalkoxy groups include fluoromethoxy, difluoromethoxy, trifluoromethoxy, and 2,2,2-trifluoroethoxy.

For the purpose of the present disclosure, the term "aryl" as used by itself or as part of another group refers to a monocyclic or bicyclic aromatic ring system having from six to fourteen carbon atoms (i.e., $C_{6-14}$ aryl). Non-limiting exemplary aryl groups include phenyl (abbreviated as "Ph"), naphthyl, phenanthryl, anthracyl, indenyl, azulenyl, biphenyl, biphenylenyl, and fluorenyl groups. In one embodiment, the aryl group is chosen from phenyl or naphthyl.

For the purpose of the present disclosure, the term "optionally substituted aryl" as used herein by itself or as part of another group means that the aryl as defined above is either unsubstituted or substituted with one to five substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, or (heteroaryl)alkyl. In one embodiment, the optionally substituted aryl is an optionally substituted phenyl. In one embodiment, the optionally substituted phenyl has four substituents. In another embodiment, the optionally substituted phenyl has three substituents. In another embodiment, the optionally substituted phenyl has two substituents. In another embodiment, the optionally substituted phenyl has one substituent. Non-limiting exemplary substituted aryl groups include 2-methylphenyl, 2-methoxyphenyl, 2-fluorophenyl, 2-chlorophenyl, 2-bromophenyl, 3-methylphenyl, 3-methoxyphenyl, 3-fluorophenyl, 3-chlorophenyl, 4-methylphenyl, 4-ethylphenyl, 4-methoxyphenyl, 4-fluorophenyl, 4-chlorophenyl, 2,6-di-fluorophenyl, 2,6-di-chlorophenyl, 2-methyl, 3-methoxyphenyl, 2-ethyl, 3-methoxyphenyl, 3,4-di-methoxyphenyl, 3,5-di-fluorophenyl 3,5-di-methylphenyl, 3,5-dimethoxy, 4-methylphenyl, 2-fluoro-3-chlorophenyl, and 3-chloro-4-fluorophenyl. The term optionally substituted aryl is meant to include groups having fused optionally substituted cycloalkyl and fused optionally substituted heterocyclo rings. Examples include:

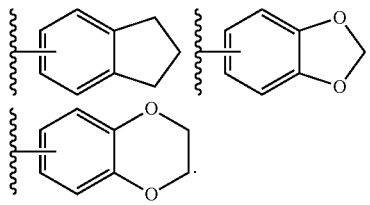

For the purpose of the present disclosure, the term "heteroaryl" or "heteroaromatic" refers to monocyclic and bicyclic aromatic ring systems having 5 to 14 ring atoms (i.e., $C_{5-14}$ heteroaryl) and 1, 2, 3, or 4 heteroatoms independently chosen from oxygen, nitrogen and sulfur. In one embodiment, the heteroaryl has three heteroatoms. In another embodiment, the heteroaryl has two heteroatoms. In another embodiment, the heteroaryl has one heteroatom. In one embodiment, the heteroaryl is a $C_5$ heteroaryl. In another embodiment, the heteroaryl is a $C_6$ heteroaryl. Non-limiting exemplary heteroaryl groups include thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, β-carbolinyl, phenanthridinyl, acridinyl, pyrimidinyl, phenanthrolinyl, phenazinyl, thiazolyl, isothiazolyl, phenothiazolyl, isoxazolyl, furazanyl, and phenoxazinyl. In one embodiment, the heteroaryl is chosen from thienyl (e.g., thien-2-yl and thien-3-yl), furyl (e.g., 2-furyl and 3-furyl), pyrrolyl (e.g., 1H-pyrrol-2-yl and 1H-pyrrol-3-yl), imidazolyl (e.g., 2H-imidazol-2-yl and 2H-imidazol-4-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, pyrimidin-5-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl (e.g., oxazol-2-yl, oxazol-4-yl, and oxazol-5-yl) and isoxazolyl (e.g., isoxazol-3-yl, isoxazol-4-yl, and isoxazol-5-yl). The term "heteroaryl" is also meant to include possible N-oxides. Exemplary N-oxides include pyridyl N-oxide and the like.

For the purpose of the present disclosure, the term "optionally substituted heteroaryl" as used by itself or as part of another group means that the heteroaryl as defined above is either unsubstituted or substituted with one to four substituents, e.g., one or two substituents, independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, and (heteroaryl)alkyl. In one embodiment, the optionally substituted heteroaryl has one substituent. In one embodiment, the optionally substituted is an optionally substituted pyridyl, i.e., 2-, 3-, or 4-pyridyl. Any available carbon or nitrogen atom can be substituted. In another embodiment, the optionally substituted heteroaryl is an optionally substituted indole.

For the purpose of the present disclosure, the term "heterocycle" or "heterocyclo" as used by itself or as part of another group refers to saturated and partially unsaturated (e.g., containing one or two double bonds) cyclic groups containing one, two, or three rings having from three to fourteen ring members (i.e., a 3- to 14-membered heterocyclo) and at least one heteroatom. Each heteroatom is independently selected from the group consisting of oxygen, sulfur, including sulfoxide and sulfone, and/or nitrogen atoms, which can be quaternized. The term "heterocyclo" is meant to include cyclic ureido groups such as 2-imidazolidinone and cyclic amide groups such as β-lactam, γ-lactam, δ-lactam and ε-lactam. The term "heterocyclo" is also meant to include groups having fused optionally substituted aryl groups, e.g., indolinyl. In one embodiment, the heterocyclo group is chosen from a 5- or 6-membered cyclic group containing one ring and one or two oxygen and/or nitrogen atoms. The heterocyclo can be optionally linked to the rest of the molecule through a carbon or nitrogen atom. Non-limiting exemplary heterocyclo groups include 2-imidazolidinone, piperidinyl, morpholinyl, piperazinyl, pyrrolidinyl, and indolinyl.

For the purpose of the present disclosure, the term "optionally substituted heterocyclo" as used herein by itself or part of another group means the heterocyclo as defined above is either unsubstituted or substituted with one to four substituents independently selected from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, (heteroaryl)alkyl, and the like. Substitution may occur on any available carbon or nitrogen atom, and may form a spirocycle. Non-limiting exemplary optionally substituted heterocyclo groups include:

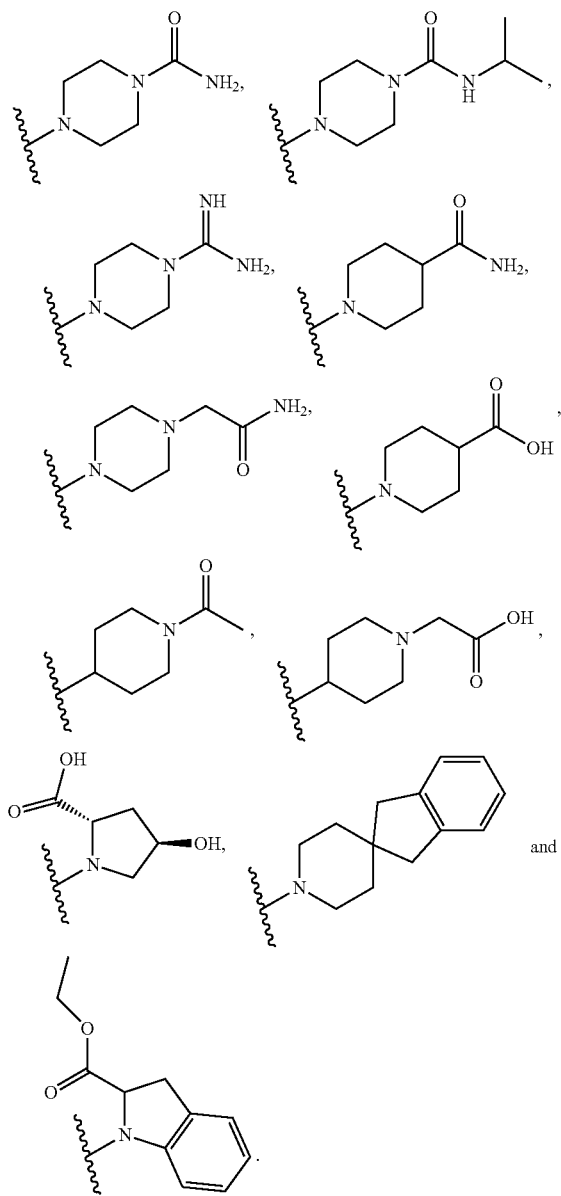

For the purpose of the present disclosure, the term "amino" as used by itself or as part of another group refers to —NH$_2$.

For the purpose of the present disclosure, the term "alkylamino" as used by itself or as part of another group refers to —NHR$^{15}$, wherein R$^{15}$ is alkyl.

For the purpose of the present disclosure, the term "dialkylamino" as used by itself or as part of another group refers to —NR$^{16a}$R$^{16b}$ wherein R$^{16a}$ and R$^{16b}$ are each independently alkyl or R$^{16a}$ and R$^{16b}$ are taken together to form a 3- to 8-membered optionally substituted heterocyclo.

For the purpose of the present disclosure, the term "hydroxyalkylamino" as used by itself or as part of another group refers to —NHR$^{17}$, wherein R$^{17}$ is hydroxyalkyl.

For the purpose of the present disclosure, the term "cycloalkylamino" as used by itself or as part of another group refers to —NR$^{19a}$R$^{19b}$, wherein R$^{19a}$ is optionally substituted cycloalkyl and R$^{19b}$ is hydrogen or alkyl.

For the purpose of the present disclosure, the term "(amino)alkyl" as used by itself or as part of another group refers to an alkyl group substituted with an amino group. Non-limiting exemplary amino alkyl groups include —CH$_2$CH$_2$NH$_2$, —CH$_2$CH$_2$CH$_2$NH$_2$, —CH$_2$CH$_2$CH$_2$CH$_2$NH$_2$ and the like.

For the purpose of the present disclosure, the term "(alkylamino)alkyl" as used by itself or as part of another group refers alkyl group substituted an alkylamino group. A non-limiting exemplary (alkylamino)alkyl group is —CH$_2$CH$_2$N(H)CH$_3$.

For the purpose of the present disclosure, the term "(dialkylamino)alkyl" as used by itself or as part of another group refers to an alkyl group substituted by a dialkylamino group. A non-limiting exemplary (dialkylamino)alkyl group is —CH$_2$CH$_2$N(CH$_3$)$_2$.

For the purpose of the present disclosure, the term "(cyano)alkyl" as used by itself or as part of another group refers to an alkyl group substituted with one or more cyano, e.g., —CN, groups. Non-limiting exemplary (cyano)alkyl groups include —CH$_2$CH$_2$CN, —CH$_2$CH$_2$CH$_2$CN, and —CH$_2$CH$_2$CH$_2$CH$_2$CN.

For the purpose of the present disclosure, the term "carboxamido" as used by itself or as part of another group refers to a radical of formula —C(=O)NR$^{24a}$R$^{24b}$, wherein R$^{24a}$ and R$^{24b}$ are each independently hydrogen, optionally substituted alkyl, optionally substituted aryl, or optionally substituted heteroaryl, or R$^{24a}$ and R$^{24b}$ taken together with the nitrogen to which they are attached from a 3- to 8-membered heterocyclo group. In one embodiment, R$^{24a}$ and R$^{24b}$ are each independently hydrogen or optionally substituted alkyl. Non-limiting exemplary carboxamido groups include —CONH$_2$, —CON(H)CH$_3$, CON(CH$_3$)$_2$, and CON(H)Ph.

For the purpose of the present disclosure, the term "(carboxamido)alkyl" as used by itself or as part of another group refers to an alkyl group with a carboxamido group. Non-limiting exemplary (carboxamido)alkyl groups include —CH$_2$CONH$_2$, —C(H)CH$_3$—CONH$_2$, and —CH$_2$CON(H)CH$_3$.

For the purpose of the present disclosure, the term "alkylsulfonyl" as used by itself or as part of another group refers to a sulfonyl group, i.e., —SO$_2$—, substituted by any of the above-mentioned optionally substituted alkyl groups. A non-limiting exemplary alkylsulfonyl group is —SO$_2$CH$_3$.

For the purpose of the present disclosure, the term "carboxyalkyl" as used by itself or as part of another group refers to any of the above-mentioned alkyl groups substituted with a —COOH. A non-limiting exemplary carboxyalkyl group is —CH$_2$CO$_2$H.

For the purpose of the present disclosure, the term "aralkyl" as used by itself or as part of another group refers to an alkyl group substituted with one, two, or three optionally substituted aryl groups. In one embodiment, the aralkyl group is a C$_{1-4}$ alkyl substituted with one optionally substituted aryl group. Non-limiting exemplary aralkyl groups include benzyl, phenethyl, —CHPh$_2$, and —CH(4-F-Ph)$_2$.

For the purpose of the present disclosure, the term "(heterocyclo)alkyl" as used by itself or as part of another group refers to an alkyl group substituted with one, two, or three optionally substituted heterocyclo groups. In one embodiment, the (heterocyclo)alkyl is a (C$_{1-4}$)alkyl substituted with one optionally substituted heterocyclo group. Non-limiting exemplary (heterocyclo)alkyl groups include:

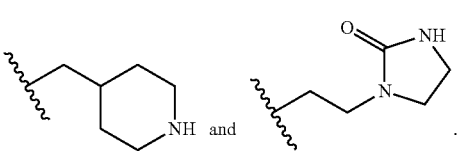 [SMILES: *CC1CCNCC1 ; *CCN1CCNC1=O]

For the purpose of the present disclosure, the term "(heteroaryl)alkyl" as used by itself or as part of another group refers to an alkyl group substituted with one, two, or three optionally substituted heteroaryl groups. In one embodiment, the (heteroaryl)alkyl group is a $(C_{1-4})$alkyl substituted with one optionally substituted heteroaryl group. Non-limiting exemplary (heteroaryl)alkyl groups include:

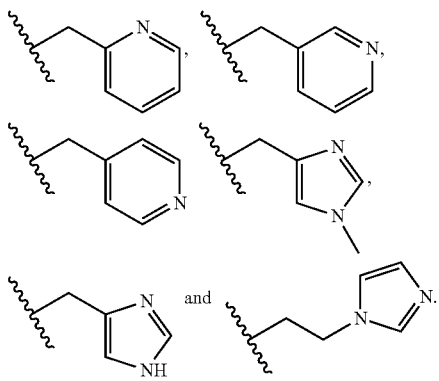

The present disclosure encompasses prodrugs of any of the disclosed compounds. As used herein, prodrugs are considered to be any covalently bonded carriers that release the active parent drug in vivo. In general, such prodrugs will be functional derivatives of compounds disclosed herein which will be readily convertible in vivo, e.g., by being metabolized. Conventional procedures for the selection and preparation of suitable prodrug derivatives are described in, for example, *Design of Prodrugs*, H. Bundgaard ed., Elsevier (1985); "Drug and Enzyme Targeting, Part A," K. Widder et al. eds., Vol. 112 in *Methods in Enzymology*, Academic Press (1985); Bundgaard, "Design and Application of Prodrugs," Chapter 5 (pp. 113-191) in *A Textbook of Drug Design and Development*, P. Krogsgaard-Larsen and H. Bundgaard eds., Harwood Academic Publishers (1991); Bundgaard et al., *Adv. Drug Delivery Revs.* 8:1-38 (1992); Bundgaard et al., *J. Pharmaceut. Sci.* 77:285 (1988); and Kakeya et al., *Chem. Pharm. Bull.* 32:692 (1984). Non-limiting examples of prodrugs include esters or amides of compounds disclosed herein having hydroxyalkyl or aminoalkyl as a substituent, and these can be prepared by reacting such parent compounds with anhydrides such as succinic anhydride.

The present disclosure encompasses any of the compounds disclosed herein which are isotopically-labelled (i.e., radiolabeled) by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Isotopically-labeled compounds can be prepared by methods known in the art.

The present disclosure encompasses $^{3}H$, $^{11}C$, or $^{14}C$ radiolabeled compounds disclosed herein and the use of any such compounds as radioligands for their ability to bind to the sodium channel. For example, one use of the labeled compounds of the present disclosure is the characterization of specific receptor binding. Another use of a labeled compound is an alternative to animal testing for the evaluation of structure-activity relationships. For example, the receptor assay can be performed at a fixed concentration of a labeled compound and at increasing concentrations of a test compound in a competition assay. For example, a tritiated compound can be prepared by introducing tritium into the particular compound, for example, by catalytic dehalogenation with tritium. This preparation may include reacting a suitably halogen-substituted precursor of the compound with tritium gas in the presence of a suitable catalyst, for example, Pd/C, in the presence or absence of a base. Other suitable methods for preparing tritiated compounds can be found in Filer, *Isotopes in the Physical and Biomedical Sciences, Vol. 1, Labeled Compounds (Part A)*, Chapter 6 (1987). $^{14}C$-labeled compounds can be prepared by employing starting materials having a $^{14}C$ carbon.

Some of the compounds disclosed herein may contain one or more asymmetric centers and may thus give rise to enantiomers, diastereomers, and other stereoisomeric forms. The present disclosure is meant to encompass the use of all such possible forms, as well as their racemic and resolved forms and mixtures thereof. The individual enantiomers can be separated according to methods known in the art in view of the present disclosure. When the compounds described herein contain olefinic double bonds or other centers of geometric asymmetry, and unless specified otherwise, it is intended that they include both E and Z geometric isomers. All tautomers are intended to be encompassed by the present disclosure as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "resolution" refers to the separation or concentration or depletion of one of the two enantiomeric forms of a molecule.

The terms "a" and "an" refer to one or more.

The term "treat," "treating" or "treatment" is meant to encompass administering to a subject a compound of the present disclosure for the purposes of amelioration or cure, including preemptive and palliative treatment. In one embodiment, the term "treat," "treating" or "treatment" is meant to encompass administering to a subject a compound of the present disclosure for the purposes of amelioration or cure.

The term "about," as used herein in connection with a measured quantity, refers to the normal variations in that measured quantity, as expected by the skilled artisan making the measurement and exercising a level of care commensurate with the objective of measurement and the precision of the measuring equipment.

The present disclosure encompasses the preparation and use of salts of the compounds disclosed herein, including non-toxic pharmaceutically acceptable salts. Examples of pharmaceutically acceptable addition salts include inorganic and organic acid addition salts and basic salts. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, asparginate, glutamate and the like.

Acid addition salts can be formed by mixing a solution of the particular compound with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, or the like. Basic salts can be formed by mixing a solution of the compound of the present disclosure with a solution of a pharmaceutically acceptable non-toxic base such as sodium hydroxide, potassium hydroxide, choline hydroxide, sodium carbonate and the like.

The present disclosure encompasses the preparation and use of solvates of compounds used in the invention. Solvates typically do not significantly alter the physiological activity or toxicity of the compounds, and as such may function as pharmacological equivalents. The term "solvate" as used herein is a combination, physical association and/or solvation of a compound of the present disclosure with a solvent molecule such as, e.g. a disolvate, monosolvate or hemisolvate, where the ratio of solvent molecule to compound of the present disclosure is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds disclosed herein can be present as solvated forms with a pharmaceutically acceptable solvent, such as water, methanol, ethanol, and the like, and it is intended that the disclosure includes both solvated and unsolvated forms of these compounds. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al, *J. Pharmaceut. Sci.*, 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.*, 5(1):Article 12 (2004), and A. L. Bingham et al., *Chem. Commun.* 603-604 (2001). A typical, non-limiting, process of preparing a solvate would involve dissolving a compound disclosed herein a desired solvent (organic, water, or a mixture thereof) at temperatures above 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

DETAILED DESCRIPTION

Figure 1A:
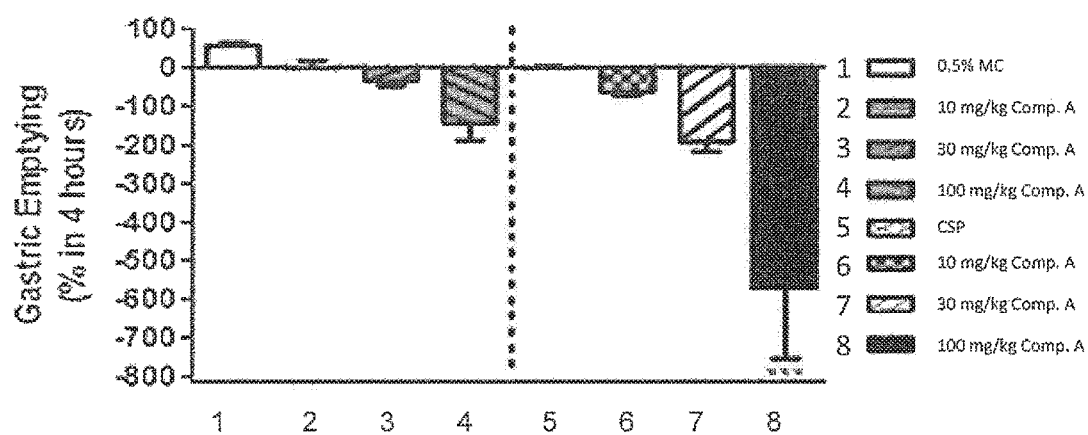
FIGS. 1A-1B are graphical depictions of the effect of dosing on the percentage of gastric emptying and stomach weights, respectively, after oral administration of Compound A in test animals in accordance with Example 1.

Abnormal gastric emptying can be a painful ailment for those who suffer from it. Therefore, it is important to provide an effective treatment. In some embodiments, the present invention discloses a method of decreasing gastric emptying comprising administering to a subject an effective amount of a sodium-channel blocker to decrease gastric emptying.

In some embodiments, the present invention discloses a method of treating gastric emptying by administering an effective amount of a sodium-channel blocker (such as a 4-N substituted pyramidine amides compound) including any pharmaceutically acceptable salts, solvates, or prodrugs thereof.

The type of gastric emptying being treated may be early rapid gastric emptying, late rapid gastric emptying, or both. The method may also be used in some embodiments where the subject is being prophylactically treated for gastric emptying. In other embodiments of the invention, the subject may be treated for a metabolic syndrome or for obesity.

In some embodiments, the method may be used to treat gastric emptying in subjects having type 1 diabetes mellitus, type 2 diabetes mellitus, scleroderma, or migraine episodes. In some embodiments, the method may control post-prandial rise in blood glucose, a symptom observed in diabetic patients. In some embodiments, the method may control drops in blood pressure, a symptom associated with gastric emptying. In some embodiments, the method may control cyclic vomiting syndrome, short bowl syndrome, and/or pouch emptying in Roux-en-Y Gastric Bypass (RYGB).

In some embodiments, the method may exhibit an increase in stomach acidity after administration of the sodium-channel blocker or any pharmaceutically acceptable salts, solvates, or prodrugs thereof.

In other embodiments, the method may be used to treat the subject for symptoms including, but not limited to, cramping, pain, abdominal pain, nausea, vomiting, diarrhea, sweating, flushing, light-headedness, rapid or irregular heartbeat, bloating, dizziness, fatigue, concentration difficulties, anxiety, sitophobia, weight gain, malnutrition, shortness of breath, low blood pressure, weakness, reduced food intake, increased food intake or hypoglycemia. In some embodiments, the method may be used to induce weight loss or assist with weight management.

In certain embodiments, the subject may have previously undergone gastric surgery, esophageal surgery, gastrectomy, gastroenterostomy, vagotomy, fundoplication, esophagectomy, gastric bypass or bariatric surgery. In other embodiments, the method may be used where the subject has nerve damage, Zollinger-Ellison syndrome, diabetes mellitus, sclerodema, migraine episodes, post-prandial rise in blood glucose, societal burdens linked with gastric-emptying, cyclic vomiting syndrome, short bowl syndrome, impaired gastric accommodation or functional dyspepsia. In some embodiments, the present invention discloses a method of weight management using an effective amount of a sodium-channel blocker (such as a 4-N substituted pyrimidine amides compounds) including any pharmaceutically acceptable salts, solvates, or prodrugs thereof to increase weight loss. In other embodiments, the method of weight management may be used where the subject is being treated for a metabolic syndrome or obesity and/or where the subject is being treated for a symptom such as increased food intake or increased weight gain.

In certain embodiments, the route of administration of the sodium channel blocker may be, but is not limited to, oral, parenteral, subcutaneous, intravenous, intramuscular, intraperitoneal, transdermal, transmucosal, sublingual, buccal, gingival, rectal, subcutaneous, transpulmonary or topical. In some embodiments, administration may be subcutaneous. In other embodiments, administration may be oral.

In certain embodiments, the sodium-channel blocker may be in a dosage form which may be, but is not limited to, a tablet, troche, lozenge, powder, granule, hard or soft capsule, microparticle, buccal tablets, buccal strips, transdermal patch, liquid, solution, suspension or suppository.

In some embodiments, the dosage form may contain from about 0.01 mg to about 1,000 mg of the sodium-channel blocker. In other embodiments, the dosage form may contain from about 0.1 mg to about 750 mg or from about 1 mg to about 500 mg of the sodium-channel blocker.

In certain embodiments, administration of the sodium-channel blocker dosage is once daily. In other embodiments, administration of the sodium-blocker dosage may be twice daily, thrice daily, four times daily, about weekly, or about monthly. In one embodiment, the sodium channel blocker is formulated in a transdermal patch that is effective for at least 1, 2, 3, 4, 5, 6, or 7 days.

The sodium-channel blocker may be administered with at least one additional active agent. The additional active ingredient may be, but is not limited to, octreotide or a pharmaceutically acceptable salt thereof, such as octreotide acetate, cholestyramine or a pharmaceutically acceptable salt thereof, a proton pump inhibitor, an anti-diabetic agent (acarbose or a pharmaceutically acceptable salt thereof) and/or an active agent that mimics the action of somatostatin.

In some embodiments, the invention is directed to a method of preparing a pharmaceutical composition, comprising admixing a therapeutically effective amount of a sodium-channel blocker to treat, minimize or prevent gastric emptying (e.g., rapid gastric emptying) with a pharmaceutically acceptable carrier.

In other embodiments, the invention discloses a pharmaceutical composition comprising a sodium-channel blocker in a therapeutically effective amount to treat gastric emptying along with a pharmaceutically acceptable carrier.

In another embodiment, the invention is directed to the use of a sodium channel blocker in the manufacture of a medicament to treat, minimize or prevent gastric emptying (e.g., rapid gastric emptying).

The methods and compositions of the present invention can utilize any sodium channel blocker know in the art. For example, the sodium channel blocker can be any compound disclosed in WO2001/68612; WO2001/72714; WO2001/74779; WO2003/008398; WO2003/022285; WO2003076414; WO2004/011439; WO2008053352; WO2011158108; WO2012/007836; WO2012/035421; WO2012/004664; WO2012/046132; WO2012/085650; WO2013/030665; WO2013/064884; WO2013/072758; WO2013/136170; WO2014/016673; WO2014/135955 and WO2014/151393. The sodium channel blocker can also be any compound described in US20140296313; US20100240652; US20100267782 and US20090023740.

In some embodiments, the sodium channel blocker is a compound that contains a pyrimidine moiety or a pyrimidine amide moiety. In certain embodiments, the compound can be a 4-N substituted pyrimidine amide that inhibit gastric emptying and provide pain relief.

In one embodiment, the sodium channel blocker is a compound of Formula I or a pharmaceutically acceptable salt, solvate, or prodrug thereof:

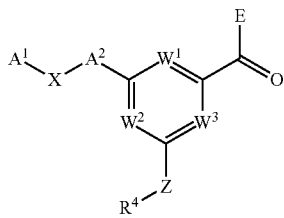

wherein:

Two of $W^1$, $W^2$, or $W^3$ are N and the remaining one is $CR^3$; wherein $R^3$ selected from the group consisting of: hydrogen; halo; nitro; cyano; hydroxy; amino; alkylamino; dialkylamino; haloalkyl; hydroxyalkyl; alkoxy; haloalkoxy; and alkoxyalkyl.

$A^1$ is selected from the group consisting of optionally substituted aryl; optionally substituted heteroaryl; optionally substituted cycloalkyl; optionally substituted heterocyclo; and aralkyl;

X is selected from the group consisting of —O—; —S—; —SO—; —SO$_2$—; —(CR$^{7a}$R$^{7b}$)$_m$—; —NR$^8$—; —SO$_2$NR$^9$—; and —NR$^9$SO$_2$—;

Each $R^{7a}$ and $R^{7b}$, independently, is selected from the group consisting of hydrogen; halo; and alkyl; or Each $R^{7a}$ and $R^{7b}$ taken together with the carbon atom to which they are attached form a 3- to 8-membered optionally substituted cycloalkyl or a 3- to 8-membered optionally substituted heterocyclo; m is 0, 1, 2, or 3; $R^8$ and $R^9$ are independently selected from the group consisting of hydrogen and alkyl; $A^2$ is selected from the group consisting of optionally substituted aryl; optionally substituted heteroaryl; optionally substituted heterocyclo; and optionally substituted cycloalkyl; or $A^2$ is absent;

E is selected from the group consisting of hydroxy; alkoxy; and —NR$^1$R$^2$; wherein R$^1$ is selected from the group consisting of: hydrogen; alkyl; aralkyl; (heterocyclo)alkyl; (heteroaryl)alkyl; (amino)alkyl; (alkylamino)alkyl; (dialkylamino)alkyl; (carboxamido)alkyl; (cyano)alkyl; alkoxyalkyl; hydroxyalkyl; and heteroalkyl; R$^2$ is selected from the group consisting of hydrogen and alkyl; or R$^1$ and R$^2$ taken together with the nitrogen atom to which they are attached form a 3- to 8-membered optionally substituted heterocyclo;

Z is selected from the group consisting of —NR$^5$— and —O—; wherein R$^5$ is selected from the group consisting of: hydrogen; alkyl; hydroxyalkyl; and alkylsulfonyl; and R$^4$ is selected from the group consisting of

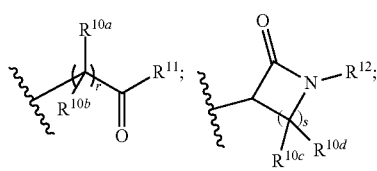

hydroxyalkyl; hydroxy(cycloalkyl)alkyl; and (heterocyclo)alkyl; or wherein R$^4$ and R$^5$ taken together with the nitrogen atom to which they are attached form a 3- to 8-membered optionally substituted heterocyclo;

Each $R^{10a}$, $R^{10b}$, $R^{10c}$, and $R^{10d}$ is independently selected from the group consisting of: hydrogen; hydroxy; optionally substituted alkyl; aralkyl; (heterocyclo)alkyl; (heteroaryl)alkyl; (amino)alkyl; (alkylamino)alkyl; (dialkylamino)alkyl; (carboxamido)alkyl; (cyano)alkyl; alkoxyalkyl; hydroxyalkyl; heteroalkyl; optionally substituted cycloalkyl; optionally substituted aryl; optionally substituted heterocyclo; and optionally substituted heteroaryl; or $R^{10a}$ and $R^{10b}$ taken together with the carbon atom to which they are attached form a 3- to 8-membered optionally substituted cycloalkyl or a 3- to 8-membered optionally substituted heterocyclo;

r and s are independently 1, 2, or 3;

$R^{11}$ is selected from the group consisting of: hydroxy; alkoxy; and —NR$^{1a}$R$^{2a}$;

$R^{1a}$ is selected from the group consisting of: hydrogen; alkyl; aralkyl; (heterocyclo)alkyl; (heteroaryl)alkyl; (amino)alkyl; (alkylamino)alkyl; (dialkylamino)alkyl; (carboxamido)alkyl; (cyano)alkyl; alkoxyalkyl; hydroxyalkyl; and heteroalkyl;

$R^{2a}$ is selected from the group consisting of hydrogen and alkyl; or $R^{1a}$ and $R^{2a}$ taken together with the nitrogen atom to which they are attached form a 3- to 8-membered optionally substituted heterocyclo;

$R^{12}$ is selected from the group consisting of hydrogen; optionally substituted alkyl; (amino)alkyl; (alkylamino)alkyl; (dialkylamino)alkyl; (carboxamido)alkyl; (cyano)alkyl; alkoxyalkyl; hydroxyalkyl; and heteroalkyl.

In one embodiment, the compound of Formula I (Compound A) is the following compound or a pharmaceutically acceptable salt, solvate, or prodrug thereof:

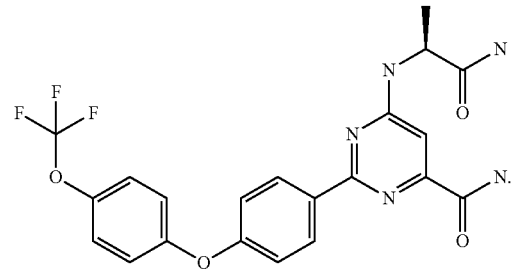

In one embodiment, the sodium channel blocker is a compound of Formula II or a pharmaceutically acceptable salt, solvate, or prodrug thereof:

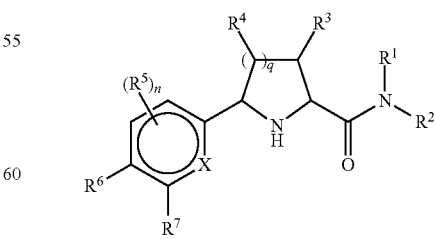

wherein

R$^1$ and R$^2$ are independently hydrogen, (C$_{1-6}$)alkyl or (C$_{3-6}$)cycloalkyl(C$_{1-6}$)alkyl; or R$^1$ and R$^2$, together with the nitrogen to which they are attached, may form an unsubstituted 3-, 4-, 5- or 6-membered saturated ring;

q is 1 or 2;

$R^3$ and $R^4$ are hydrogen; or when q is 1, $R^3$ and $R^4$, together with the interconnecting atoms, may form a cyclopropane ring;

X is carbon or nitrogen;

n is 0, 1 or 2, wherein when present each $R^5$ is independently selected from the list consisting of $(C_{1-3})$alkyl, halogen, cyano, halo$(C_{1-3})$alkyl, hydroxy, $(C_{1-3})$alkoxy and $(C_{1-3})$haloalkoxy; and Either $R^6$ or $R^7$ is —O—$R^8$ or —OCH$_2R^8$, wherein the other $R^6$ or $R^7$ is hydrogen or $R^5$ as defined hereinbefore; and wherein $R^8$ is either a phenyl ring or a 5- or 6-membered aromatic heterocyclic ring (independently containing one or more nitrogen, sulphur or oxygen atoms) wherein either the phenyl ring or the heterocyclic ring is optionally substituted by one or more groups independently selected from the list consisting of $(C_{1-3})$alkyl, halogen, cyano, halo$(C_{1-3})$alkyl, hydroxy, $(C_{1-3})$alkoxy and $(C_{1-3})$haloalkoxy.

In one embodiment, the compound of Formula II (Compound C) is the following compound or a pharmaceutically acceptable salt, solvate, or prodrug thereof:

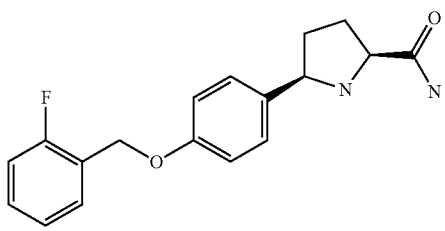 [SMILES: NC(=O)[C@@H]1CC[C@H](c2ccc(OCc3ccccc3F)cc2)N1]

In one embodiment, the sodium channel blocker is a compound of Formula III or a pharmaceutically acceptable salt, solvate, or prodrug thereof:

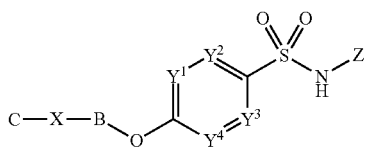

wherein Z is Het$^2$, optionally substituted on a ring carbon atom with one or more substituents selected from the group consisting of halo, cyano, $(C_{1-4})$alkyl, halo$(C_{1-4})$alkyl, $(C_{1-4})$alkoxy, halo$(C_{1-4})$alkoxy, $(C_{3-8})$cycloalkyl, [$(C_{3-8})$cycloalkyl]$(C_{1-4})$alkyl, $(C_{1-4})$alkyl-S—, amino, $(C_{1-4})$alkylamino, di$(C_{1-4})$alkylamino, amino$(C_{1-4})$alkyl, [$(C_{1-4})$alkylamino]$(C_{1-4})$alkyl, and [di$(C_{1-4})$alkylamino]$(C_{1-4})$alkyl; and/or Het$^2$ is optionally substituted on a ring nitrogen atom with $(C_{1-4})$alkyl, halo$(C_{1-4})$alkyl and $(C_{3-8})$cycloalkyl; with the proviso that Z is not tetrazolyl;

$Y^1$, $Y^2$, $Y^3$ and $Y^4$ are each independently CH, CR$^1$ or N, provided that no more than two of $Y^1$, $Y^2$, $Y^3$ and $Y^4$ are N;

Each $R^1$ is independently selected from the group consisting of halo, cyano, amino, hydroxy, $(C_{1-4})$alkyl, halo$(C_{1-4})$alkyl, hydroxy$(C_{1-4})$alkyl, $(C_{1-4})$alkoxy, halo$(C_{1-4})$alkoxy, $(C_{1-4})$alkoxy$(C_{1-4})$alkyl, —C(O)H, —C(O)$(C_{1-4})$alkyl, and —C(O)N(R$^2$)$_2$;

Each $R^2$ is independently hydrogen, $(C_{1-4})$alkyl, halo$(C_{1-4})$alkyl, hydroxy$(C_{1-4})$alkyl, or $(C_{3-6})$cycloalkyl; or, where a nitrogen is substituted with two $R^2$ groups, each independently selected from $(C_{1-4})$alkyl, halo$(C_{1-4})$alkyl, or hydroxy$(C_{1-4})$alkyl, or they may be taken together with the N atom to which they are attached to form a 4- to 6-membered ring which, when so formed, may also optionally be substituted with hydrogen, alkyl, halo, hydroxy, hydroxyalkyl or haloalkyl;

B is phenyl or Het$^2$. When B is Het$^2$ it is attached to the oxy linker at a ring carbon atom, and is optionally further substituted on a ring carbon atom with one or more substituents selected from the group consisting of halo, cyano, hydroxy, $(C_{1-4})$alkyl, halo$(C_{1-4})$alkyl, $(C_{1-4})$alkoxy, halo$(C_{1-4})$alkoxy, cyano$(C_{1-4})$alkyl, amino, $(C_{1-4}$ alkylamino, di$(C_{1-4})$alkylamino, amino$(C_{1-4})$alkyl, [$(C_{1-4})$alkylamino]$(C_{1-4})$alkyl, [di$(C_{1-4})$alkylamino]$(C_{1-4})$alkyl, trifluoromethylthio, hydroxy$(C_{1-4})$alkyl, $(C_{1-4})$alkoxy$(C_{1-4})$alkyl, —C(O)R$^2$, —C(O)OR$^2$, —OC(O)R$^2$, —C(O)—N(R$^2$)$_2$, —CH$_2$—C(O)R$^2$, —CH$_2$—C(O)OR$^2$, —CH2-OC(O)R$^2$, —CH$_2$—C(O)—N(R$^2$)$_2$, S(O)$_2$R$^2$, S(O)$_2$N(R$^2$)$_2$, $(C_{3-8})$cycloalkyl, and [$(C_{3-8})$cycloalkyl]$(C_{1-4})$alkyl; and/or Het$^2$ is optionally substituted on a ring nitrogen atom with a substituent selected from the group consisting of $(C_{1-4})$ alkyl, halo$(C_{1-4})$alkyl, hydroxy$(C_{1-4}$ alkyl, $(C_{1-4})$alkoxy $(C_{1-4})$alkyl, amino$(C_{1-4})$alkyl, [$(C_{1-4})$alkylamino]$(C_{1-4})$ alkyl, [di$(C_{1-4})$alkylamino]$(C_{1-4})$alkyl, —CH$_2$—C(O)R$^2$, —CH$_2$—C(O)OR$^2$, —CH$_2$—C(O)—N(R$^2$)$_2$, S(O)$_2$R$^2$, and S(O)$_2$N(R$^2$)$_2$;

X is either absent, or selected from —O—, methylene, ethylene, methylene-O—, or —O-methylene;

C is selected from $(C_{3-8})$cycloalkyl, Het$^1$, phenyl, or Het$^2$, each optionally substituted on a ring carbon atom with one or more substituents selected from the group consisting of halo, cyano, hydroxy, $(C_{1-4})$alkyl, halo$(C_{1-4})$alkyl, $(C_{1-4})$ alkoxy, halo$(C_{1-4})$alkoxy, N(R$^2$)$_2$, (R$^2$)$_2$N(C$_{1-4}$)alkyl, trifluoromethylthio, hydroxy$(C_{1-4}$ alkyl, $(C_{1-4})$alkoxy$(C_{1-4})$ alkyl, —C(O)R$^2$, —C(O)OR$^2$, —OC(O)R$^2$, —C(O)—N (R$^2$)$_2$, —CH$_2$—C(O)R$^2$, —CH$^2$—C(O)OR$^2$, —CH$_2$—OC (O)R$^2$, —CH$_2$—C(O)—N(R$^2$)$_2$, S(O)$_2$R$^2$, S(O)$_2$N(R$^2$)$_2$, [$(C_{3-8})$cycloalkyl]$(C_{1-4})$alkyl, $(C_{3-8})$cycloalkoxy, $(C_{3-8})$cycloalkylamino, [$(C_{3-8})$cycloalkylamino]$(C_{1-4})$alkyl, [$(C_{3-8})$ cycloalkyl]$(C_{1-4})$alkylamino, {[$(C_{3-8})$cycloalkyl]$(C_{1-4})$alkylamino}$(C_{1-4})$alkyl, [$(C_{3-8})$cycloalkyl]$(C_{1-4})$alkoxy and D (defined below); and/or Het$^2$ is optionally substituted on a ring nitrogen atom with a substituent selected from the group consisting of hydroxy, $(C_{1-4})$alkyl, halo$(C_{1-4})$alkyl, amino$(C_{1-4})$alkyl, [$(C_{1-4})$alkylamino]$(C_{1-4})$alkyl, [di$(C_{1-4})$alkylamino]$(C_{1-4})$alkyl, hydroxy$(C_{1-4})$alkyl, $(C_{1-4})$alkoxy$(C_1$-$C_4)$alkyl, —C(O)R$^2$, —C(O)OR$^2$, —CH$_2$—C(O)R$^2$, —CH$_2$—C(O)OR$^2$, —CH$_2$—C(O)—N(R$^2$)$_2$, S(O)$_2$R$^2$, and S(O)$_2$N(R$^2$)$_2$ and D (defined below); with the proviso that C is not 3,5-dioxo-4,5-dihydro-$^3$H-[1,2,4]triazin-2-yl;

D is phenyl, benzyl, $(C_{3-8})$cycloalkyl, or Het$^1$, each optionally substituted on a carbon atom with one or more substituents independently selected from the group consisting of halo, cyano, hydroxy, $(C_{1-4})$alkyl, halo$(C_{1-4})$alkyl, $(C_{1-4})$alkoxy, halo$(C_{1-4})$alkoxy, amino, $(C_{1-4}$alkylamino, di$(C_{1-4})$alkylamino, amino$(C_{1-4})$alkyl, [$(C_{1-4})$alkylamino] $(C_{1-4})$alkyl, [di$(C_{1-4})$alkylamino]$(C_1$-$C_4)$alkyl, trifluoromethylthio, hydroxy$(C_1$-$C_4)$alkyl, $(C_1$-$C_4)$alkoxy$(C_1$-$C_4)$ alkyl, —C(O)R$^2$, —C(O)OR$^2$, —OC(O)R$^2$, —C(O)—N (R$^2$)$_2$, —CH$_2$—C(O)R$^2$, —CH$_2$—C(O)OR$^2$, —CH$_2$—OC (O)R$^2$, —CH$_2$—C(O)—N(R$^2$)$_2$, S(O)$_2$R$^2$, and S(O)$_2$N(R$^2$)$_2$;

Het$^1$ is a 3- to 8-membered, saturated or partially unsaturated monocyclic heterocyclic group comprising one or two or three ring members selected from —NR$^3$—, —O—, —C(O)— and —S(O)$_p$—;

$R^3$ is either the point of attachment to X or C to give

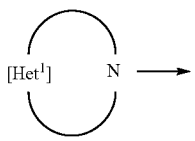

or $R^3$ is selected from the group consisting of hydrogen, $(C_{1-4})$alkyl, halo$(C_{1-4})$alkyl, hydroxy$(C_{1-4})$alkyl, $(C_{1-4})$alkoxy$(C_{1-4})$alkyl, —C(O) $(C_{1-4})$alkyl, —C(O)O$(C_{1-4})$alkyl, $CH_2$—C(O)O$(C_{1-4})$alkyl, —$CH_2$—C(O)—N$((C_{1-4})$alkyl$)_2$, $S(O)_2R^2$, $S(O)_2N(R^2)_2$ and $(C_{3-8})$cycloalkyl;

p is 0, 1 or 2; and $Het^2$ is a 5- or 6-membered aromatic heterocyclic group comprising either (a) one to four nitrogen atoms, (b) one oxygen or one sulfur atom, or (c) one oxygen atom or 1 sulfur atom and 1 or 2 nitrogen atoms;

or a tautomer thereof, or a pharmaceutically acceptable salt or solvate of the compound of formula (I), or its tautomer;

In one embodiment, the compound of Formula III (Compound D) is the following compound or a pharmaceutically acceptable salt, solvate, or prodrug thereof:

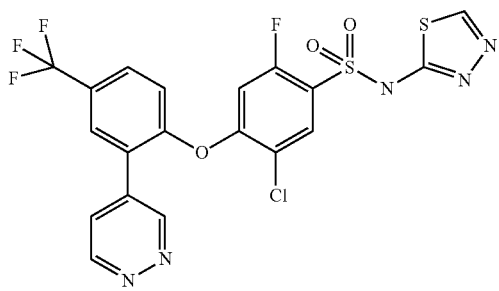 [SMILES: O=S(=O)(Nc1nncs1)c1cc(Cl)c(Oc2ccc(C(F)(F)F)cc2-c2ccnnc2)cc1F]

In one embodiment, the sodium channel blocker is a compound of Formula IV or a pharmaceutically acceptable salt, solvate, or prodrug thereof:

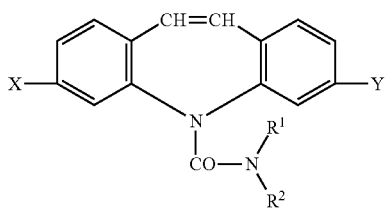

wherein X and Y represent hydrogen or halogen atoms, a) and $R^1$ and $R^2$ represent hydrogen or an alkyl radical; and b) alkyl radicals which can be bound to each other either directly or via an oxygen atom.

In one embodiment, the compound of Formula IV (Compound B) is the following compound or a pharmaceutically acceptable salt, solvate, or prodrug thereof:

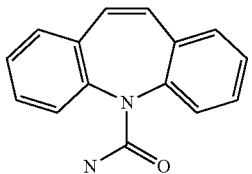 [SMILES: NC(=O)N1c2ccccc2C=Cc2ccccc21]

Pharmaceutical Compositions

The compounds disclosed herein can be administered to a mammal in the form of a raw chemical without any other components present. Compounds can also be administered to a mammal as part of a pharmaceutical composition containing the compound combined with a suitable pharmaceutically acceptable carrier. Such a carrier can be selected from pharmaceutically acceptable excipients and auxiliaries.

Pharmaceutical compositions within the scope of the present disclosure include all compositions where a compound is combined with one or more pharmaceutically acceptable carriers. In one embodiment, the compound is present in the composition in an amount that is effective to achieve its intended therapeutic purpose. While individual needs may vary, a determination of optimal ranges of effective amounts of each compound is within the skill of the art. Typically, a compound can be administered to a mammal, e.g., a human, orally at a dose of from about 0.0025 to about 1500 mg per kg body weight of the mammal, or an equivalent amount of a pharmaceutically acceptable salt, prodrug, or solvate thereof, per day to treat the particular disorder. In one embodiment, the oral dose of a compound administered to a mammal is from about 0.0025 to about 50 mg per kg body weight of the mammal, or an equivalent amount of the pharmaceutically acceptable salt, prodrug, or solvate thereof. An intramuscular dose may be about one-half of the oral dose.

A unit oral dose may comprise from about 0.01 mg to about 1 g of the compound, e.g., about 0.01 mg to about 500 mg, about 0.01 mg to about 250 mg, about 0.01 mg to about 100 mg, about 0.01 mg to about 50 mg, e.g., about 0.1 mg to about 10 mg, of the compound. The unit dose can be administered one or more times daily, e.g., as one or more tablets or capsules, each containing from about 0.01 mg to about 1 g of the compound, or an equivalent amount of a pharmaceutically acceptable salt, prodrug or solvate thereof.

A pharmaceutical composition of the present disclosure can be administered to any animal that may experience the beneficial effects of a compound. Foremost among such animals are mammals, e.g., humans and companion animals, although the disclosure is not intended to be so limited.

A pharmaceutical composition of the present disclosure can be administered by any means that achieves its intended purpose. For example, administration can be by the oral, parenteral, subcutaneous, intravenous, intramuscular, intraperitoneal, transdermal, intranasal, transmucosal, rectal, intravaginal or buccal route, or by inhalation. The dosage administered and route of administration will vary, depending upon the circumstances of the particular subject, accounting for, e.g., age, gender, health, and weight of the recipient, condition or disorder to be treated, kind of concurrent treatment, if any, frequency of treatment, and the nature of the effect desired.

In one embodiment, a pharmaceutical composition of the present disclosure can be administered orally and is formulated into tablets, dragees, capsules or an oral liquid preparation. In one embodiment, the oral formulation comprises extruded multiparticulates comprising the compound.

Alternatively, a pharmaceutical composition of the present disclosure can be administered rectally, and is formulated in suppositories.

Alternatively, a pharmaceutical composition of the present disclosure can be administered by injection.

Alternatively, a pharmaceutical composition of the present disclosure can be administered transdermally.

Alternatively, a pharmaceutical composition of the present disclosure can be administered by inhalation, intranasal or transmucosal administration.

Alternatively, a pharmaceutical composition of the present disclosure can be administered by the intravaginal route.

A pharmaceutical composition of the present disclosure can contain from about 0.01 to 99 percent by weight, and preferably from about 0.25 to 75 percent by weight, of active compound(s).

A method of the present disclosure, such as a method for treating gastric disorders in an animal in need thereof, can further comprise administering a second therapeutic agent to the animal in combination with a compound from the method. In one embodiment, the other therapeutic agent is administered in an effective amount.

Effective amounts of the other therapeutic agents are known to those skilled in the art. However, it is well within the skilled artisan's purview to determine the other therapeutic agent's optimal effective-amount range.

Compounds used in the invention (i.e., the first therapeutic agent) and the second therapeutic agent can act additively or, in one embodiment, synergistically. Alternatively, the second therapeutic agent can be used to treat a disorder or condition that is different from the disorder or condition for which the first therapeutic agent is being administered, and which disorder or condition may or may not be a condition or disorder as defined herein.

In one embodiment, a compound of the invention is administered concurrently with a second therapeutic agent via a single composition; for example, a single composition comprising both an effective amount of the compound disclosed herein and an effective amount of the second therapeutic agent can be administered. The present disclosure further provides a pharmaceutical composition comprising a combination of the compound disclosed herein, the second therapeutic agent, and a pharmaceutically acceptable carrier.

Alternatively, a first pharmaceutical composition comprising an effective amount of a compound disclosed herein and a separate second pharmaceutical composition comprising an effective amount of the second therapeutic agent can be concurrently administered.

In another embodiment, an effective amount of the compound disclosed herein is administered prior or subsequent to administration of an effective amount of the second therapeutic agent. In this embodiment, the compound disclosed herein is administered while the second therapeutic agent exerts its therapeutic effect, or the second therapeutic agent is administered while the compound disclosed herein exerts its therapeutic effect for treating a disorder or condition.

The second therapeutic agent can be an opioid agonist, a non-opioid analgesic, a non-steroidal anti-inflammatory agent, an anti-migraine agent, a Cox-II inhibitor, a β-adrenergic blocker, an anticonvulsant, an antidepressant, an anticancer agent, an agent for treating addictive disorder, an agent for treating Parkinson's disease and parkinsonism, an agent for treating anxiety, an agent for treating epilepsy, an agent for treating a seizure, an agent for treating a stroke, an agent for treating a pruritic condition, an agent for treating psychosis, an agent for treating ALS, an agent for treating a cognitive disorder, an agent for treating a migraine, an agent for treating vomiting, an agent for treating dyskinesia, or an agent for treating depression, or a mixture thereof.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof.

In certain embodiments, the opioid agonist is selected from codeine, hydromorphone, hydrocodone, oxycodone, dihydrocodeine, dihydromorphine, morphine, tramadol, oxymorphone, pharmaceutically acceptable salts thereof, and mixtures thereof.

Examples of useful non-opioid analgesics include non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, and pharmaceutically acceptable salts thereof, and mixtures thereof. Examples of other suitable non-opioid analgesics include the following, non-limiting, chemical classes of analgesic, antipyretic, nonsteroidal anti-inflammatory drugs: salicylic acid derivatives, including aspirin, sodium salicylate, choline magnesium trisalicylate, salsalate, diflunisal, salicylsalicylic acid, sulfasalazine, and olsalazin; para aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid, and meclofenamic acid; enolic acids, including oxicams (piroxicam, tenoxicam), and pyrazolidinediones (phenylbutazone, oxyphenthartazone); and alkanones, including nabumetone. For a more detailed description of the NSAIDs, see Paul A. Insel, *Analgesic Antipyretic and Antiinflammatory Agents and Drugs Employed in the Treatment of Gout*, in Goodman & Gilman's *The Pharmacological Basis of Therapeutics* 617-57 (Perry B. Molinhoff and Raymond W. Ruddon eds., 9th ed. 1996) and Glen R. Hanson, *Analgesic, Antipyretic and Anti Inflammatory Drugs* in Remington: The Science and Practice of Pharmacy Vol. II 1196-1221 (A. R. Gennaro ed. 19th ed. 1995) which are hereby incorporated by reference in their entireties. Suitable Cox-II inhibitors and 5-lipoxygenase inhibitors, as well as combinations thereof, are described in U.S. Pat. No. 6,136,839, which is hereby incorporated by reference in its entirety. Examples of useful Cox II inhibitors include, but are not limited to, rofecoxib, and celecoxib.

Examples of useful antimigraine agents include, but are not limited to, alpiropride, bromocriptine, dihydroergotamine, dolasetron, ergocornine, ergocorninine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, and mixtures thereof.

Examples of useful β-adrenergic blockers include, but are not limited to, acebutolol, alprenolol, amosulabol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol, indenolol, labetalol, levobunolol, mepindolol, metipranolol, metoprolol, moprolol, nadolol, nadoxolol, nebivalol, nifenalol, nipradilol, oxprenolol, penbutolol, pindolol, practolol, pronethalol, propranolol, sotalol, sulfinalol, talinolol, tertatolol, tilisolol, timolol, toliprolol, and xibenolol.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenytoin, mephobarbital, metharbital, methetoin, methsuximide, 5-methyl-5-(3-phenanthryl)-hydantoin, 3-methyl-5-phenylhydantoin, narcobarbital, nimetazepam, nitrazepam, oxcarbazepine, paramethadione, phenacemide, phenetharbital, pheneturide, phenobarbital, phensuximide, phenylmethylbarbituric acid, phenytoin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, and zonisamide.

Examples of useful antidepressants include, but are not limited to, binedaline, caroxazone, citalopram, (S)-citalopram, dimethazan, fencamine, indalpine, indeloxazine hydrocholoride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

Examples of useful anticancer agents include, but are not limited to, acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, and cisplatin.

Therapeutic agents useful for treating an addictive disorder include, but are not limited to, methadone, desipramine, amantadine, fluoxetine, buprenorphine, an opiate agonist, 3-phenoxypyridine, or a serotonin antagonist.

Examples of useful therapeutic agents for treating Parkinson's disease and parkinsonism include, but are not limited to, carbidopa/levodopa, pergolide, bromocriptine, ropinirole, pramipexole, entacapone, tolcapone, selegiline, amantadine, and trihexyphenidyl hydrochloride.

Examples of useful therapeutic agents for treating anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsapirone, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; and propanediol carbamates, such as meprobamate and tybamate.

Examples of useful therapeutic agents for treating epilepsy or seizure include, but are not limited to, carbamazepine, ethosuximide, gabapentin, lamotrigine, phenobarbital, phenytoin, primidone, valproic acid, trimethadione, benzodiazepines, gamma-vinyl GABA, acetazolamide, and felbamate.

Examples of useful therapeutic agents for treating stroke include, but are not limited to, anticoagulants such as heparin, agents that break up clots such as streptokinase or tissue plasminogen activator, agents that reduce swelling such as mannitol or corticosteroids, and acetylsalicylic acid.

Examples of useful therapeutic agents for treating a pruritic condition include, but are not limited to, naltrexone; nalmefene; danazol; tricyclics such as amitriptyline, imipramine, and doxepin; antidepressants such as those given below; menthol; camphor; phenol; pramoxine; capsaicin; tar; steroids; and antihistamines.

Examples of useful therapeutic agents for treating psychosis include, but are not limited to, phenothiazines such as chlorpromazine hydrochloride, mesoridazine besylate, and thoridazine hydrochloride; thioxanthenes such as chloroprothixene and thiothixene hydrochloride; clozapine; risperidone; olanzapine; quetiapine; quetiapine fumarate; haloperidol; haloperidol decanoate; loxapine succinate; molindone hydrochloride; pimozide; and ziprasidone.

Examples of useful therapeutic agents for treating ALS include, but are not limited to, baclofen, neurotrophic factors, riluzole, tizanidine, benzodiazepines such as clonazepan and dantrolene.

Examples of useful therapeutic agents for treating cognitive disorders include, but are not limited to, agents for treating dementia such as tacrine; donepezil; ibuprofen; antipsychotic drugs such as thioridazine and haloperidol; and antidepressant drugs such as those given below.

Examples of useful therapeutic agents for treating a migraine include, but are not limited to, sumatriptan; methysergide; ergotamine; caffeine; and beta-blockers such as propranolol, verapamil, and divalproex.

Examples of useful therapeutic agents for treating vomiting include, but are not limited to, 5-HT3 receptor antagonists such as ondansetron, dolasetron, granisetron, and tropisetron; dopamine receptor antagonists such as prochlorperazine, thiethylperazine, chlorpromazine, metoclopramide, and domperidone; glucocorticoids such as dexamethasone; and benzodiazepines such as lorazepam and alprazolam.

Examples of useful therapeutic agents for treating dyskinesia include, but are not limited to, reserpine and tetrabenazine.

Examples of useful therapeutic agents for treating depression include, but are not limited to, tricyclic antidepressants such as amitryptyline, amoxapine, bupropion, clomipramine, desipramine, doxepin, imipramine, maprotiline, nefazadone, nortriptyline, protriptyline, trazodone, trimipramine, and venlafaxine; selective serotonin reuptake inhibitors such as citalopram, (S)-citalopram, fluoxetine, fluvoxamine, paroxetine, and setraline; monoamine oxidase inhibitors such as isocarboxazid, pargyline, phenelzine, and tranylcypromine; and psychostimulants such as dextroamphetamine and methylphenidate.

A pharmaceutical composition of the present disclosure is manufactured in a manner which itself will be known in view of the instant disclosure, for example, by means of conventional mixing, granulating, dragee-making, dissolving, extrusion, or lyophilizing processes. Thus, pharmaceutical compositions for oral use can be obtained by combining the active compound with solid excipients, optionally grinding the resulting mixture and processing the mixture of granules, after adding suitable auxiliaries, if desired or necessary, to obtain tablets or dragee cores.

Suitable excipients include fillers such as saccharides (for example, lactose, sucrose, mannitol or sorbitol), cellulose preparations, calcium phosphates (for example, tricalcium phosphate or calcium hydrogen phosphate), as well as binders such as starch paste (using, for example, maize starch, wheat starch, rice starch, or potato starch), gelatin, tragacanth, methyl cellulose, hydroxypropylmethylcellulose, sodium carboxymethylcellulose, and/or polyvinyl pyrrolidone. If desired, one or more disintegrating agents can be added, such as the above-mentioned starches and also carboxymethyl-starch, cross-linked polyvinyl pyrrolidone, agar, or alginic acid or a salt thereof, such as sodium alginate.

Auxiliaries are typically flow-regulating agents and lubricants such as, for example, silica, talc, stearic acid or salts thereof (e.g., magnesium stearate or calcium stearate), and polyethylene glycol. Dragee cores are provided with suitable coatings that are resistant to gastric juices. For this purpose, concentrated saccharide solutions can be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate can be used. Dye stuffs or pigments can be added to the tablets or dragee coatings, for example, for identification or in order to characterize combinations of active compound doses.

Examples of other pharmaceutical preparations that can be used orally include push-fit capsules made of gelatin, or soft, sealed capsules made of gelatin and a plasticizer such as glycerol or sorbitol. The push-fit capsules can contain a compound in the form of granules, which can be mixed with fillers such as lactose, binders such as starches, and/or lubricants such as talc or magnesium stearate and, optionally, stabilizers, or in the form of extruded multiparticulates. In soft capsules, the active compounds are preferably dissolved or suspended in suitable liquids, such as fatty oils or liquid paraffin. In addition, stabilizers can be added.

Possible pharmaceutical preparations for rectal administration include, for example, suppositories, which consist of a combination of one or more active compounds with a suppository base. Suitable suppository bases include natural and synthetic triglycerides, and paraffin hydrocarbons, among others. It is also possible to use gelatin rectal capsules consisting of a combination of active compound with a base material such as, for example, a liquid triglyceride, polyethylene glycol, or paraffin hydrocarbon.

Suitable formulations for parenteral administration include aqueous solutions of the active compound in a water-soluble form such as, for example, a water-soluble salt, alkaline solution, or acidic solution. Alternatively, a suspension of the active compound can be prepared as an oily suspension. Suitable lipophilic solvents or vehicles for such as suspension may include fatty oils (for example, sesame oil), synthetic fatty acid esters (for example, ethyl oleate), triglycerides, or a polyethylene glycol such as polyethylene glycol-400 (PEG-400). An aqueous suspension may contain one or more substances to increase the viscosity of the suspension, including, for example, sodium carboxymethyl cellulose, sorbitol, and/or dextran. The suspension may optionally contain stabilizers.

The following examples are illustrative, but not limiting, of the compounds, compositions, and methods of the present disclosure. Suitable modifications and adaptations of the variety of conditions and parameters normally encountered in clinical therapy and which are obvious to those skilled in the art in view of this disclosure are within the spirit and scope of the disclosure.

EXAMPLES

Materials and Methods

Materials

All compounds were administered either in 0.5% MC as free base equivalent p.o. in a volume of 5 mL/kg (rat) or 2 ml/kg (monkey) or in 25% hydroxy-betacyclodextran (HPBCD) as free base equivalent s.c. in a volume of 2 ml/kg or i.v in a volume of 1 ml/kg. For electrophysiology, dimethyl sulfoxide (DMSO) stocks of compounds were prepared with subsequent serial dilutions in a bath solution. The final concentration of DMSO did not exceed 0.3%, which by itself did not have any effect on Nav currents. tetrodotoxin was diluted in distilled water; in serial dilutions DMSO was added to match osmolality of solutions with test compounds.

Cells

The cell lines used were the human Nav1.5 cell line (hosted in Chinese Hamster Ovary background) and the human Nav1.7 cell line (hosted in Human Embryonic Kidney-293 cell background). For electrophysiology, cells were plated on 35 mm culture dishes pre-coated with poly-D-lysine in standard Dulbecco's modified eagle's culture media and incubated in a 5% $CO_2$ incubator at 37° C. Electrophysiological recordings were made from the cultured cells approximately 12-48 hours after plating.

Electrophysiology

On the day of experimentation, the 35 mm dish was placed on the stage of an inverted microscope and continuously perfused with fresh extracellular solution. A multichannel, gravity-driven micro-perfusion system was used to apply compounds directly to the cell under evaluation. This system consisted of a linear array of glass pipettes connected to a motorized horizontal translator. The outlet of this micro-perfusion system was positioned approximately 100 µm from the cell of interest. Sodium currents were recorded under voltage-clamp in the whole-cell configuration using Axopatch-200B amplifier (Molecular Devices, Sunnyvale, Calif.), 1322A A/D converter (Molecular Devices) and pClamp software (v. 8; Molecular Devices). Borosilicate glass pipettes had resistance values between 1.5 and 3.0 MOhm when filled with pipette solution. Series resistance (<5 MOhm) was compensated by 75-80%. Signals were sampled at 10-50 kHz and low pass filtered at 5-10 kHz. Recordings were terminated if the amplitude of max current was below 1 nA (to avoid significant contamination with endogenous Nav currents) or stable baseline could not be achieved either due to changes in leak current or if series resistance could not be optimized to be <5 MOhm or it was unstable over time. Sodium currents were elicited using a repetitive test pulse between 2 and 10 ms in duration from a specific holding voltage. The amplitude of the test pulse was determined on a cell-by-cell basis and was chosen to generate the maximal current amplitude. Test pulses were delivered every 10-20 seconds. To assess affinities of Nav channel inhibition for state-dependent blockers (Compound A and Compound C) a two holding voltages protocol was used. First, a cell was held at a very negative membrane voltage (−110 to −130 mV), where all the steady-state inactivation was removed and all channels were in resting state. Resting block is usually weak and requires application of compounds at concentrations of 3 µM and higher (Ilyin et al. (2005). "V102862 (Co 102862): a potent, broad-spectrum state-dependent blocker of mammalian voltage-gated sodium channels." *Br J Pharmacol* 144(6): 801-812; Ilyin et al. (2006) "Pharmacology of 2-[4-(4-chloro-2-fluorophenoxy)phenyl]-pyrimidine-4-carboxamide: a potent, broad-spectrum state-dependent sodium channel blocker for treating pain states." *J Pharmacol Exp Ther* 318(3): 1083-1093). When solubility of compounds limited use of multiple compound concentrations, the affinity of resting block was estimated from a fractional inhibition by a single high concentration according to a derivation of the Hill equation (Leuwer et al. (2004) "An improved model for the binding of lidocaine and structurally related local anaesthetics to fast-inactivated voltage-operated sodium channels, showing evidence of cooperativity." *Br J Pharmacol* 141(1): 47-54; Benjamin et al. (2006). "State-dependent compound inhibition of Nav1.2 sodium channels using the FLIPR Vm dye: on-target and off-target effects of diverse pharmacological agents." *J Biomol Screen* 11(1): 29-39).

$$Kr=(FR/(1-FR))*[test],$$

Where Kr=dissociation constant for inhibition of resting Nav channels, FR=steady state fractional peak current amplitude after compound application relative to maximum current amplitude during baseline (control solution application) and [test]=concentration of test compound. Then holding voltage was depolarized to a more positive level where a certain fraction of Nav channels transitioned into the inactivated state, avoiding greater than 30% of channels moving into inactivated state (h≥0.7). At this voltage the magnitude of inhibition of Nav currents was larger than at rest due to a higher affinity to the inactivated state of the channel. Single or multiple concentrations of compounds were applied to collect partial inhibition-concentration curves and the $IC_{50}$ was measured at the second holding voltage. Based on Kr, h and $IC_{50}$, the dissociation constant for inactivated channel Ki was calculated according to the equation (Kuo et al. (1994). "Slow binding of phenytoin to inactivated sodium channels in rat hippocampal neurons." *Mol Pharmacol* 46(4): 716-725).

$$IC_{50}=1/((h/Kr)+(1-h)/Ki),$$

where h is the fraction of the channels in resting state in the absence of compound.

For TTX, all the measurements were conducted at a negative holding voltage, since this toxin does not generally show state-dependent block of Nav channels. For the TTX-sensitive isoform (Nav1.7) multiple concentrations of TTX were used to collect individual inhibition-concentration curves in a cumulative manner and then pooled data from 3-4 determinations were averaged with data presented as mean values. For TTX-insensitive isoform (Nav1.5) a single high concentration of TTX (2-3 µM) was applied to the cells and the modified Hill equation (see above) used to calculate a single concentration point $IC_{50}$ (Kr) values. Data again are presented as mean values.

Solutions:

To record sodium currents, the pipette solution contained (in mM): CsF (140), NaCl (10), HEPES (10), EGTA (1); pH 7.3. The extracellular solution (Hank's Balanced Salt Solution; Invitrogen, Carlsbad, Calif.) contained (in mM): $CaCl_2$ (1.26), $MgCl_2\text{-}6H_2O$ (0.493), $MgSO_4\text{-}7H_2O$ (0.407), KCl (5.33), $KH_2PO_4$ (0.441), NaCl (137.93), $Na_2HPO4$ (0.338), glucose (5.56), and was supplemented with 10 mM HEPES (pH=7.4).

Animals

Male Sprague-Dawley rats (Harlan, Ind., USA), weighing 220-270 g were used. Rats had access to food and water ad libitum and were maintained on corn cob bedding under artificial lighting (12 h) between 7:00 a.m. and 7:00 µm. at a controlled ambient temperature of 21±3° C. and relative humidity of 30-80%. All experiments with rats used group numbers of 4-10 per group (see legends for additional detail). Animals were group assigned randomly and assessed without knowledge of drug treatments. Vagotomized animals were acquired from Charles River (Wilmington, Mass.) and were used 15 days post-vagotomy.

Studies in cynomolgous monkeys were conducted by Battelle (Columbus, Ohio). Eleven monkeys, seven males and four females that had been previously received, quarantined, and acclimated and were naïve (females), or had not been used on other studies for a minimum of 6 months (males), were utilized. Prior to use on study, monkeys were acclimated to chair restraint for up to 2 hours. Chair restraint was used to facilitate dose administration and blood collection. Animals were individually housed in stainless steel cages. Monkeys were offered a certified diet twice daily and had access to fresh water ad libitum. The animals also were supplemented with fresh fruits and/or fresh vegetables. Monkeys were fasted overnight prior to dose administration.

Observations for moribundity and mortality were performed on all animals twice daily throughout the duration of the study. Cage-side clinical observations were recorded for all animals prior to dose administration and at the times of blood collection.

Pharmacokinetics
Rats

Compound A (0.5-100 mg/kg) was administered either orally, subcutaneously or intravenously while carbamazepine (Compound B) and Compound C were administered orally (30 mg/kg). Blood was collected at 0, 1, 3, 5, 8, and 24 hours from the tail vein and sample preparation performed as previously described (Sullivan et al. (2007). "Pharmacological characterization of the muscarinic agonist (3R,4R)-3-(3-hexylsulfanyl-pyrazin-2-yloxy)-1-aza-bicyclo[2.2.1]heptane (WAY-132983) in in vitro and in vivo models of chronic pain." *J Pharmacol Exp Ther* 322(3): 1294-1304). Blood was collected in sodium heparin and plasma was obtained after centrifugation at 14000 rpm for 10 min at 4° C. An aliquot of the samples (50 μL) was extracted by protein precipitation and 150 μL of acetonitrile (containing 100 ng/ml warfarin as the internal standard) added. Samples obtained following subcutaneous dosing were spotted onto dry blood spot cards (details), dried at room temperature and a 3 mm punch extracted in methanol/formic acid, evaporated under positive pressure and reconstituted. In both cases the mixture was shaken for 2 min, centrifuged at 3500 rpm for 5 min, after which 100 μL of the supernatant was transferred, added to 100 μL water and assessed by Liquid Chromatography/Mass Spectrometry/Mass Spectrometry (PE Sciex API4000) with m/z transition of 462.1 to 417 (Compound A), 462.1 to 417 (carbamazepine), 462.1 to 417 (Compound C) and limits of quantification of 0.5 ng/ml.

Monkeys

Compound A (10-100 mg/kg) was administered orally to cynomolgus monkeys and blood specimens were collected prior to dose administration and at target time points of 0.5, 1, 3, 5, 8, and 24 hours post-dose administration. Blood was collected via the femoral vein into tubes containing tripotassium ethylene-diamine-tetraacetic acid (K3EDTA) as the anticoagulant. Whole blood was centrifuged to obtain plasma (9000×g for 10 minutes at 4° C.) which was transferred into labeled tubes and stored at −80° C. Plasma calibration standards, blanks, and study samples were processed by protein precipitation. To a 50 μL aliquot 150 μL of a 10 ng/mL solution of an internal standard and 150 μL of acetonitrile was added. The mixture was eluted using positive pressure and analyzed by liquid chromatography/mass spectrometry/mass spectrometry with m/z transition of 462-417. Compound A concentrations were calculated using area response ratios and a regression line constructed from the concentrations and peak area response ratios of the calibration standards. Samples that yielded Compound A concentrations higher than that of the highest calibration standards in their initial analyses were diluted and reanalyzed in a separate run. The lower limit of quantification (LLOQ) for the plasma method is approximately 0.5 ng/mL and the upper limit of quantification (ULOQ) is approximately 1000 ng/mL extracted from plasma using a 50-μL aliquot of sample.

Gastrointestinal Transit

Small intestinal transit was measured based on a known method which involved the oral administration of a charcoal meal (Gmerek et al. (1986). "Independent central and peripheral mediation of morphine-induced inhibition of gastrointestinal transit in rats." *J Pharmacol Exp Ther* 236(1): 8-13). Rats were fasted with free access to water for 18 hours. Test compound or vehicle was dosed prior to oral administration of a charcoal slurry containing activated charcoal, flour and water in a ratio of 1:2:7.5 (10 ml/kg orally). One hour after receiving the charcoal slurry, rats were euthanized by $CO_2$ asphyxiation. The stomach and GI tract was excised from each animal. Whole stomach weight was recorded and the length of the small intestine (cm) (stomach to cecum) and the distance (cm) to the leading edge of charcoal was measured. Small intestinal transit data are expressed as a percentage of the distance traveled (i.e. % small intestinal transit=(distance charcoal traveled)/(total length of small intestine (stomach to cecum)×100). Pretreatment times were determined on the basis of pharmacokinetic data (not shown) and were as follows: Compound A, 60 minutes, Compound C, 60 minutes; carbamazepine, 60 minutes. Morphine was administered with a pretreatment time of 30 mins based on previous experience.

Gastric Emptying

The gastric emptying of a test meal was determined with modifications of a known method (Martinez et al. (1998). "Central CRF inhibits gastric emptying of a nutrient solid meal in rats: the role of CRF2 receptors." *Am J Physiol* 274(5 Pt 1): G965-970). Rats were fasted overnight (16-18 hours) with free access to water. The next morning, compound was administered and animals were individually housed in bedding-free cages with pre-weighed food available ad libitum and access to water for 2 hours. The water and food were then removed and the remaining food was re-weighed. Gastric emptying of the ingested meal was assessed 4 hours later. Animals were euthanized by CO2 inhalation followed by thoracotomy. The abdominal cavity was opened, the pylorus and cardia were clamped and the stomach was removed. The excised stomach was weighed and then opened along the greater curvature, rinsed with tap water, lightly dried and re-weighed. The amount of food in the stomach (grams) was estimated based on the difference between the total weight of the stomach plus its contents and the weight of the stomach after the contents were removed. The meal ingested (food intake) was determined by the difference between pre- and post-feeding weight at the end of the 2 hour period. Gastric emptying during the 4 hour experiment is represented as:

$$\text{Gastric emptying} = [1-(\text{gastric content}/\text{food intake})] \times 100.$$

Gastric Secretion

Gastric section and acidity was assessed by direct measurement in fasted animals (Melo et al. (2006). "Effect of acid secretion blockade on acute gastric mucosal lesions induced by *Tityus serrulatus* scorpion toxin in anaesthetized rats." *Toxicon* 48(5): 543-549). Rats were fasted with free access to water for 24 hours on wire inserts without bedding. The next day, all rats were dosed orally with 0.5% MC (5 ml/kg) to remove any residual stomach contents and test compound or vehicle was administered. The animals were water deprived for 3 hours, anesthetized with isoflurane (5% in $O_2$), and a laparotomy was conducted followed by tight ligation of the pylorus and cardia. After ligation, the stomach was removed and the rat was immediately euthanized by decapitation. The stomach was opened along the greater curvature and gastric fluid collected into Eppendorf tubes and centrifuged (5 min at 10×1000 g). pH was determined by pipetting gastric fluid directly onto an indicator stick (Whatman, Panpeha Plus, pH0-14). Data are represented as the mean volume and mean pH.

Analysis of Results

Analysis of results. Data are shown as mean±SEM. $IC_{50}$ values were determined using Graph-Pad Prism (GraphPad Software Inc., San Diego, Calif., USA). Pharmacokinetic parameters were calculated by noncompartmental approaches usingWinNonlin Professional 4.1 (Pharsight, Mountain View, Calif., USA). Statistical significance was determined on untransformed data using a one-way (gastrointestinal transit, gastric emptying and gastric section), a two-way ANOVA (body-weight) or student's unpaired t-test (vagotomized animals) with Bonferonni's post-test (gastrointestinal transit, body weight and gastric secretion) or Dunnett's multiple comparison post-test (gastric emptying) using GraphPad Prism with across-group comparisons (all treatments to vehicle) being reported. Significant effects were analyzed further by subsequent least significant difference analysis. The level of significance was set at $P<0.05$.

Example 1

The Effect of Compound a on Gastric Emptying Following Oral Administration

Male, Sprague-Dawley rats (weighing between 229-264 g each and 4 rats per test group) were fasted overnight (19 hours). The rats were then orally administered 10 mg/kg, 30 mg/kg or 100 mg/kg of Compound A with a 0.5% MC or Capryol:Solutol:Polyethyleneglycol (CSP) vehicle or with a 0.5% MC or CSP vehicle alone. The rats were then placed in individual, bedding-free cages and allowed ad libitum access to pre-weighed food and water for two hours. The food and water were then removed and the food was reweighed. Gastric emptying was then assessed four hours later by euthanizing the rats and analyzing the stomach and stomach contents. Gastric emptying data were analyzed by a one-way ANOVA using a Bonferroni Multiple Comparisons Test, where ***$P<0.001$ compared to the appropriate vehicle. Data are represented as the means+the standard error of the means (S.E.M). % Gastric Emptying in 4 hours=(1−(gastric content/food intake))×100. Stomach weight data were analyzed by a one-way ANOVA using a Bonferroni Multiple Comparisons Test, where *$P<0.05$ and **$P<0.01$ compared to the appropriate vehicle. Data are represented as the means+S.E.M.

Figure 1B:
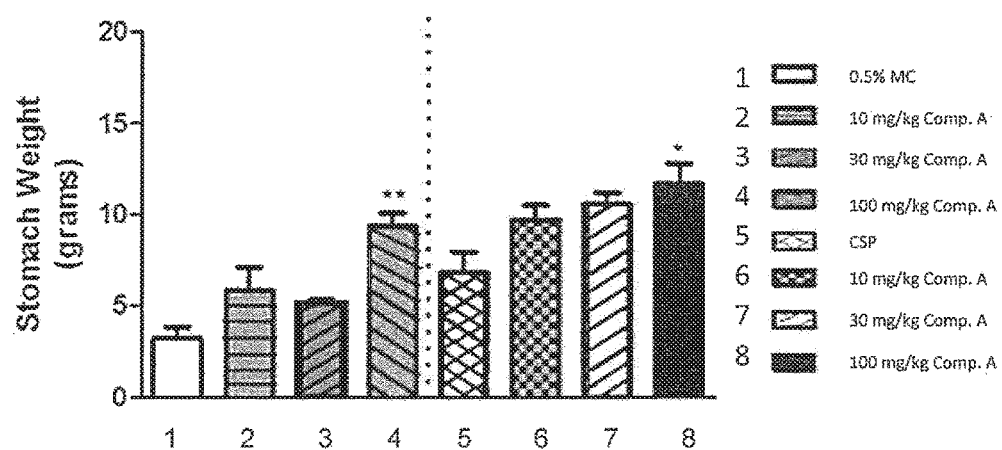

FIGS. 1A and 1B are graphical depictions of the effect of dosing and vehicle type on the percentage of gastric emptying and on the stomach weight of the test animals after oral administration of Compound A.

FIGS. 1A and 1B illustrate that increased dosing of Compound A is correlated with increased inhibition of gastric emptying and increased stomach weight. A greater inhibiting effect on gastric emptying and stomach weight increase was observed with a CSP vehicle as compared to a 0.5% MC vehicle.

Example 2

The Effect of Compound A on Gastric Emptying Following Subcutaneous and Oral Administration Male, CD1 mice (weighing between 30-36 g each and 6 mice per test group) were fasted overnight (19 hours). The mice then were subcutaneously administered 3 mg/kg of Compound A with a 25% HPBCD vehicle, a 25% HPBCD vehicle alone, orally administered 100 mg/kg of Compound A with a 0.5% MC vehicle, or a 0.5% MC vehicle alone. The mice were then placed in individual, bedding-free cages and allowed ad libitum access to pre-weighed food and water for two hours. The food and water were then removed and the food was reweighed. Gastric emptying was assessed four hours later by euthanizing the mice and analyzing the stomach and stomach contents. Data were analyzed using an unpaired t-test where *$P<0.05$ and ***$P<0.001$ and represented as the means+S.E.M. % Gastric Emptying in 4 hours=(1−(gastric content/food intake)×100). One mouse from the 100 mg/kg group was excluded from analysis since it did not consume any food and was more than two standard deviations from the mean.

Figure 2A:
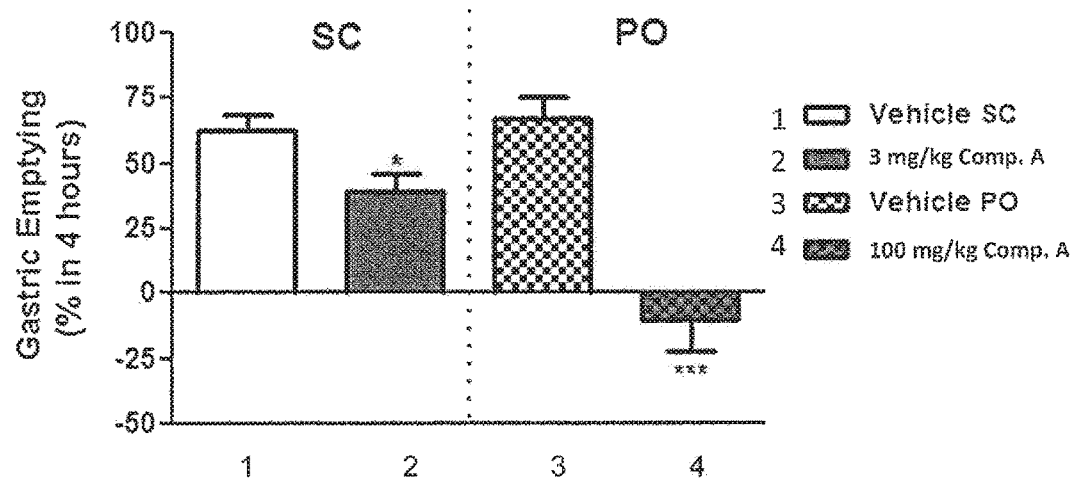
FIGS. 2A-2C are graphical depictions of the effect of dosing on the percentage of gastric emptying, stomach weights, and food intake, respectively, after subcutaneous administration of Compound A in test animals in accordance with Example 2.

FIG. 2A shows the effect of Compound A dosing on the percentage of gastric emptying. Both oral administration of Compound A with a 0.5% MC vehicle and subcutaneous administration of Compound A with a 25% HPBCD vehicle inhibit gastric emptying.

Figure 2B:
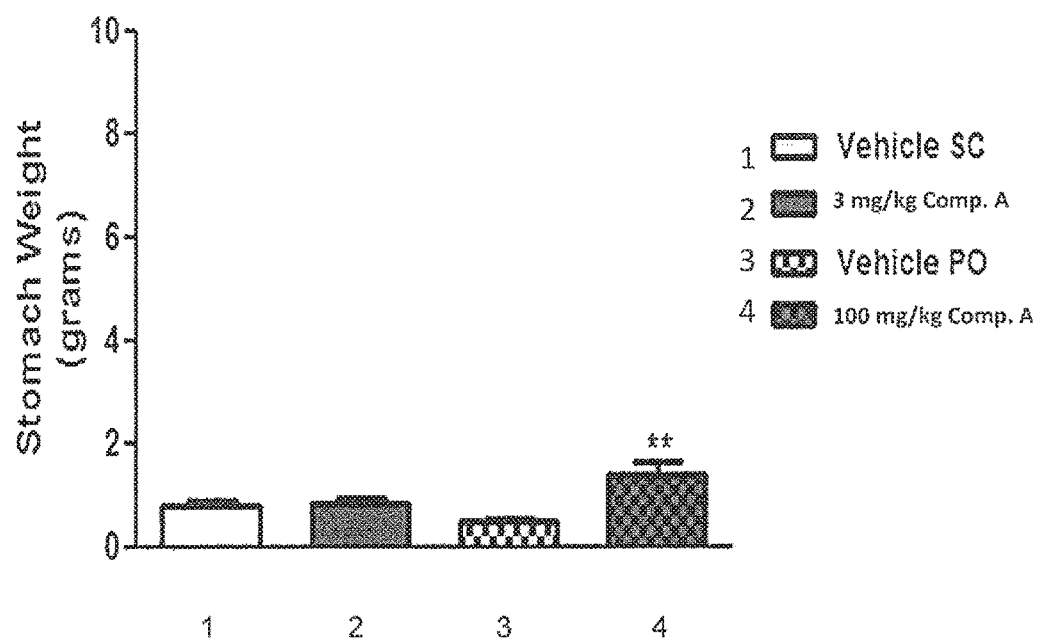
Figure 2C:
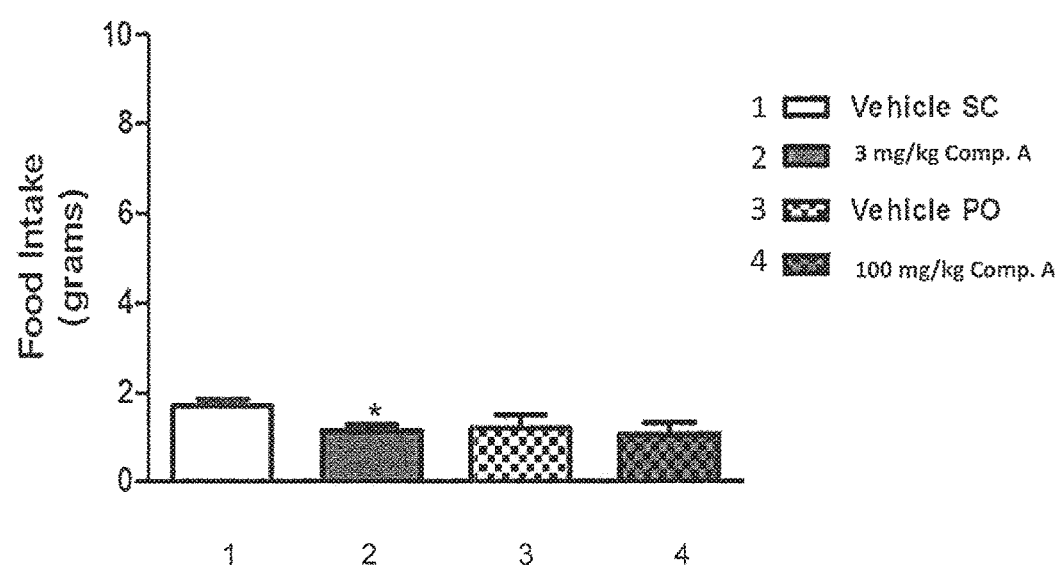

FIGS. 2B and 2C show the effect of Compound A dosing on the test animals' stomach weight and food intake, respectively. A stomach weight increase was observed for the 100 mg/kg dosage Compound A in 0.5% MC administered orally.

Example 3

The Effect of Repeated Administration of Compound A on Gastric Emptying, Food Intake and Whole Body Weight Male, Sprague-Dawley rats (weighing between 240-283 g each and 5-6 rats per test group) were orally dosed with 3 mg/kg, 10 mg/kg or 30 mg/kg of Compound A with a 0.5% MC vehicle or with a 0.5% MC vehicle alone once a day for five days and were then fasted overnight. The rats were then dosed again on the sixth day and placed in individual, bedding-free cages and allowed ad libitum access to pre-weighed food and water for two hours. The food and water were then removed and the food was reweighed. Data were analyzed using a one-way ANOVA followed by a Dunnett's Multiple Comparison Test, where *$P<0.05$ as compared to the appropriate vehicle. Data are represented as the means+S.E.M. % Gastric Emptying in 4 hours=(1−(gastric content/food intake))×100.

Figure 3A:
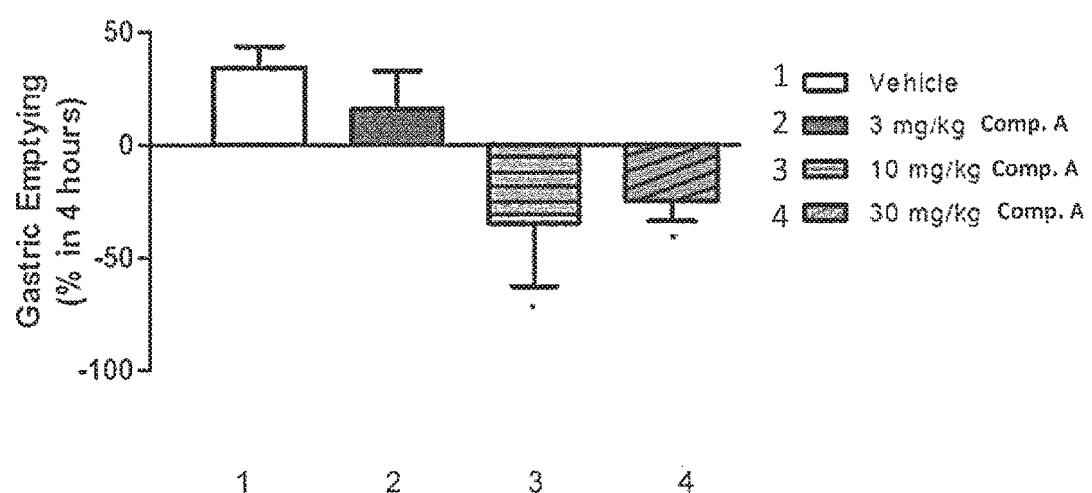
FIGS. 3A-3D are graphical depictions of the effect of repeated oral administration of Compound A on the percentage of gastric emptying, food intake, percentage of body weight change throughout the duration of the experiment, and total body weight variations, respectively, in test animals in accordance with Example 3.
Figure 3B:
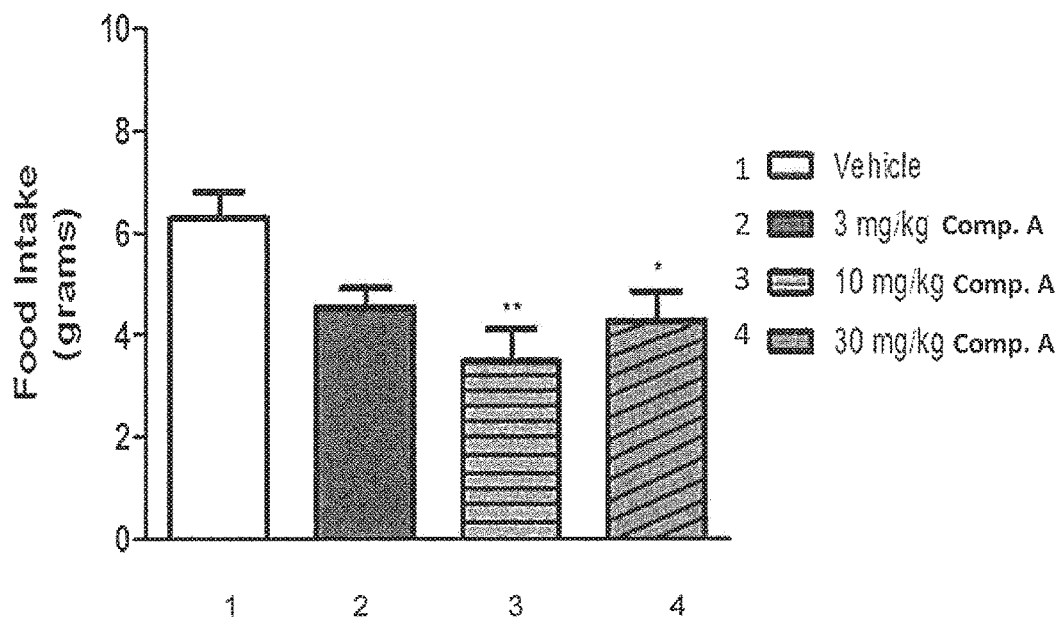
Figure 3C:
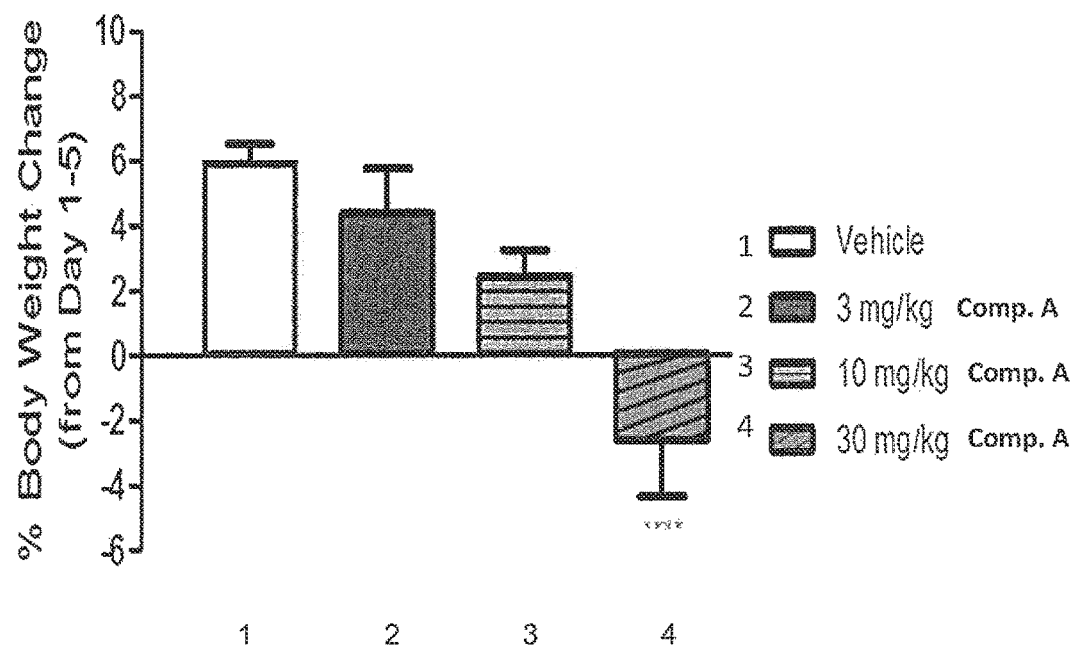
Figure 3D:
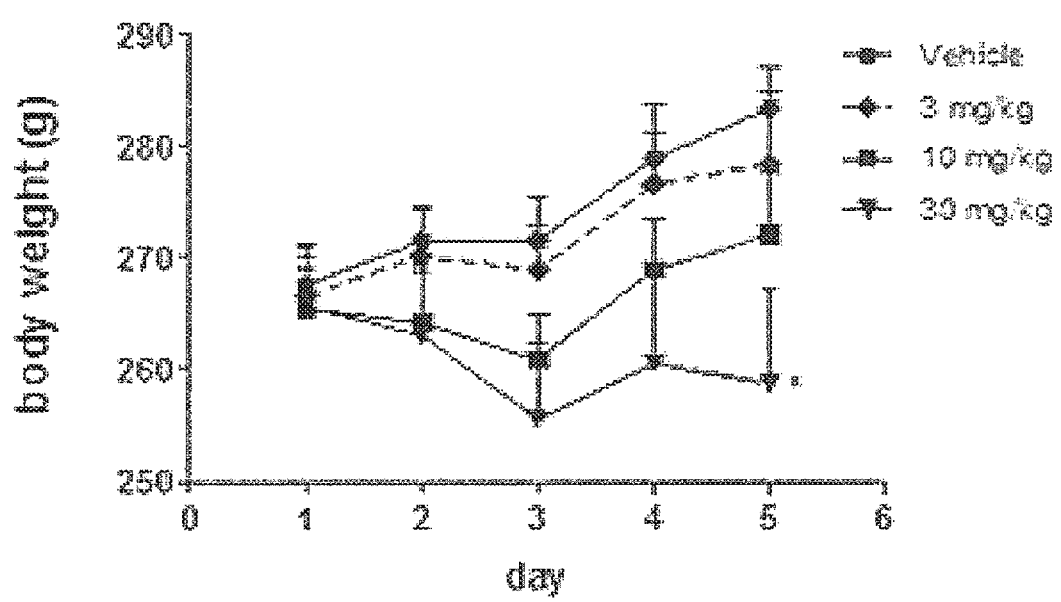

Gastric emptying following repeated oral administration of Compound A once a day for 6 days inhibited the percentage of gastric emptying. The dose dependence halts at 10 mg/kg after which no additional decrease in gastric emptying (FIG. 3A) and in food intake (FIG. 3B) was observed. Body weight (as measured on day 5 to avoid the potential confound of the overnight fast prior to determination of gastric emptying) decreased for all Compound A dosage levels. The greatest body weight decrease was observed for the 30 mg/kg dosage (FIG. 3C). While vehicle treated animals gained 15.8 g over 5 days, animals treated with 30 mg/kg of Compound A had a mean body weight loss of 6.3 g (FIG. 3D). Expressed as a percentage of total body weight, vehicle treated animals gained 5.9% while Compound A (30 mg/kg) treated animals lost 2.6% (FIG. 3C).

Example 3 shows that repeated administration of Compound A for 6 days produces a decrease in gastric emptying that is accompanied by a decrease in food intake and body weight.

Example 4

The Effect of Carbamazepine on Gastric Emptying Following Subcutaneous Administration Male, Sprague-Dawley rats (weighing between 235-268 g each and 4-6 rats per test group) were fasted overnight (19 hours). The rats were then subcutaneously administered 10 mg/kg, 30 mg/kg or 100 mg/kg of carbamazepine (Compound B) with a 25% HPBCD vehicle or with a 25% HPBCD vehicle alone. Some test animals were not dosed (i.e., naïve). The rats were then placed in individual, bedding-free cages and allowed ad libitium access to pre-weighed food and water for two hours. The food and water were then removed and the food was reweighed. Data were analyzed using a one-way ANOVA followed by a Dunnett's Multiple Comparison Test, where ***P<0.001 as compared to the appropriate vehicle. Data are represented as the means+S.E.M. % Gastric Emptying in 4 hours=(1−(gastric content/food intake))×100.

Figure 4A:
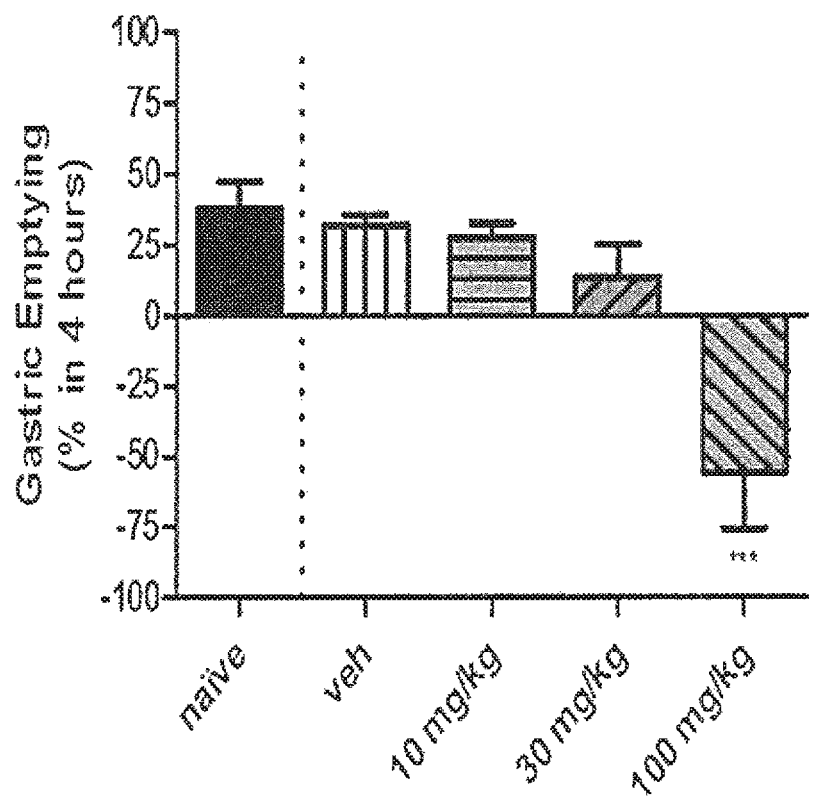
FIGS. 4A-4C are graphical depictions of the effect of subcutaneous dosing of Compound B with a 25% hydroxy-betacyclodextran (HPBCD) vehicle on the percentage of gastric emptying, stomach weight, and food intake, respectively, in test animals in accordance with Example 4.
Figure 4B:
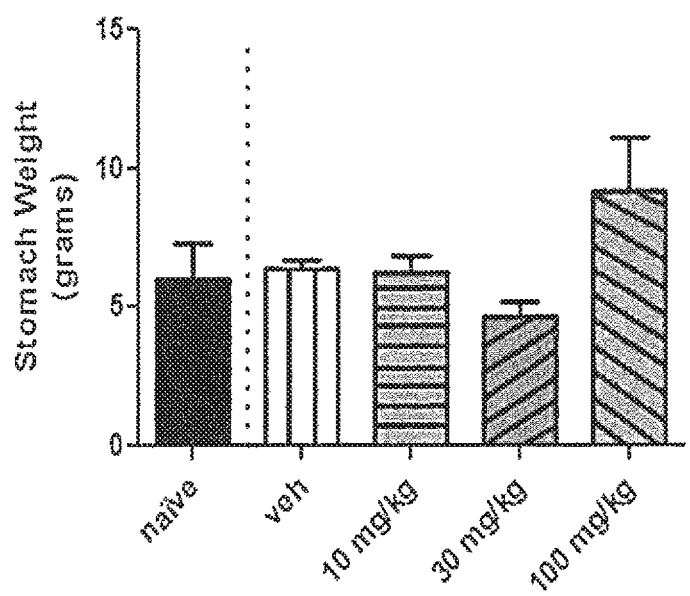
Figure 4C:
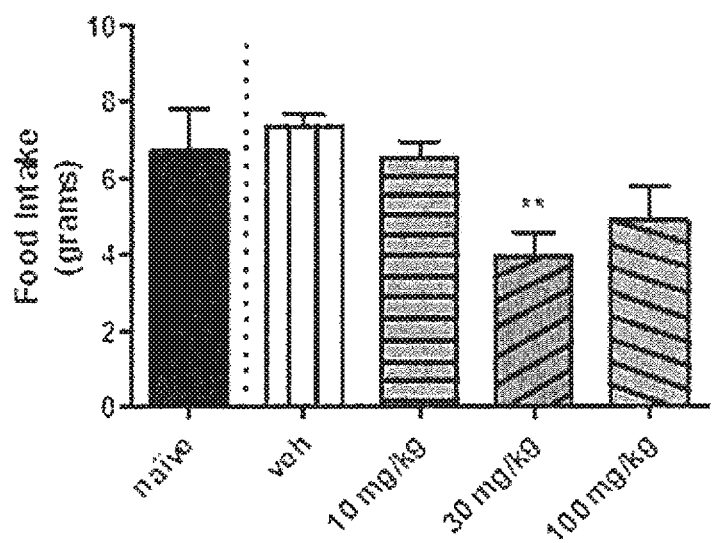

FIG. 4A shows the effect of subcutaneous dosing of Compound B with a 25% HPBCD vehicle on the percent of gastric emptying in the rats from Example 4. FIGS. 4B and 4C show the effect of subcutaneous dosing of Compound B with a 25% HPBCD vehicle on stomach weight and food intake, respectively, of the test animals in Example 4. FIG. 4A illustrates that compound B inhibits the percent of gastric emptying when compared to naïve test animals or test animals administered with a vehicle alone. The potency of gastric emptying inhibition increases with increasing Compound B dosage. The food intake decreased with increased compound B dosages (FIG. 4C). A stomach weight increase was observed at 100 mg/kg as compared to the controls. Compound A illustrated greater gastric emptying inhibition potency than Compound B at equal dosages.

Example 5

The Effect of Carbamazepine on Gastric Emptying Following Oral Administration

Male, Sprague-Dawley rats (weighing between 238-274 g each and 6 rats per test group) were fasted overnight (19 hours). The rats were then orally administered 30 mg/kg, 100 mg/kg or 300 mg/kg of carbamazepine (Compound B) with a 0.5% MC vehicle or with a 0.5% MC vehicle alone. The rats were then placed in individual, bedding-free cages and allowed ad libitium access to pre-weighed food and water for two hours. The food and water were then removed and the food was reweighed. Data were analyzed using a one-way ANOVA followed by a Dunnett's Multiple Comparison Test, where *P<0.05 and ***P<0.001 as compared to the appropriate vehicle. Data are represented as the means+S.E.M. % Gastric Emptying in 4 hours=(1−(gastric content/food intake))×100.

Figure 5A:
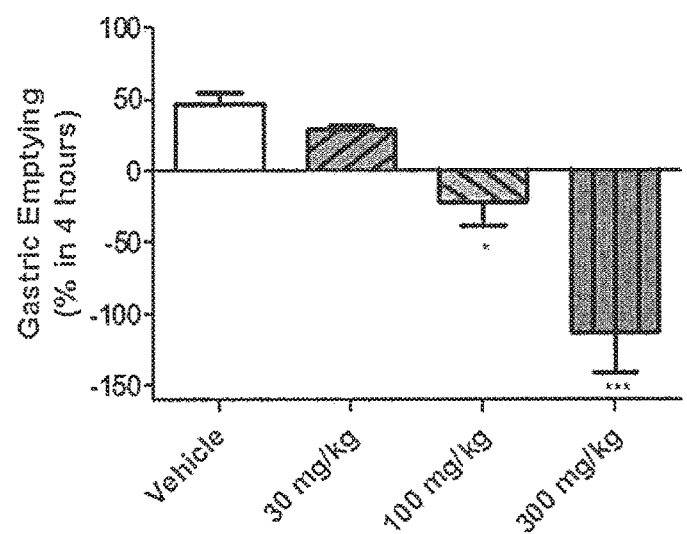
FIGS. 5A-5C are graphical depictions of the effect of oral dosing of Compound B with a 0.5% MC vehicle on the percentage of gastric emptying, stomach weight, and food intake, respectively, in test animals in accordance with Example 5.
Figure 5B:
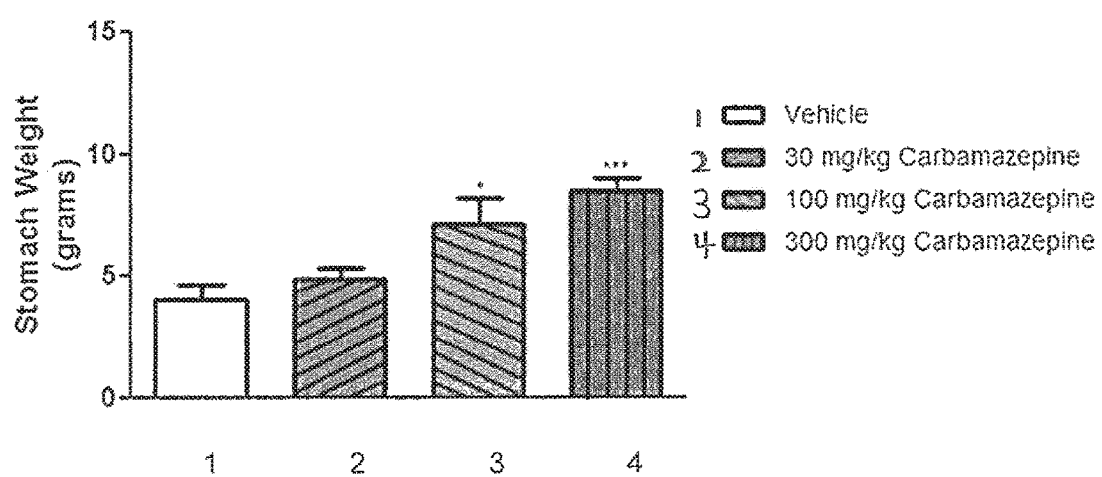
Figure 5C:
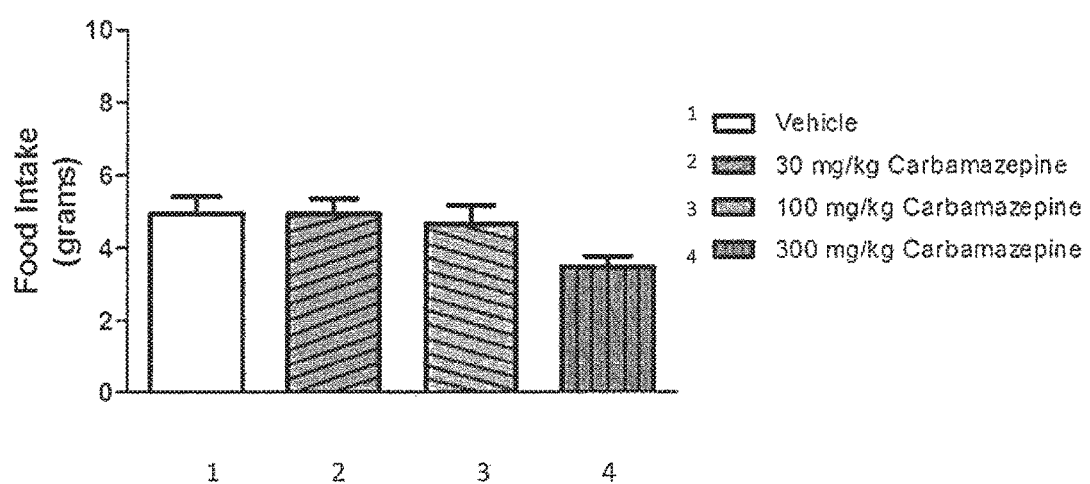

FIGS. 5A-5C show the effect of oral dosing of Compound B with a 0.5% MC vehicle on the percent of gastric emptying, the stomach weight, and food intake, respectively, in the rats from Example 5.

Example 5 and the corresponding figures illustrate that oral administration of carbamazepine inhibits gastric emptying, increases stomach weight, and reduces food intake in the test animals as compared to the administration of vehicle alone. The potency of Compound B to inhibit gastric emptying, increase stomach weight, and reduce food intake is dosage dependent. Thus, the potency increases with increased dosage. A comparison between Examples 4 and 5 illustrate that when an equal dosage of compound B is administered orally with a 0.5% MC vehicle it is numerically more potent with respect to the percent of gastric inhibition than if administered subcutaneously with a 25% HPBCD vehicle. Although unequal exposure may result from varying routes of administration, it would be expected that oral administration be less potent than subcutaneous and not vice versa as illustrated herein.

Nevertheless, Compound A remained of greater gastric emptying inhibition potency when compared to Compound B (despite similar dosages, administration routes, and similar vehicles.

Example 6

The Effect of Compound C on Gastric Emptying Following Oral and Subcutaneous Administration Male, Sprague-Dawley rats (weighing between 235-276 g each and 4-6 rats per test group) were fasted overnight (19 hours). The rats were then orally administered 10 mg/kg, 30 mg/kg or 100 mg/kg of Compound C with a 0.5% MC vehicle or a 0.5% MC vehicle alone or were subcutaneously administered 10 mg/kg, 30 mg/kg or 100 mg/kg of Compound C with a 25% HPBCD vehicle or with a 25% HPBCD vehicle alone with unequal exposures between the oral and subcutaneous administrations. Some test animals were not dosed (i.e., naïve). The rats were then placed in individual, bedding-free cages and allowed ad libitium access to pre-weighed food and water for two hours. The food and water were then removed and the food was reweighed. Gastric emptying was then assessed four hours later by euthanizing the rats and analyzing the stomach and stomach contents. Data were analyzed independently for each vehicle using a one-way ANOVA followed by a Dunnett's Multiple Comparison Test, where *P<0.05. Data are represented as the means+S.E.M. % Gastric Emptying in 4 hours=(1−(gastric content/food intake))×100.

Figure 6A:
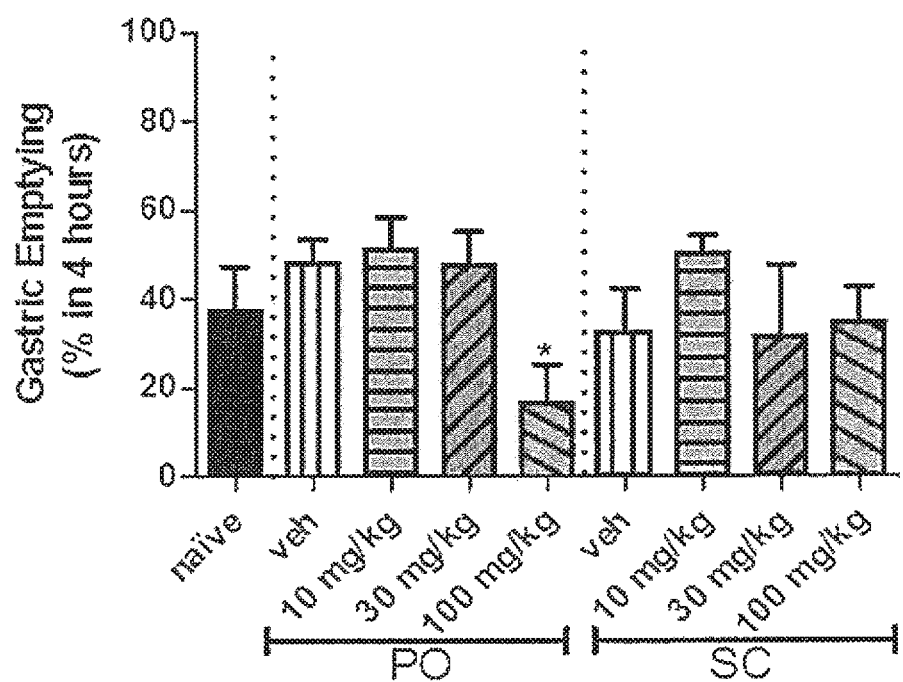
FIGS. 6A-6C are graphical depictions of the effect of the type of administration, vehicle, and dosing of Compound C on the percentage of gastric emptying, stomach weight, and food intake, respectively, in test animals in accordance with Example 6.
Figure 6B:
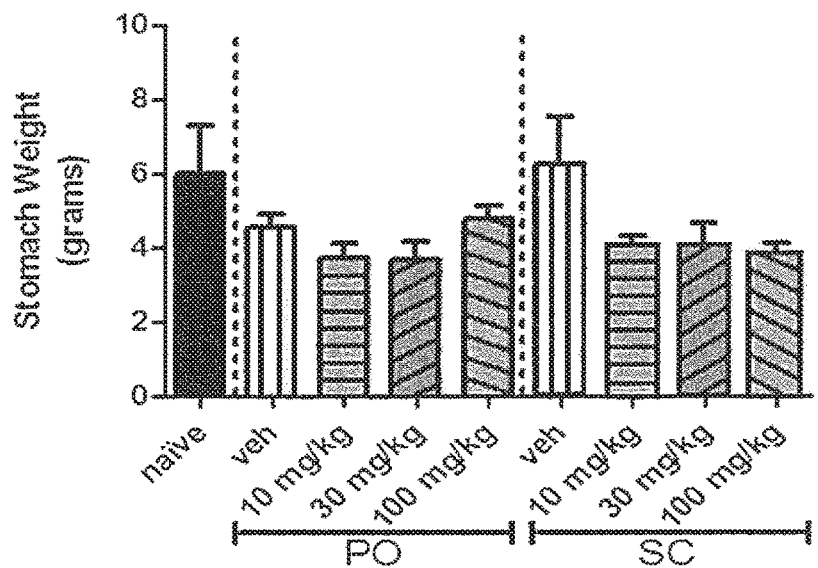
Figure 6C:
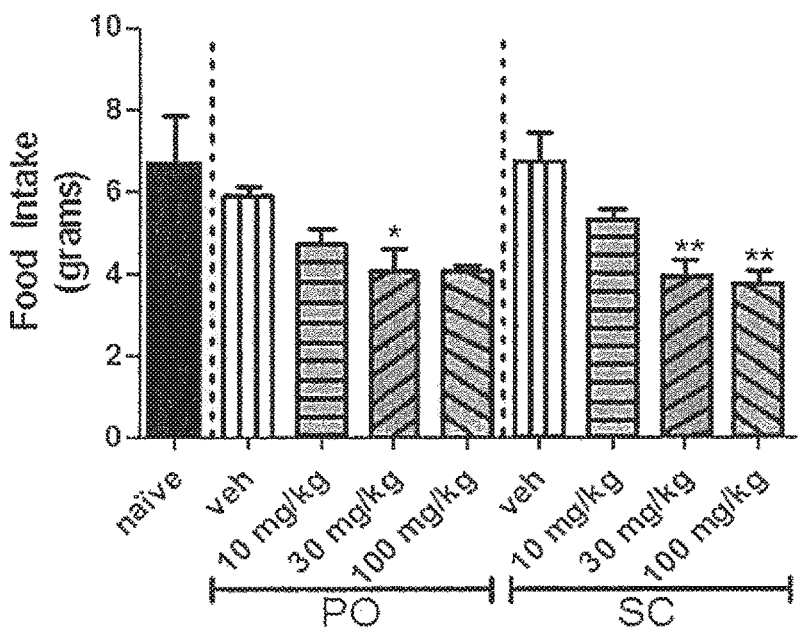

FIGS. 6A-6C show the effect of the type of administration, vehicle, and dosing of Compound C on the percent of gastric emptying, stomach weight, and food intake, in the rats from Example 6.

FIGS. 6A-6C illustrate that oral administration of 100 mg/kg of Compound C inhibits the percentage of gastric emptying, increases stomach weight, and reduces food intake as compared to naïve animals or animals administered a vehicle alone. Oral administration of lower dosages of Compound C (e.g., 10 mg/kg and 30 mg/kg dosages) reduced food intake (FIG. 6C) but did not affect the percentage of gastric emptying or stomach weight.

In comparison, subcutaneous administration of all dosages of Compound C tested, decreased the stomach weight and food intake as compared to naïve animals or animals administered a vehicle alone. However, subcutaneous administration of compound C did not inhibit the percentage of gastric emptying at the dosages administered herein (FIG. 6A, 10 mg/kg).

A comparison between Compounds A, B, and C illustrate that at an equal dosage and equal administration route (such as: oral administration with a 0.5% MC vehicle or subcutaneous administration with a 25% HPBCD vehicle), Compound C is the least potent with respect to inhibition of gastric emptying at lower dosages.

Example 7

The Effect of Compound C on Gastric Emptying Following Oral Administration Dose Extension Male, Sprague-Dawley rats (weighing between 239-276 g each and 6-13 rats per test group) were fasted overnight (19 hours). The rats were then orally administered 10 mg/kg, 30 mg/kg, 100 mg/kg or 300 mg/kg of Compound C with a 0.5% MC vehicle or with a 0.5% MC vehicle alone. The rats were then placed in individual, bedding-free cages and allowed ad libitium access to pre-weighed food and water for two hours. The food and water were then removed and the food was reweighed. Gastric emptying was then assessed four hours later by euthanizing the rats and analyzing the stomach and stomach contents. Data were analyzed using a one-way ANOVA followed by a Dunnett's Multiple Comparison Test, where *P<0.05 and ***P<0.001 as compared to the appropriate vehicle. Data are represented as the means+S.E.M. % Gastric Emptying in 4 hours=(1−(gastric content/food intake))×100. Data are combined from two studies.

Figure 7A:
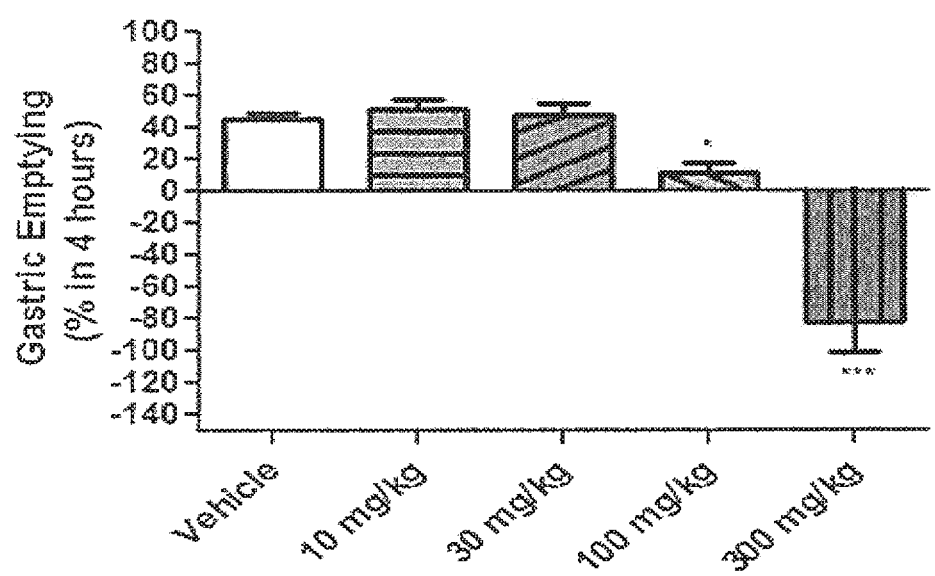
FIGS. 7A-7C is a graphical depiction of the effect of oral dosing of Compound C with a 0.5% MC vehicle on the percentage of gastric emptying, stomach weight, and food intake, respectively, in test animals in accordance with Example 7.
Figure 7B:
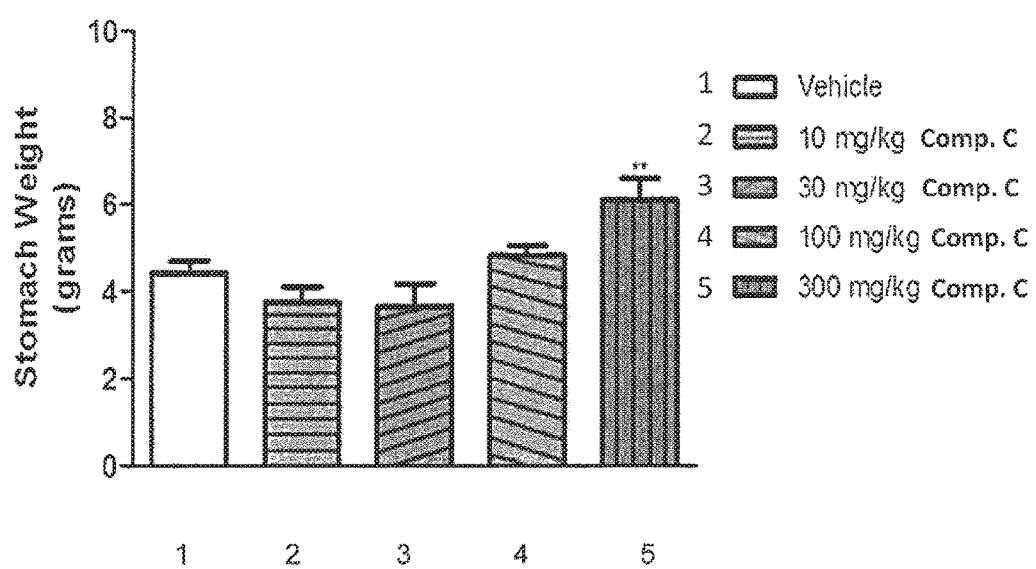
Figure 7C:
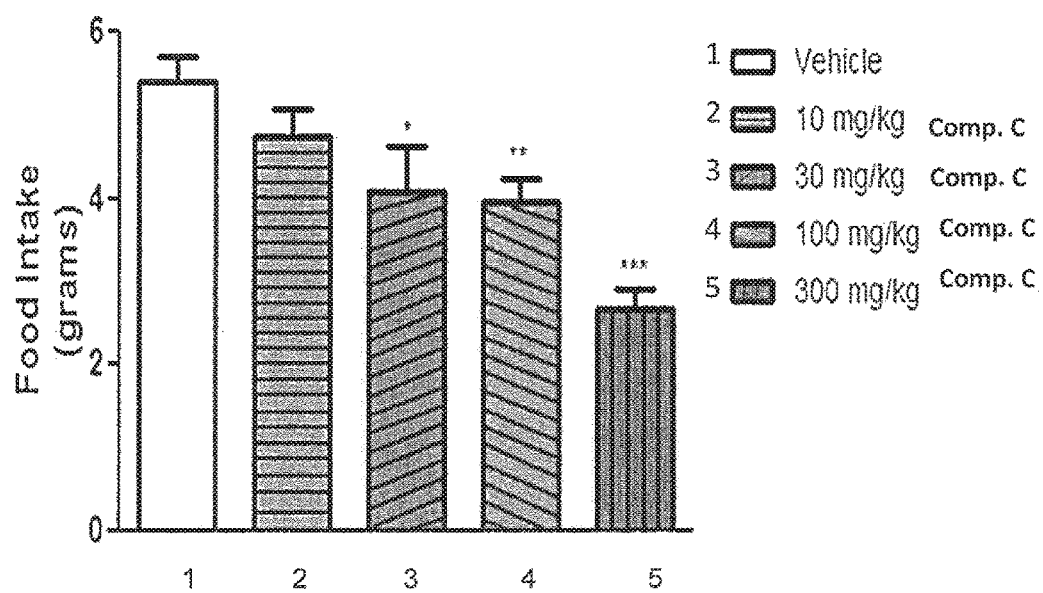

FIG. 7A-7C show the effect of oral dosing of Compound C on the percent of gastric emptying, stomach weight, and food intake, respectively, in the rats from Example 7. Since Example 6 illustrated low potency for Compound C, the dosage was extended in the present example to 300 mg/kg.

Example 7 and its corresponding figures show that Compound C inhibits gastric emptying (100 mg/kg and 300 mg/kg), reduces food intake, and increases stomach weight (100 mg/kg and 300 mg/kg) in the test animals as compared to test animals administered a vehicle alone. The potency of Compound C increases with increased dosage.

Example 8

The Effect of Compound D on Gastric Emptying Following Intraperitoneal Administration Male, Sprague-Dawley rats (weighing between 239-273 g each and 6 rats per test group) were fasted overnight (19 hours). The rats were then intraperitoneally administered 10 mg/kg, 30 mg/kg or 100 mg/kg of Compound D with a 25% HPBCD vehicle or 25% HPBCD vehicle alone. The rats were then placed in individual, bedding-free cages and allowed ad libitum access to pre-weighed food and water for two hours. The food and water were then removed and the food was reweighed. Gastric emptying was then assessed four hours later by euthanizing the rats and analyzing the stomach and stomach contents. Data were analyzed using a one-way ANOVA followed by a Dunnett's Multiple Comparison Test, where **P<0.01 as compared to the appropriate vehicle. Data are represented as the means+S.E.M. % Gastric Emptying in 4 hours=(1−(gastric content/food intake))×100.

Figure 8A:
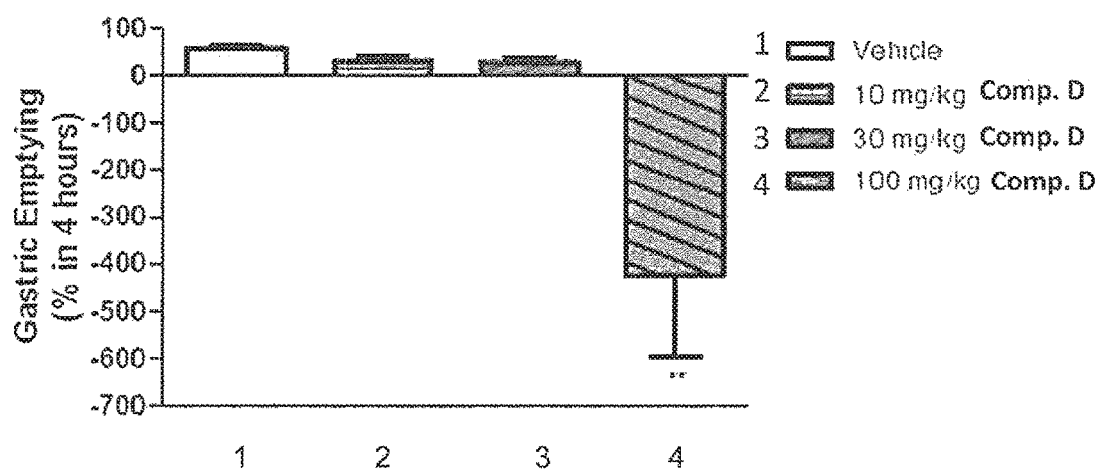
FIGS. 8A-8C are graphical depictions of the effect of intraperitoneal dosing of Compound D with a 25% HPBCD vehicle on the percentage of gastric emptying, stomach weight, and food intake, respectively, in test animals in accordance with Example 8.
Figure 8B:
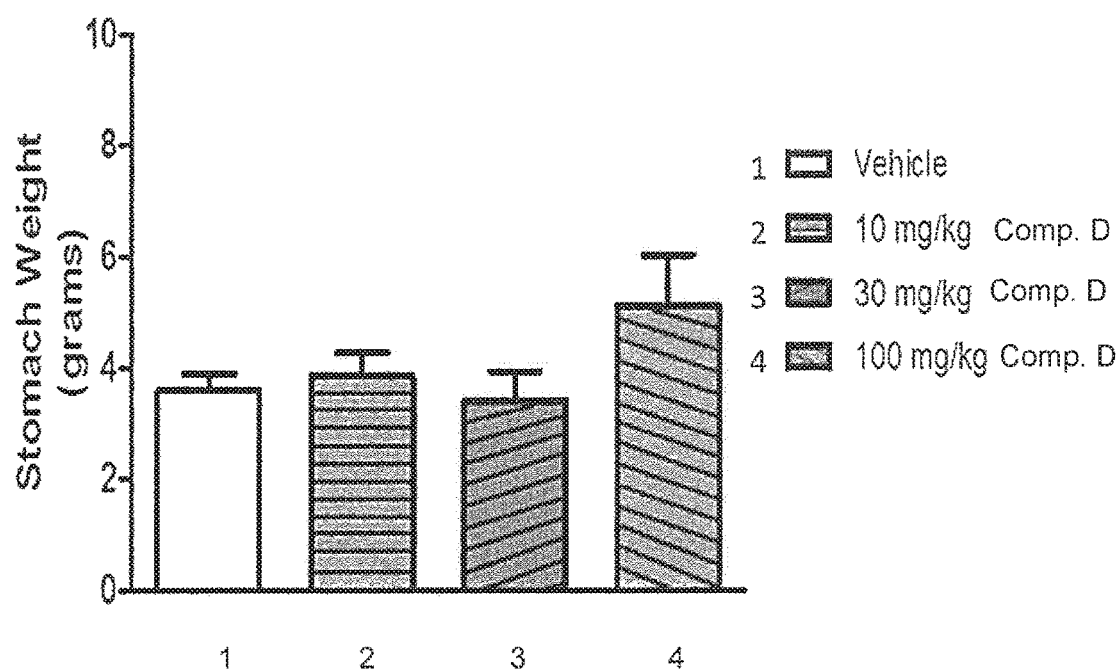
Figure 8C:
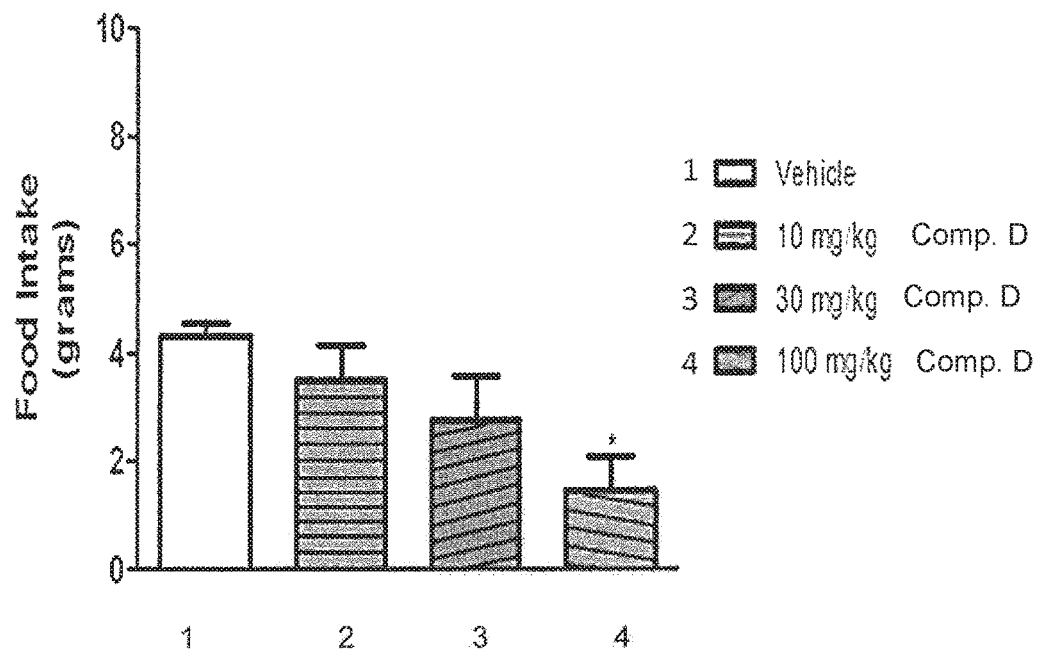

FIG. 8A-8C show the effect of intraperitoneal dosing of Compound D on the percent of gastric emptying, stomach weight, and food intake in the rats from Example 8.

Example 8 and its corresponding figures show that Compound D inhibits gastric emptying (FIG. 8A), reduces food intake (FIG. 8C), and increases stomach weight (FIG. 8B, 10 mg/kg and 100 mg/kg) in the test animals as compared to test animals administered a vehicle alone. The potency of Compound D increases with increased dosage. Compound D illustrated greater gastric emptying inhibition potency than Compounds B and C at similar dosages, administration routes, and vehicles. Oral dosing of Compound A with a 0.5% MC vehicle has greater gastric emptying inhibition potency at lower dosages (e.g., 10 mg/kg and 30 mg/kg), although this observation reverses at 100 mg/kg. Subcutaneous dosing of Compound A with a CSP vehicle maintains a greater gastric emptying inhibition potency as compared to Compound D in 25% HPBCD throughout all dosages tested.

Example 9

Blockade of Sodium Channels Reduces Gastric Emptying and Increases Stomach Weight The results of Examples 1, 5 and 7 tested the effects of Nav channel blockade on gastric emptying by determining how much of an ingested meal remained in the stomach after 4 hours. In animals treated with vehicle approximately 50% of the ingested weight of food remained in the stomach (and 50% has emptied). All three Nav blockers resulted in a dose dependent and statistically significant decrease in gastric emptying such that a higher percent of the ingested meal remained in the stomach (FIGS. 1A, 5A and 7A). In each case with increasing dose and exposure the effect increased to a point where at the highest dose tested, gastric emptying was less than 0 (a negative number) indicating that the weight of the stomach contents exceeded the weight of the ingested meal; this is likely due to increased gastric secretion from the stomach and/or weight of residual ingested water (possibly complexed with the ingested food).

Compound A displayed the highest in vivo potency with a large numerical decrease observed (reduced to ~0% emptying) following the lowest dose tested orally (10 mg/kg). When administered subcutaneously Compound A also produced a decrease in gastric emptying, however, a 3-10 fold increase in potency as compared to oral administration was noted (FIG. 1A). Consistent with the findings observed in the gastrointestinal transit assay, all three compounds also produced an increase in stomach weight (FIGS. 1B, 5B and 7B) in this assay.

Example 10

The Effect of Compound A on Gastric Secretion

Male, Sprague-Dawley rats (weighing between 254-270 g each and 6 rats per test group) were fasted overnight (24 hours) on wire inserts without bedding. The rats were first orally dosed with 0.5% MC vehicle and then subcutaneously injected with 3 mg/kg or 10 mg/kg of Compound A with a 25% HPBCD vehicle or with a 25% HPBCD vehicle alone. The test animals were water deprived for 3 hours and then anesthetized with isoflurane and the pylorus and cardia were tightly ligated. The stomachs were then removed and the rats were euthanized. The gastric fluid was removed from the stomachs and collected in eppendorf tubes by cutting along the greatest curvature and spun in a centrifuge. Gastric secretion data were analyzed by a one-way ANOVA using a Bonferroni Mulitple Comparison test, where *P<0.05 and **P<0.01 as compared to the appropriate vehicle. Data are represented as the means+S.E.M. PH data were analyzed by a one-way ANOVA using Dunnett's Multiple Comparison Test. Data are represented as the means+S.E.M.

Figure 9A:
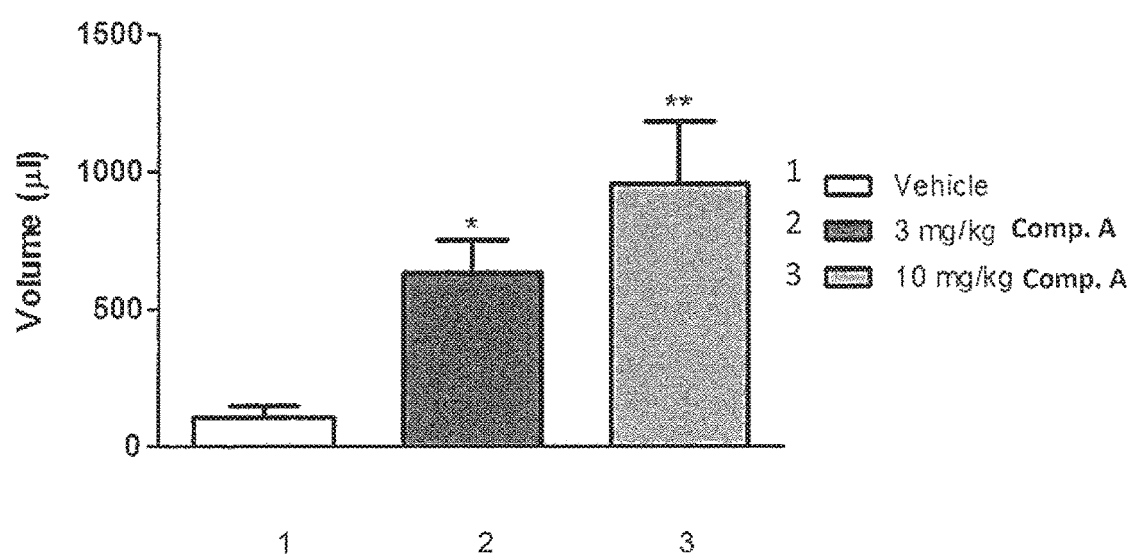
FIGS. 9A-9B are graphical depictions of the effect of subcutaneous dosing of Compound A with 25% HPBCD vehicle, after an oral dose of 0.5% MC, on the volume of gastric secretion and on the pH of gastric secretion, respectively, in test animals in accordance with Example 10.
Figure 9B:
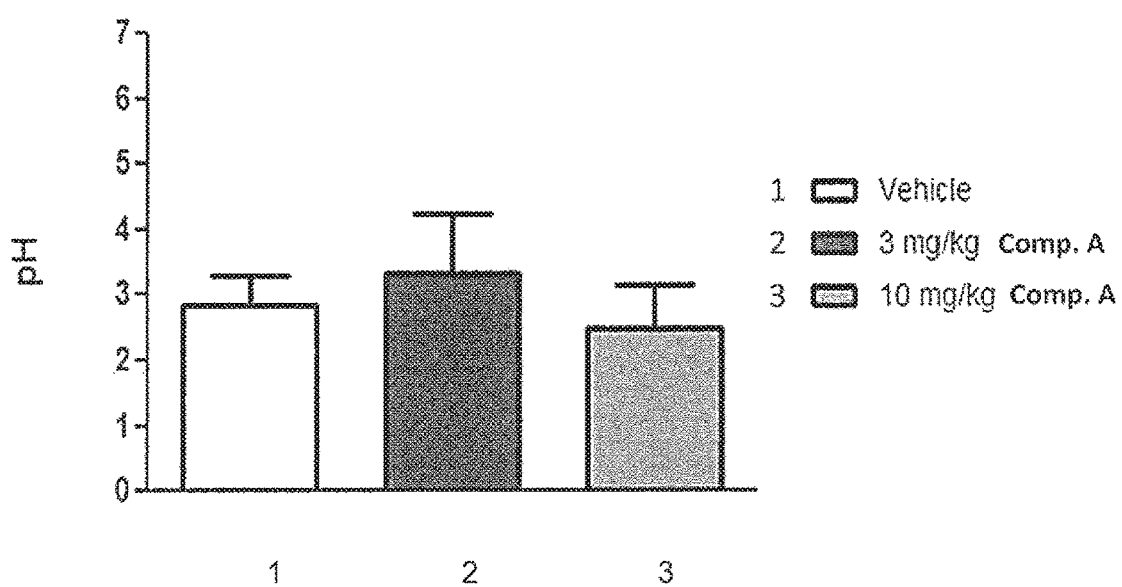

FIGS. 9A-9B show the effect of subcutaneous dosing of Compound A with 25% HPBCD vehicle, after an oral dose of 0.5% MC, on the volume and on the pH of gastric secretion in the rats from Example 10. The volume of gastric secretion increases with increasing doages of Compound A while the pH or acidity remains unaffected.

Example 11

The Effect of Atenolol Pre-Treatment on Compound a Induced Inhibition of Gastric Emptying Male, Sprague-Dawley rats (weighing between 226-254 g each and 6 rats per test group) were fasted overnight (19 hours). The rats were orally administered 10 mg/kg atenolol with a 0.5% MC vehicle or 0.5% MC vehicle alone and then subcutaneously administered either 3 mg/kg Compound A with a 25% HPBCD vehicle or 25% HPBCD vehicle alone. The rats were then placed in individual, bedding-free cages and allowed ad libitum access to pre-weighed food and water for two hours. The food and water were then removed and the food reweighed. Gastric emptying was then assessed four hours later by euthanizing the rats and analyzing the stomach and stomach contents. Data were analyzed using a one-way ANOVA followed by a Dunnett's Multiple Comparison Test, where *P<0.05 and **P<0.01 as compared to the vehicle+vehicle combination. Data are represented as the means+S.E.M. % Gastric Emptying in 4 hours=(1−(gastric content/food intake))×100.

Figure 10A:
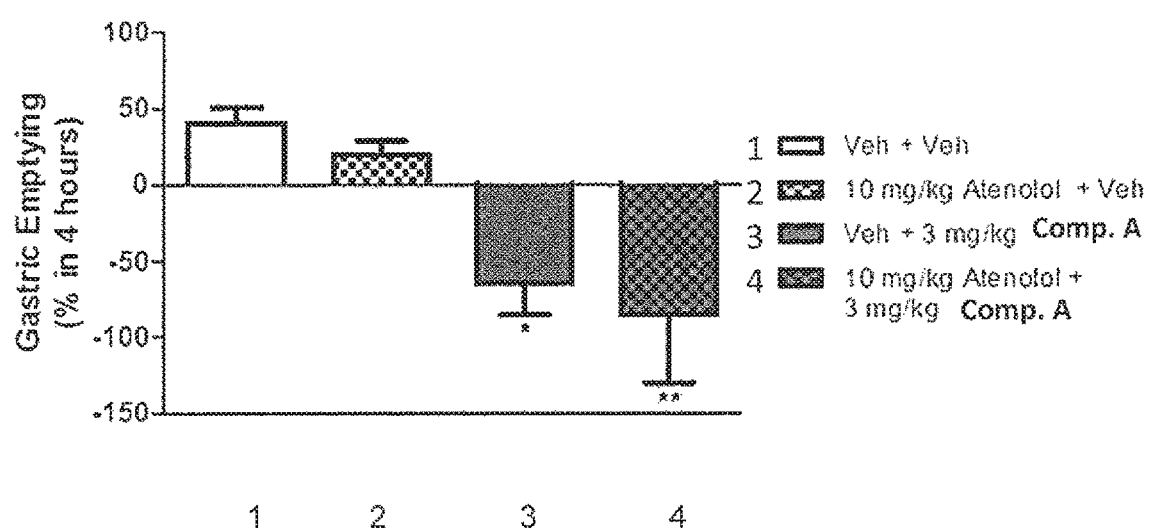
FIGS. 10A-10C are graphical depictions of the effect of various dosing combinations of 0.5% MC vehicle, 25% HPBCD, Atenolol, and Compound A on the percentage of gastric emptying, stomach weight, and food intake, respectively, in test animals in accordance with Example 11.
Figure 10B:
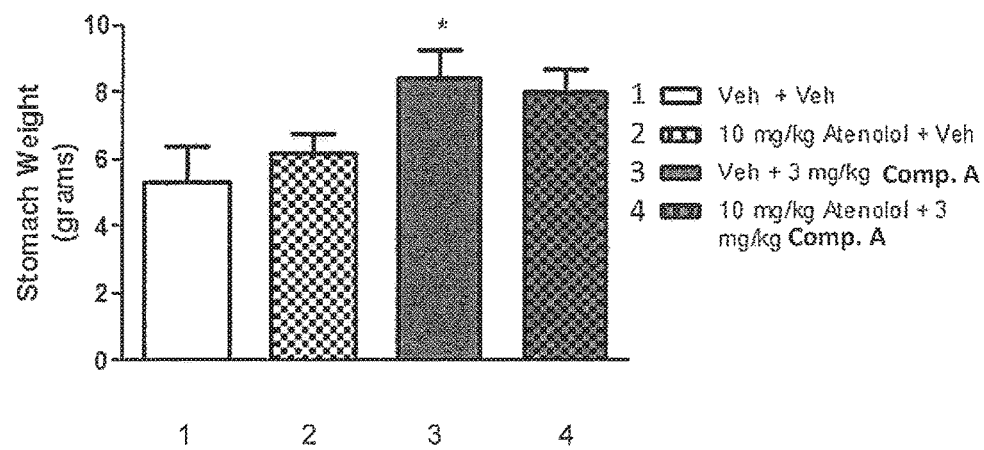
Figure 10C:
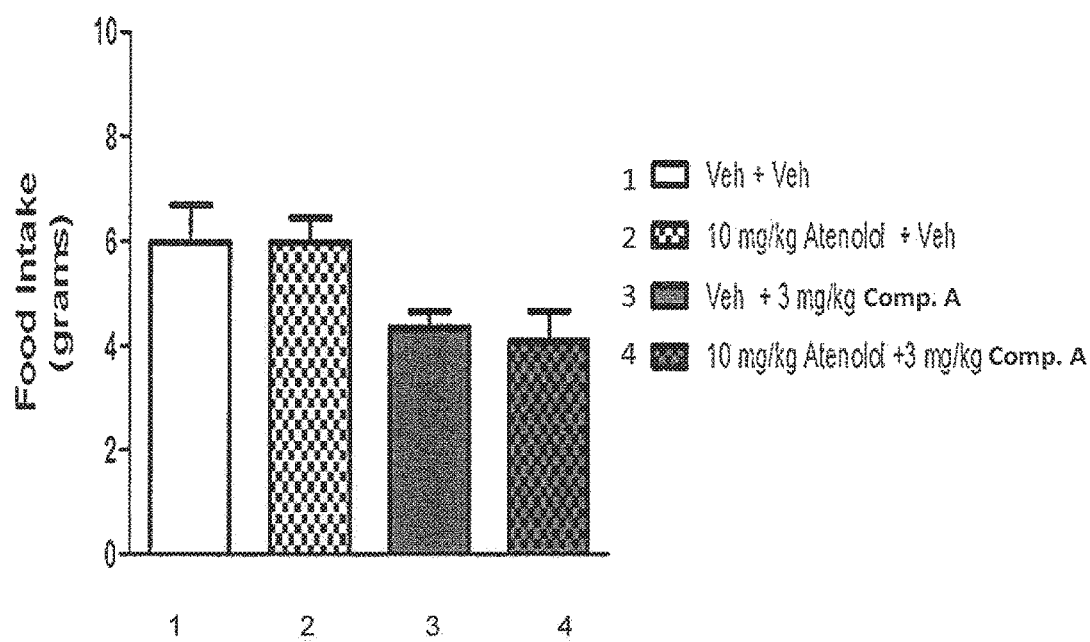

FIGS. 10A-10C show the effect of various dosing combinations of 0.5% MC vehicle, 25% HPBCD, Atenolol, and Compound A on the percent of gastric emptying, stomach weight, and food intake in the rats from Example 11.

Example 11 and its corresponding figures show that Atenolol beta blockade does not attenuate the effect of Compound A on gastric emptying. While Atenolol and compound A inhibit the precent of gastric emptying independently, the combination of Atenolol with Compound A inhibit the percent of gastric emptying even further (FIG. 10A). The stomach weight and food intake of Compound A together with Atenolol is comparable to that of Compound A alone.

Example 12

The Effect of Terazosin Pre-Treatment on Compound A Induced Gastric Emptying

Male, Sprague-Dawley rats (weighing between 218-263 g each and 8 rats per test group) were fasted overnight (19 hours). The rats were orally administered 30 mg/kg terazosin with a 0.5% MC vehicle or 0.5% MC vehicle alone. Half an hour later, the rats were subcutaneously administered 3 mg/kg Compound A with a 25% HPBCD vehicle or 25% HPBCD vehicle alone. The rats were then placed in individual, bedding-free cages and allowed ad libitum access to pre-weighed food and water for two hours. The food and water were then removed and the food was reweighed. Data were analyzed using a one-way ANOVA followed by a Dunnett's Multiple Comparison Test, where ***P<0.001 as compared to the appropriate vehicles. Data are represented as the means+S.E.M. % Gastric Emptying in 4 hours= (1−(gastric content/food intake))×100.

Figure 11A:
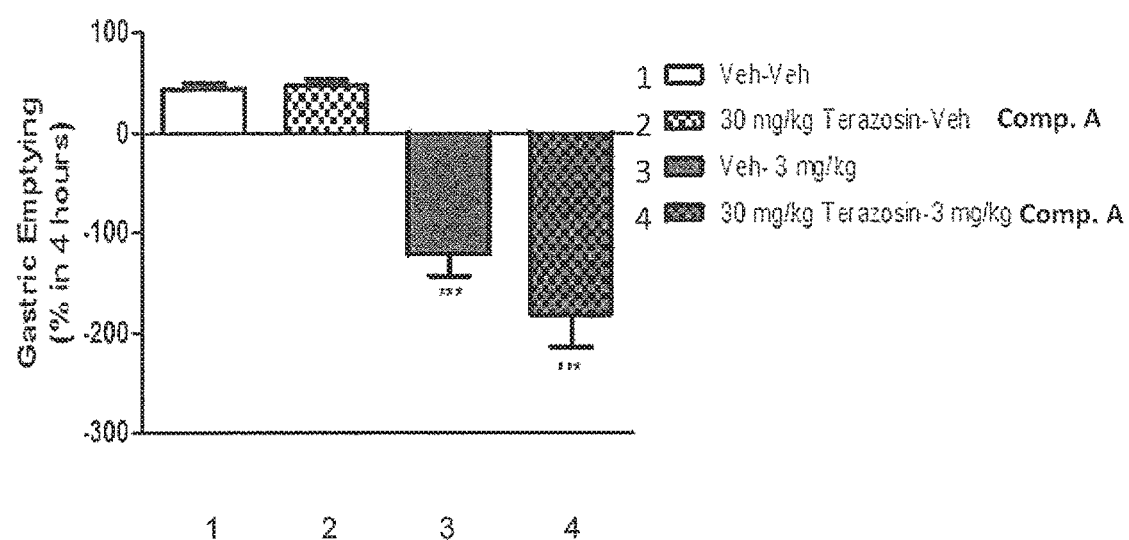
FIGS. 11A-11C are graphical depictions of the effect of various dosing combinations of 0.5% MC vehicle, 25% HPBCD, Terazosin, and Compound A on the percentage of gastric emptying, stomach weights, and food intake, respectively, in test animals in accordance with Example 12.
Figure 11B:
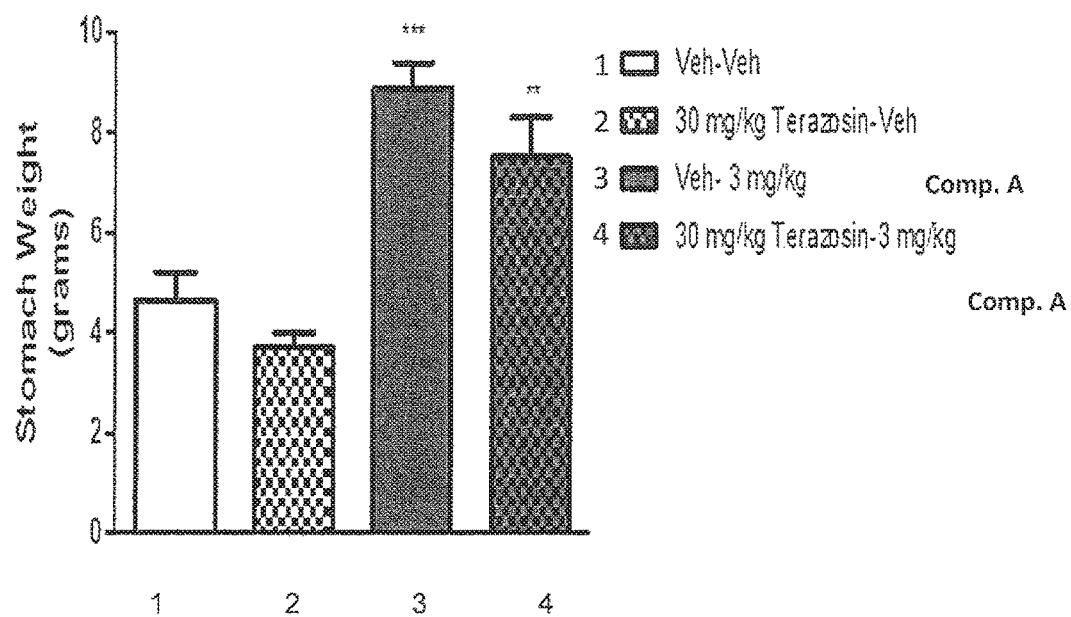
Figure 11C:
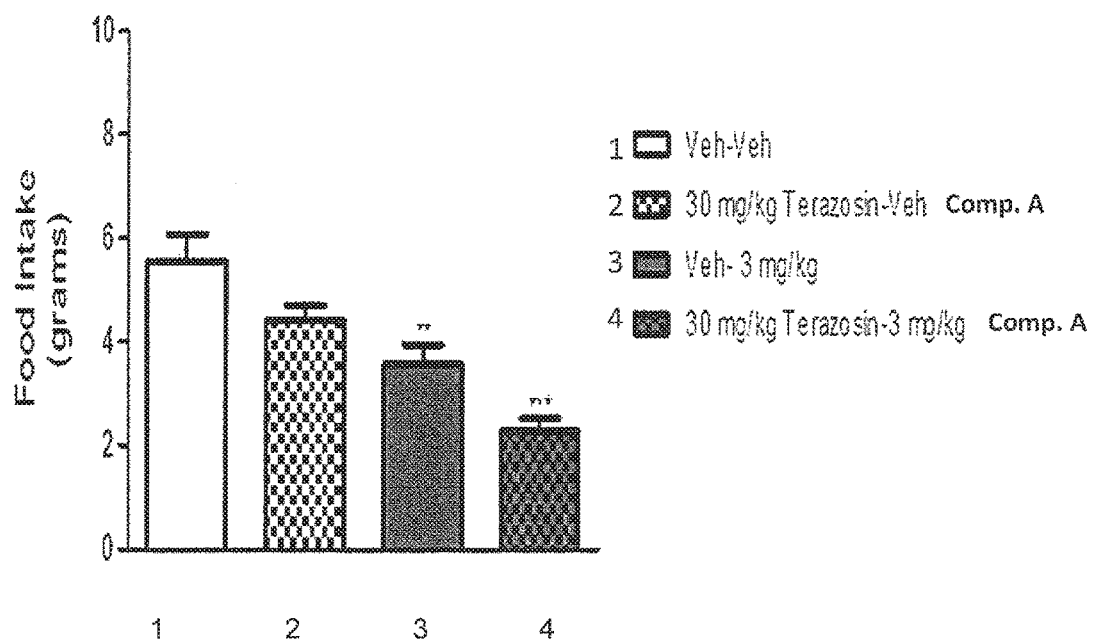

FIG. 11A-11C show the effect of various dosing combinations of 0.5% MC vehicle, 25% HPBCD, Terazosin, and Compound A on the percent of gastric emptying, stomach weight, and food intake in the rats from Example 12.

Example 12 and its corresponding figures show that Terazosin does not attenuate the effect of Compound A on gastric emptying. While compound A inhibits the precent of gastric emptying independently, the combination of Terazosin with Compound A surprisingly inhibit the percent of gastric emptying even further (FIG. 11A).

The combination of Compound A with Terazosin results in a decreased food intake (FIG. 11C). The decreased food intake amounts approximately to the added decrease in food intake due to Terazosin with the decrease in food intake due to Compound A.

The combination of Compound A with Terazosin results in an increased stomach weight as compared to rats administered with a vehicle alone, although the increase in stomach weight for the combination is lower than the increase exhibited for Compound A alone (FIG. 11B).

Example 13

The Effect of Vagotomy on Compound a Induced Inhibition of Gastric Emptying

Male, Sprague-Dawley vagotomized rats (Charles River, weighing between 205-323 g each and 8-10 rats per test group) and naïve rates (Harlan; weighing between 242-284 g each and 7 rats per test group) were fasted overnight (19 hours). The rats were then orally dosed with 100 mg/kg of Compound A with a 0.5% MC vehicle or a 0.5% MC vehicle alone. The rats were then placed in individual, bedding-free cages and allowed ad libitum access to pre-weighed food and water for two hours. The food and water were then removed and the food was reweighed. Gastric emptying was assessed four hours later by euthanizing the rats and analyzing the stomach and stomach contents. No statistical difference was captured between groups using an ANOVA. Analysis using an unpaired t-test shows ****P<0.0001. Data are represented as the means+S.E.M. % Gastric Emptying in 4 hours=(1−(gastric content/food intake))×100.

Figure 12A:
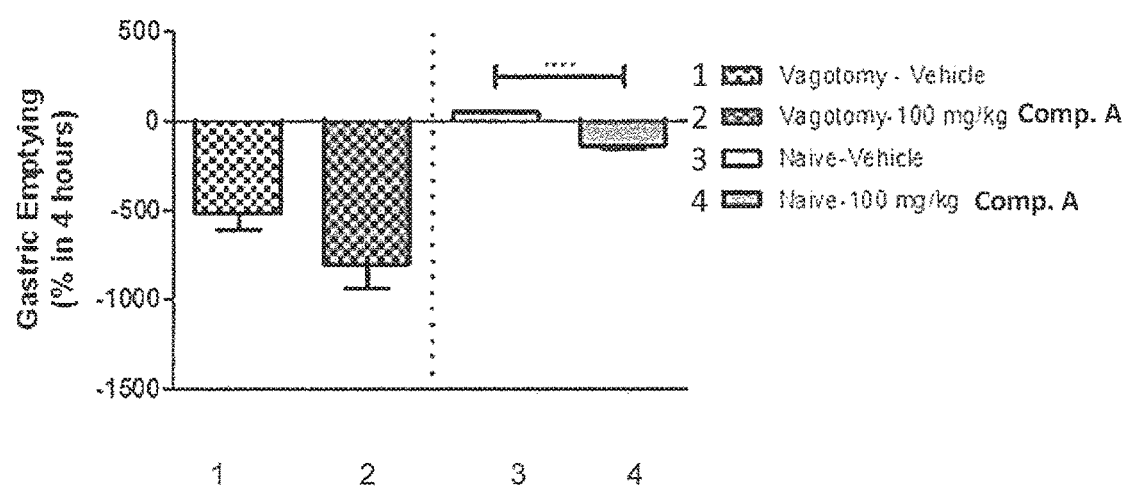
FIGS. 12A-12C are graphical depictions of the effect of Compound A dosing in vagotomized and naïve test animal on the percentage of gastric emptying, stomach weight, and food intake, respectively, in accordance with Example 13.
Figure 12B:
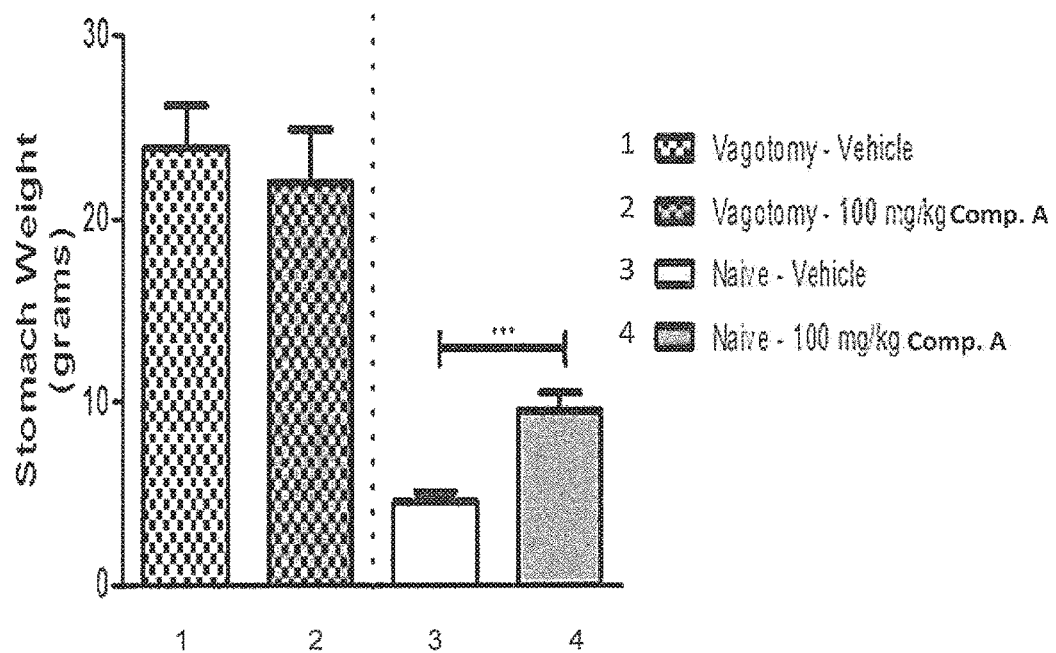
Figure 12C:
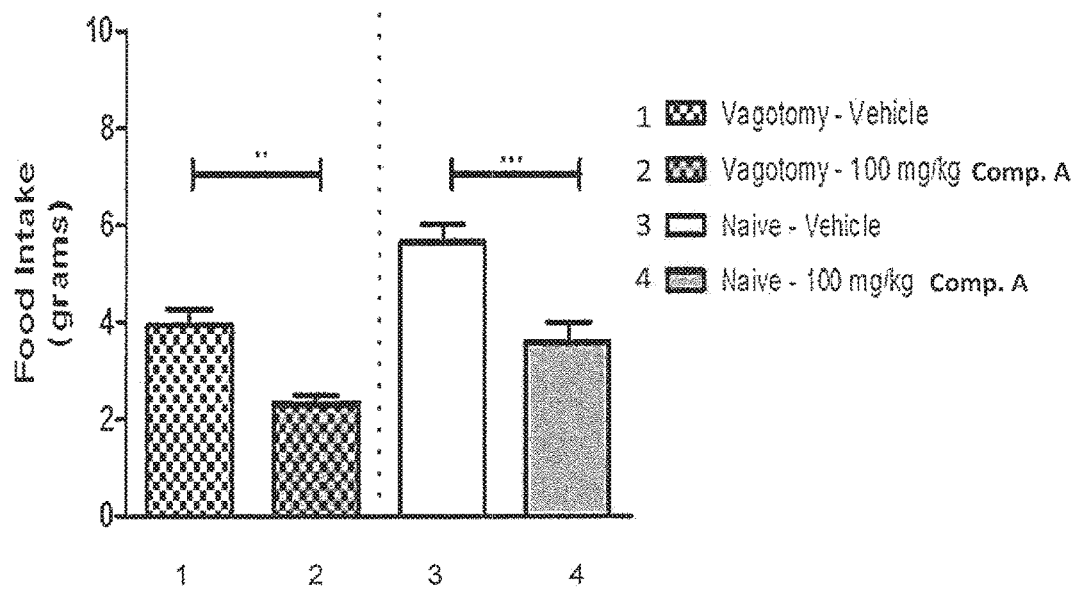

FIGS. 12A-12C show the effect of Compound A dosing in vagotomized and naïve test animals on the percent of gastric emptying, stomach weight, and food intake in the rats from Example 13.

Example 13 and its corresponding figures show that vagotomy together with Compound A have a numerically additive effect on the inhibition of gastric emptying but not a statistically significant effect. Food intake is inhibited in both vagotomized and naïve subjects upon administration of Compound A (FIG. 12C).

Example 14

The Effect of Tetrodotoxin on Gastric Emptying Following Subcutaneous Administration Male, Sprague-Dawley rats (weighing between 300-354 g each and 6 rats per test group) were fasted overnight (19 hours). The rats were then subcutaneously administered 3 μmg/kg, 6 μg/kg or 10 μg/kg of tetrodotoxin (TTX) with a sterile water vehicle or sterile water vehicle alone. The rats were then placed in individual, bedding-free cages and allowed ad libitum access to pre-weighed food and water for two hours. The food and water were then removed and the food was reweighed. Gastric emptying was then assessed four hours later by euthanizing the rats and analyzing the stomach and stomach contents. Data were analyzed using a one-way ANOVA followed by a Dunnett's Multiple Comparison Test, where *P<0.05 as compared to the appropriate vehicle. Data are represented as the means+S.E.M. % Gastric Emptying in 4 hours=(1−(gastric content/food intake))× 100.

Figure 13A:
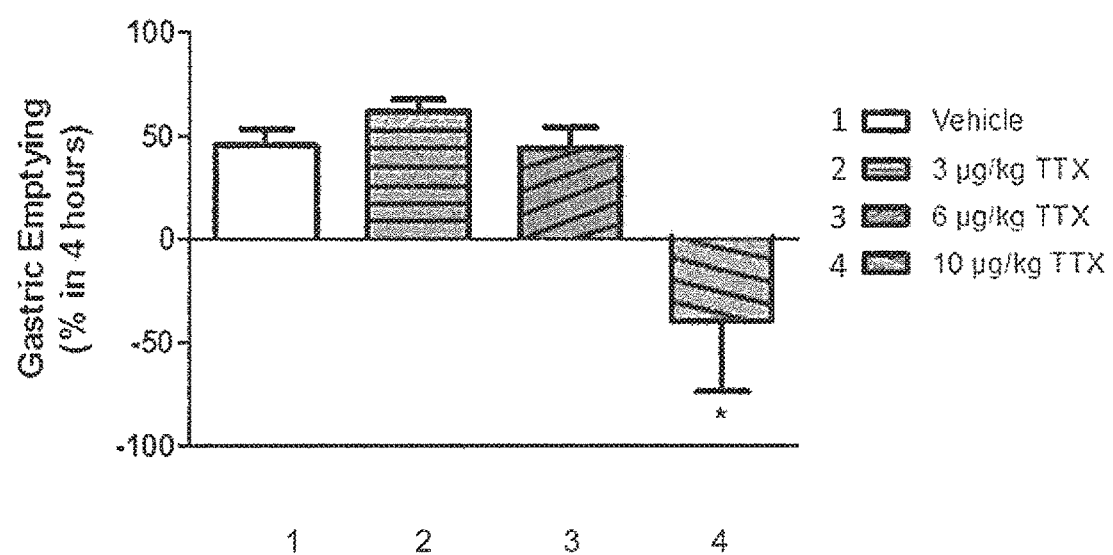
FIGS. 13A-13C are graphical depictions of the effect of subcutaneous dosing of tetrodotoxin (TTX) with a sterile water vehicle on the percentage of gastric emptying, stomach weight, and food intake, respectively, in test animals in accordance with Example 14.
Figure 13B:
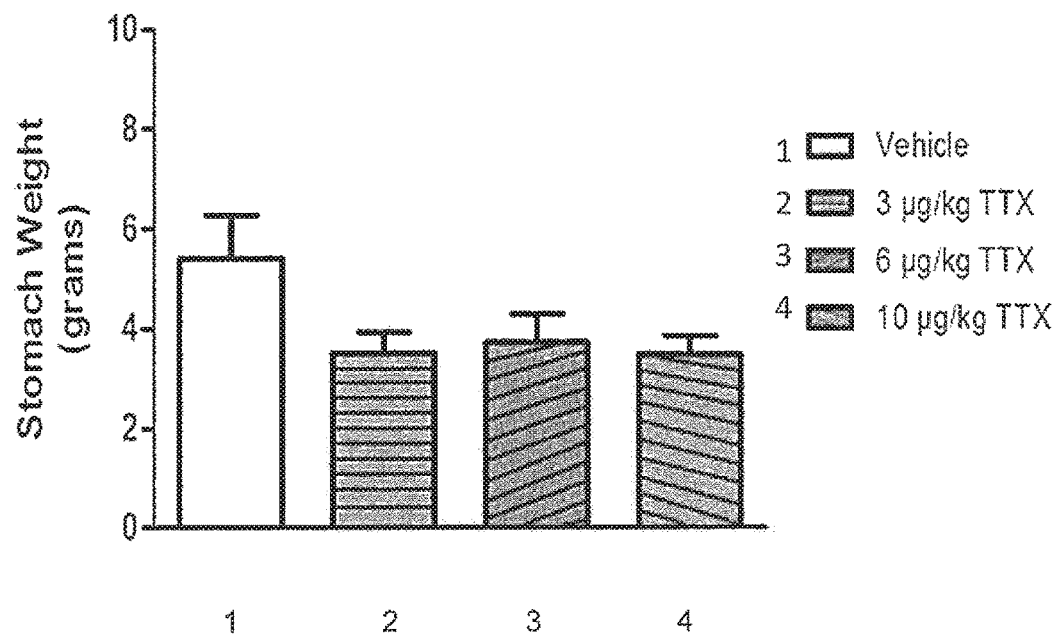
Figure 13C:
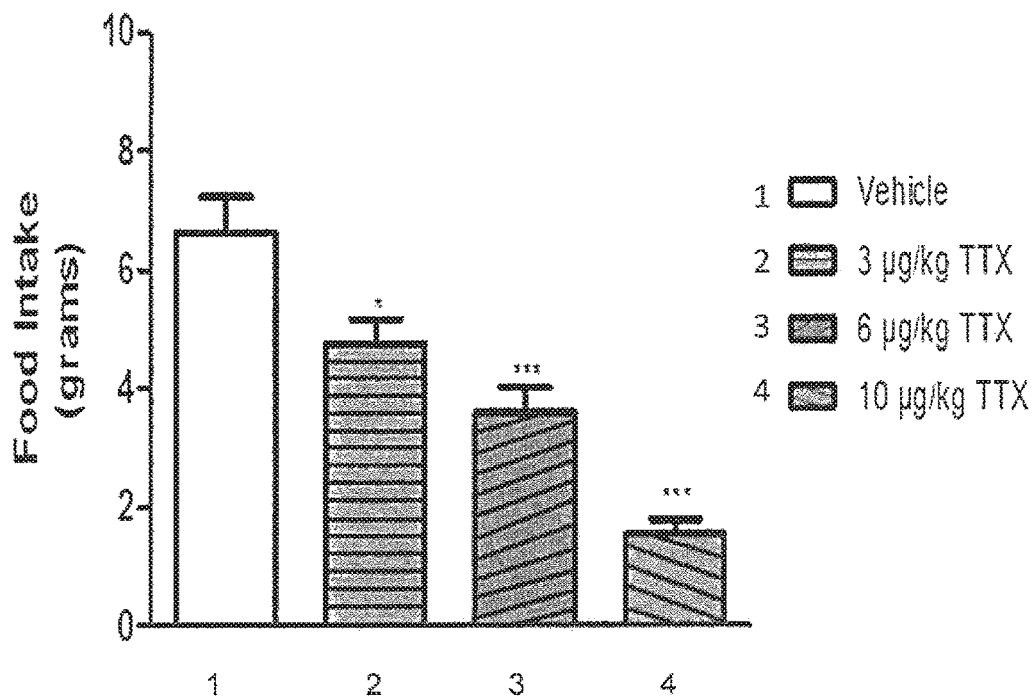

FIG. 13A-13C shows the effect of subcutaneous dosing of TTX on the percent of gastric emptying, stomach weight, and food intake, respectively, in the rats from Example 14. Example 14 and its corresponding figures show that TTX inhibits gastric emptying (FIG. 13A, 10 μg/kg) and reduces food intake (FIG. 13C) as compared to test animals administered a vehicle alone.

Example 15

Mechanism Studies

To investigate the mechanism of action of compounds on gastrointestinal function, three approaches were employed. 1) Combination with known adrenergic receptor antagonists; 2) determining if the effect added to that produced by vagotomy and; 3) determining the effect of the prototypic Nav blocker TTX.

In combination studies Compound A was administered subcutaneously to avoid the potential confound of having two compounds administered by the oral route. Terazosin and Atenolol, antagonists of the alpha 1 and beta 2 adrenergic receptor, respectively, were administered coincident with Compound A and gastric emptying assessed as described above.

Neither terazosin nor atenolol alone had a significant effect on gastric emptying and when co-administered with Compound A did not produce a statistically significant effect on the decrease in gastric emptying produced by Compound A (FIGS. 110A and 11A). As such, we surmised that the effect of Compound A was not mediated via adrenergic receptors.

Vagotomy is known to inhibit gastric emptying (Sheiner, Quinlan et al. 1980) and as such we were interested to see if the effects of Compound A were additive with the deficits in gastric emptying produced by transection of the vagus nerve. Vagotomy produced a large decrease in gastric emptying and coincident increase in stomach weight (FIGS. 12A and B). When dosed alone, Compound A again produced a statistically significant decrease in gastric emptying and increase in stomach weight in naïve animals (FIGS. 12A and B). When Compound A was administered to animals post-vagotomy the resulting effect on gastric emptying and stomach weight was not statically significantly different from vagotomy alone (FIGS. 12A and B). These results suggest that Compound A is mediating its effects via the nervous system.

Finally, to confirm the involvement of Nav channels we tested the prototypic Nav blocker TTX; this compound when a subcutaneously at 10 µg/kg produced a statistically significant decrease in gastric emptying comparable to that achieved by 30 mg/kg of Compound A administered orally (FIG. 13A). In addition TTX produced a dose dependent decrease in food intake (FIG. 13C). Taken together, these data suggest that Compound A is mediating its effects via Nav channels.

Example 16

The Effect of Sodium Channel Blockers on GastroIntestinal Transit

Figure 14A:
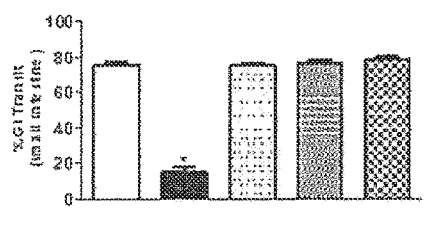
FIGS. 14A-14F are graphical depictions of the results of Example 16.

The effects of Nav channel blockers on gastrointestinal transit using the charcoal meal assay (FIG. 14) was examined. In this assay the leading edge of the charcoal meal following administration of vehicle reaches ~75% of the total length of the small intestine. No statistically significant decrease in gastrointestinal transit was observed for Compounds A, B, or C, although a decreasing trend was observed for Compound B carbamazepine (FIG. 14C). In contrast, the positive control, morphine (10 mg/kg, s.c.) significantly decreased gastrointestinal transit to less than 35% (FIGS. 14A, 14C, and 14E, black column).

Figure 14B:
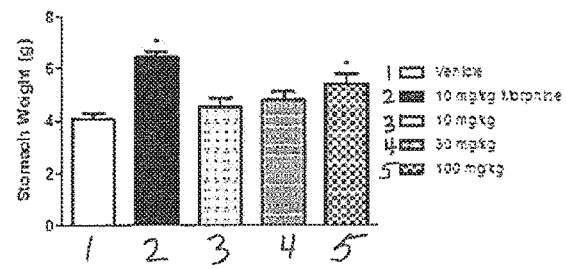
Figure 14C:
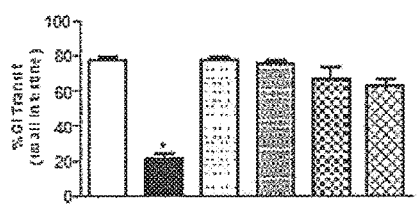
Figure 14D:
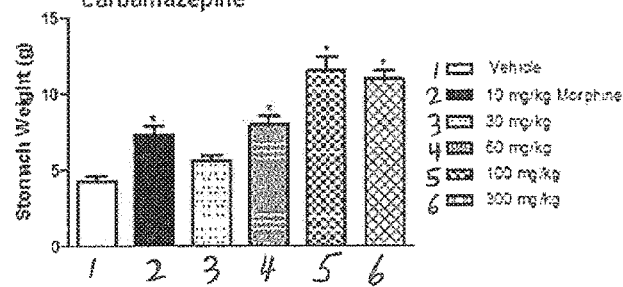
Figure 14E:
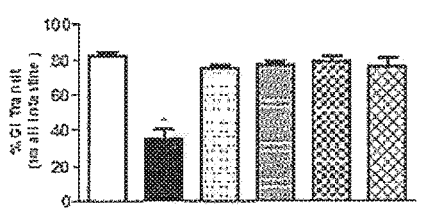
Figure 14F:
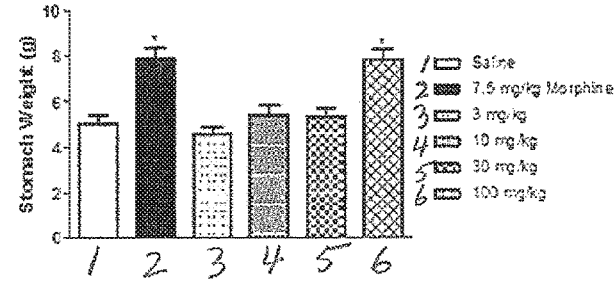

Morphine also increased the subjects' stomach weight from ~4.5 g (vehicle alone, white column) to an average of over 7 g (FIGS. 14B, 14D, and 14F). However, unlike with the gastrointestinal transit, all three Nav blockers (Compounds A, B, and C) did produce a statistically significant increase in stomach weight as compared to vehicle treated animals (FIGS. 14B, 14D, and 14F). Carbamazepine (Compound B) was the most potent in the present example having an effect on the stomach weight at a dose as low as 30 mg/kg. In comparison, Compounds A and C had a significant effect on the stomach weight only at a dosage level of 100 mg/kg.

Example 17

Blockade of Sodium Channels Increases Gastric Secretion which is not Mediated Via the $H^+/K^+$ ATPase (Proton Pump)

An increase in gastric secretion can result in a decrease in gastric emptying (Hunt 1983). Given this, Example 17 assessed whether Compound A had an effect on gastric secretion and pH and if so, if this effect could be reversed using a proton pump inhibitor (FIG. 15). This Example measured volume and pH of gastric secretion three hours post subcutaneous administration of 10 mg/kg of Compound A. The animals were water deprived during this time.

Figure 15A:
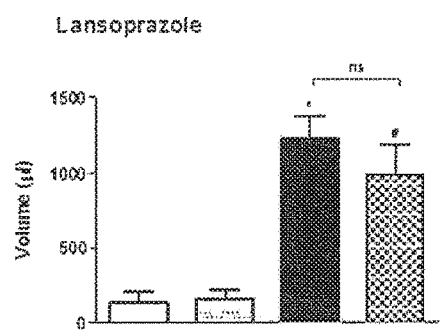
FIGS. 15A-15B are graphical depictions of the results of Example 17.
Figure 15B:
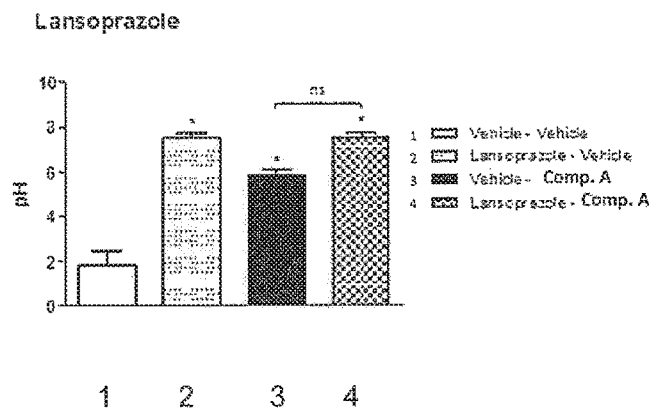

Compound A alone resulted in an increase in gastric secretion and pH as compared the values resulting from subjects administered with vehicle alone (FIGS. 15A and 15B, black versus white column).

Lansoprazole 30 mg/kg administered orally did not affect volume of gastric secretion when administered alone but did, as expected, increase the pH as compared the values resulting from subjects administered with vehicle alone (FIGS. 15A and B, dotted white versus white column).

When lansoprazole was co-administered 30 minutes prior to Compound A the resulting effects on volume and pH were not different from that achieved by Compound A alone (FIGS. 15A and B). These results demonstrate that while Compound A increases gastric secretion and raises pH this effect is not mediated via interaction with the parietal cell $H^+/K^+$ ATPase.

Example 18

Figure 16A:
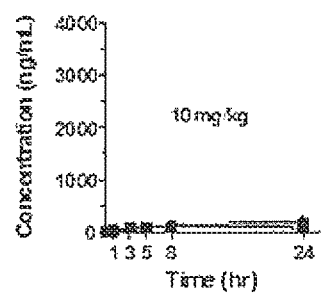
FIG. 16A-16C are graphical depictions of the results of Example 18.
Figure 16B:
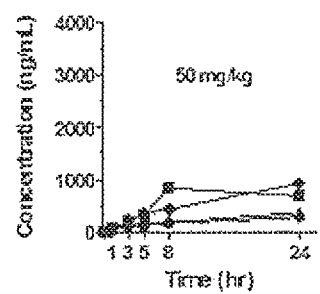
Figure 16C:
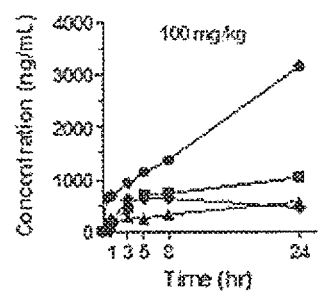

The Gastrointestinal Effects of Sodium Channel Blockade are not Unique to Species that Possess a Forestomach Example 18 investigated if the above effects of Nav blockade were restricted to animals that possess a forestomach such as the rat and mouse. As such, a pharmacokinetic and observational study was conducted in cynomologous monkeys (FIG. 16). Plasma concentrations of Compound A were measured following a single oral dose of 10, 50 and 100 mg/kg up to 24 hours post-dosing (FIGS. 16A, B and C). Similar to PK studies in rats, plasma concentrations were measurable at all doses. The plasma levels increased with increasing dose in an approximately linear fashion. The plasma concentration also increased with time and continued increasing up to 8 hours for the 10 mg/kg dosage and up to 24 hour in the 50 mg/kg and 100 mg/kg dosage.

Clinical observations relevant to the gastrointestinal system are shown in Table 3.

TABLE 3

| | Dose (mg/kg) | | |
|---|---|---|---|
| | 10 | 50 | 100 |
| Clinical Observations (frequency) | Diarrhea (2/3) | Distended/Bloated Abdomen (2/4) | Distended/Bloated Abdomen (2/4) Low Food Consumption (2/4) |

At the low dose of 10 mg/kg diarrhea was observed in 2 out of the 3 animals however, no treatment related-effect was discernable in terms of food consumption or feces production at this dose. At the two higher doses studied (50 mg/kg and 100 mg/kg) distended and bloated abdomens were observed in 2 out of 4 animals. At the highest dose tested, 100 mg/kg, low food consumption was also noted in 2 out of the 4 animals tested. The individual monkey presenting the highest plasma levels (over 3000 ng/ml at 24 hrs) exhibited zero food intake and zero feces production up to 24 hrs post-dosing and continued to exhibit reduced food intake for at least two additional days post dosing. This data confirms that the effects of Nav blockade quantified in rats also occur, at least in qualitative studies, in species that lack a forestomach such as monkeys.

What is claimed is:

1. A method of decreasing gastric emptying comprising: administering to a subject an effective amount of a sodium-channel blocker to decrease gastric emptying, wherein the sodium-channel blocker is a compound of Formula I:

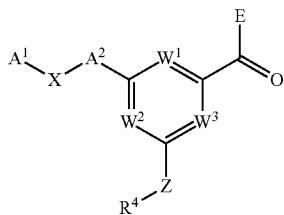

(I)

or a pharmaceutically acceptable salt, solvate, or prodrug thereof, wherein two of $W^1$, $W^2$, or $W^3$ are N and the remaining one is $CR^3$; wherein $R^3$ selected from the group consisting of: hydrogen; halo; nitro; cyano; hydroxy; amino; alkylamino; dialkylamino; haloalkyl; hydroxyalkyl; alkoxy; haloalkoxy; and alkoxyalkyl;

$A^1$ is selected from the group consisting of optionally substituted aryl; optionally substituted heteroaryl; optionally substituted cycloalkyl; optionally substituted heterocyclo; and aralkyl;

X is selected from the group consisting of —O—; —S—; —SO—; —SO$_2$—; —(CR$^{7a}$R$^{7b}$)$_m$—; —NR$^8$—; —SO$_2$NR$^9$—; and —NR$^9$SO$_2$—;

Each $R^{7a}$ and $R^{7b}$, independently, is selected from the group consisting of hydrogen; halo; and alkyl; or Each $R^{7a}$ and $R^{7b}$ taken together with the carbon atom to which they are attached form a 3- to 8-membered optionally substituted cycloalkyl or a 3- to 8-membered optionally substituted heterocyclo; m is 0, 1, 2, or 3; $R^8$ and $R^9$ are independently selected from the group consisting of hydrogen and alkyl; $A^2$ is selected from the group consisting of optionally substituted aryl; optionally substituted heteroaryl; optionally substituted heterocyclo; and optionally substituted cycloalkyl; or $A^2$ is absent;

E is selected from the group consisting of hydroxy; alkoxy; and —NR$^1$R$^2$; wherein $R^1$ is selected from the group consisting of: hydrogen; alkyl; aralkyl; (heterocyclo)alkyl; (heteroaryl)alkyl; (amino)alkyl; (alkylamino)alkyl; (dialkylamino)alkyl; (carboxamido)alkyl; (cyano)alkyl; alkoxyalkyl; hydroxyalkyl; and heteroalkyl; $R^2$ is selected from the group consisting of hydrogen and alkyl; or $R^1$ and $R^2$ taken together with the nitrogen atom to which they are attached form a 3- to 8-membered optionally substituted heterocyclo;

Z is selected from the group consisting of —NR$^5$— and —O—; wherein $R^5$ is selected from the group consisting of: hydrogen; alkyl; hydroxyalkyl; and alkylsulfonyl; and $R^4$ is selected from the group consisting of

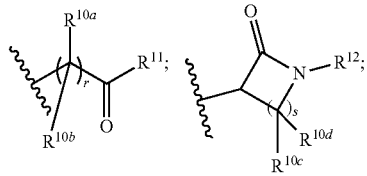

hydroxyalkyl; hydroxy(cycloalkyl)alkyl; and (heterocyclo)alkyl; or wherein $R^4$ and $R^5$ taken together with the nitrogen atom to which they are attached form a 3- to 8-membered optionally substituted heterocyclo;

Each $R^{10a}$, $R^{10b}$, $R^{10c}$, and $R^{10d}$ is independently selected from the group consisting of: hydrogen; hydroxy; optionally substituted alkyl; aralkyl; (heterocyclo)alkyl; (heteroaryl)alkyl; (amino)alkyl; (alkylamino)alkyl; (dialkylamino)alkyl; (carboxamido)alkyl; (cyano)alkyl; alkoxyalkyl; hydroxyalkyl; heteroalkyl; optionally substituted cycloalkyl; optionally substituted aryl; optionally substituted heterocyclo; and optionally substituted heteroaryl; or $R^{10a}$ and $R^{10b}$ taken together with the carbon atom to which they are attached form a 3- to 8-membered optionally substituted cycloalkyl or a 3- to 8-membered optionally substituted heterocyclo;

r and s are independently 1, 2, or 3;

$R^{11}$ is selected from the group consisting of: hydroxy; alkoxy; and —NR$^{1a}$R$^{2a}$;

$R^{1a}$ is selected from the group consisting of: hydrogen; alkyl; aralkyl; (heterocyclo)alkyl; (heteroaryl)alkyl; (amino)alkyl; (alkylamino)alkyl; (dialkylamino)alkyl; (carboxamido)alkyl; (cyano)alkyl; alkoxyalkyl; hydroxyalkyl; and heteroalkyl;

$R^{2a}$ is selected from the group consisting of hydrogen and alkyl; or $R^{1a}$ and $R^{2a}$ taken together with the nitrogen atom to which they are attached form a 3- to 8-membered optionally substituted heterocyclo;

$R^{12}$ is selected from the group consisting of hydrogen; optionally substituted alkyl; (amino)alkyl; (alkylamino)alkyl; (dialkylamino)alkyl; (carboxamido)alkyl; (cyano)alkyl; alkoxyalkyl; hydroxyalkyl; and heteroalkyl.

2. The method of claim 1, wherein the subject is treated for an indication selected from the group consisting of rapid gastric emptying, early rapid gastric emptying, late rapid gastric emptying, weight gain, increased food intake, metabolic syndrome, obesity, diabetes mellitus (type 1 and type 2), sclerodoma, migraine episodes, post-prandial rise in blood glucose, nerve damage, Zollinger-Ellison syndrome, cyclic vomiting syndrome, short bowl syndrome, impaired gastric accommodation, pouch emptying in Roux-en-Y Gastric Bypass (RYGB), and functional dyspepsia.

3. The method of claim 1, wherein the subject is treated for a symptom selected from the group consisting of cramping, pain, abdominal pain, nausea, vomiting, diarrhea, sweating, flushing, light-headedness, rapid or irregular heartbeat, bloating, dizziness, fatigue, concentration difficulties, anxiety, sitophobia, weight gain, malnutrition, shortness of breath, low blood pressure, weakness, reduced food intake, increased food intake and hypoglycemia.

4. The method of claim 1, wherein the subject has undergone gastric surgery, esophageal surgery, gastrectomy, gastroenterostomy, vagotomy, fundoplication, esophagectomy, gastric bypass or bariatric surgery.

5. The method of claim 1, wherein the subject is prophylactically treated for rapid gastric emptying.

6. The method of claim 1, wherein the administration is selected from a route selected from the group consisting of oral, parenteral, subcutaneous, intravenous, intramuscular, intraperitoneal, transdermal, sublingual, buccal, gingival, rectal, subcutaneous, transpulmonary and topical.

7. The method of claim 1, wherein the sodium-channel blocker is contained in a dosage form selected from the group consisting of a tablet, troche, lozenge, powder, granule, hard or soft capsule, microparticle, buccal tablet, transdermal patch, liquid, solution, suspension and suppository.

8. The method of claim 1, wherein the subject exhibits an increase in stomach acidity after the administration.

9. The method of claim 1, wherein the sodium-channel blocker is a 4-N substituted pyrimidine amide compound.

10. The method of claim 1, wherein the sodium-channel blocker is:

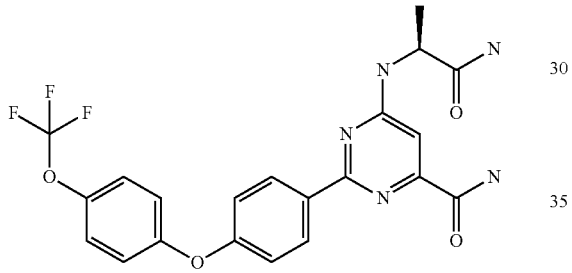

or a pharmaceutically acceptable salt, solvate, or prodrug thereof.

11. A method of weight management comprising:
administering to a subject an effective amount of a sodium-channel blocker to increase weight loss, wherein the sodium-channel blocker is a compound of Formula I:

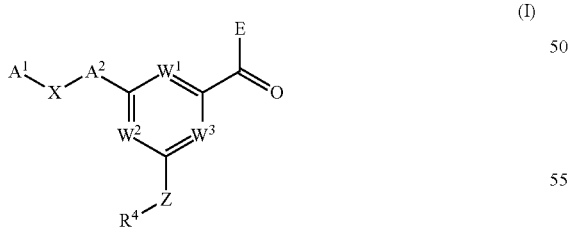

or a pharmaceutically acceptable salt, solvate, or prodrug thereof,
wherein two of $W^1$, $W^2$, or $W^3$ are N and the remaining one is $CR^3$; wherein $R^3$ selected from the group consisting of: hydrogen; halo; nitro; cyano; hydroxy; amino; alkylamino; dialkylamino; haloalkyl; hydroxyalkyl; alkoxy; haloalkoxy; and alkoxyalkyl; $A^1$ is selected from the group consisting of optionally substituted aryl; optionally substituted heteroaryl; optionally substituted cycloalkyl; optionally substituted heterocyclo; and aralkyl;

X is selected from the group consisting of —O—; —S—; —SO—; —SO$_2$—; —(CR$^{7a}$R$^{7b}$)$_m$—; —NR$^8$—; —SO$_2$NR$^9$—; and —NR$^9$SO$_2$—;

Each $R^{7a}$ and $R^{7b}$, independently, is selected from the group consisting of hydrogen; halo; and alkyl; or Each $R^{7a}$ and $R^{7b}$ taken together with the carbon atom to which they are attached form a 3- to 8-membered optionally substituted cycloalkyl or a 3- to 8-membered optionally substituted heterocyclo; m is 0, 1, 2, or 3; $R^8$ and $R^9$ are independently selected from the group consisting of hydrogen and alkyl; $A^2$ is selected from the group consisting of optionally substituted aryl; optionally substituted heteroaryl; optionally substituted heterocyclo; and optionally substituted cycloalkyl; or $A^2$ is absent;

E is selected from the group consisting of hydroxy; alkoxy; and —NR$^1$R$^2$; wherein $R^1$ is selected from the group consisting of: hydrogen; alkyl; aralkyl; (heterocyclo)alkyl; (heteroaryl)alkyl; (amino)alkyl; (alkylamino)alkyl; (dialkylamino)alkyl; (carboxamido)alkyl; (cyano)alkyl; alkoxyalkyl; hydroxyalkyl; and heteroalkyl; $R^2$ is selected from the group consisting of hydrogen and alkyl; or $R^1$ and $R^2$ taken together with the nitrogen atom to which they are attached form a 3- to 8-membered optionally substituted heterocyclo;

Z is selected from the group consisting of —NR$^5$— and —O—; wherein $R^5$ is selected from the group consisting of: hydrogen; alkyl; hydroxyalkyl; and alkylsulfonyl; and $R^4$ is selected from the group consisting of

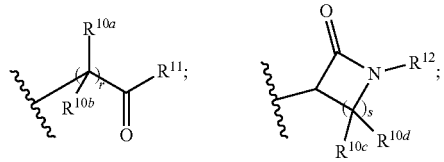

hydroxyalkyl; hydroxy(cycloalkyl)alkyl; and (heterocyclo)alkyl; or
wherein $R^4$ and $R^5$ taken together with the nitrogen atom to which they are attached form a 3- to 8-membered optionally substituted heterocyclo;

Each $R^{10a}$, $R^{10b}$, $R^{10c}$, and $R^{10d}$ is independently selected from the group consisting of: hydrogen; hydroxy; optionally substituted alkyl; aralkyl; (heterocyclo)alkyl; (heteroaryl)alkyl; (amino)alkyl; (alkylamino)alkyl; (dialkylamino)alkyl; (carboxamido)alkyl; (cyano)alkyl; alkoxyalkyl; hydroxyalkyl; heteroalkyl; optionally substituted cycloalkyl; optionally substituted aryl; optionally substituted heterocyclo; and optionally substituted heteroaryl; or $R^{10a}$ and $R^{10b}$ taken together with the carbon atom to which they are attached form a 3- to 8-membered optionally substituted cycloalkyl or a 3- to 8-membered optionally substituted heterocyclo;

r and s are independently 1, 2, or 3;

$R^{11}$ is selected from the group consisting of: hydroxy; alkoxy; and —NR$^{1a}$R$^{2a}$;

$R^{1a}$ is selected from the group consisting of: hydrogen; alkyl; aralkyl; (heterocyclo)alkyl; (heteroaryl)alkyl; (amino)alkyl; (alkylamino)alkyl; (dialkylamino)

alkyl; (carboxamido)alkyl; (cyano)alkyl; alkoxyalkyl; hydroxyalkyl; and heteroalkyl;

$R^{2a}$ is selected from the group consisting of hydrogen and alkyl; or $R^{1a}$ and $R^{2a}$ taken together with the nitrogen atom to which they are attached form a 3- to 8-membered optionally substituted heterocyclo;

$R^{12}$ is selected from the group consisting of hydrogen; optionally substituted alkyl; (amino)alkyl; (alkylamino)alkyl; (dialkylamino)alkyl; (carboxamido)alkyl; (cyano)alkyl; alkoxyalkyl; hydroxyalkyl; and heteroalkyl.

* * * * *